US012357812B2

(12) United States Patent
Rassat et al.

(10) Patent No.: US 12,357,812 B2
(45) Date of Patent: Jul. 15, 2025

(54) LEAD CONSTRUCTION INCLUDING ALIGNABLE MARKER ELEMENTS

(71) Applicant: Medtronic, Inc., Minneapolis, MN (US)

(72) Inventors: Jay T. Rassat, Otsego, MN (US); Varun Bhatia, Minneapolis, MN (US); Kendall Emfield, Excelsior, MN (US); Ryan Lahm, Lino Lakes, MN (US); Alan Cheng, Minneapolis, MN (US); Douglas S. Hine, Forest Lake, MN (US); Kristin M. Johnson, Circle Pines, MN (US); Gregory N. Nesseth, Forest Lake, MN (US); Jonathan E. Baxter, Fridley, MN (US); Daniel W. Celotta, Circle Pines, MN (US); Stephen A. Howard, Forest Lake, MN (US); Nathan A. Grenz, North Oaks, MN (US); Brian P. Colin, Anoka, MN (US); Ronald A. Drake, St. Louis Park, MN (US); Juan Meng, Shanghai (CN); Hongyang Lu, Shanghai (CN)

(73) Assignee: Medtronic, Inc., Minneapolis, MN (US)

( * ) Notice: Subject to any disclaimer, the term of this patent is extended or adjusted under 35 U.S.C. 154(b) by 580 days.

(21) Appl. No.: 17/579,064

(22) Filed: Jan. 19, 2022

(65) Prior Publication Data

US 2022/0226636 A1  Jul. 21, 2022

Related U.S. Application Data

(60) Provisional application No. 63/139,662, filed on Jan. 20, 2021, provisional application No. 63/139,661, filed on Jan. 20, 2021.

(51) Int. Cl.
*A61N 1/05* (2006.01)
*A61N 1/375* (2006.01)
(Continued)

(52) U.S. Cl.
CPC .............. *A61N 1/05* (2013.01); *B33Y 10/00* (2014.12); *B33Y 30/00* (2014.12); *B33Y 80/00* (2014.12)

(58) Field of Classification Search
CPC ..................... A61B 90/39; A61B 2090/3966
See application file for complete search history.

(56) References Cited

U.S. PATENT DOCUMENTS 2,764,148 A   9/1956  Sheldon
3,485,234 A  12/1969  Stevens
(Continued)

FOREIGN PATENT DOCUMENTS

CA      2998126      10/2018
CN    109715244       5/2019
(Continued)

OTHER PUBLICATIONS

International Preliminary Report on Patentability for PCT Application No. PCT/US2021/024640 dated Oct. 13, 2022, 10 pages.
(Continued)

*Primary Examiner* — Brian T Gedeon
(74) *Attorney, Agent, or Firm* — Mueting Raasch Group

(57) ABSTRACT

Implantable apparatus includes two or more alignable marker elements, and systems and methods for manufacturing such implantable apparatus, and methods to utilize such implantable apparatus. For example, the implantable apparatus may include a first alignable marker element and a second alignable marker element that may be used to ensure proper alignment with a target site.

16 Claims, 41 Drawing Sheets

(51) Int. Cl.
  *B33Y 10/00*  (2015.01)
  *B33Y 30/00*  (2015.01)
  *B33Y 80/00*  (2015.01)

(56) References Cited

U.S. PATENT DOCUMENTS

| | | | |
|---|---|---|---|
| 5,871,475 | A | 2/1999 | Frassica |
| 6,187,130 | B1 | 2/2001 | Berard |
| 6,548,010 | B1 | 4/2003 | Stivland |
| 6,591,472 | B1 | 7/2003 | Noone et al. |
| 7,306,617 | B2 | 12/2007 | Majercak |
| 7,833,218 | B2 | 11/2010 | Lunn et al. |
| 7,909,033 | B2 | 3/2011 | Faram |
| 8,118,827 | B2 | 2/2012 | Duerig et al. |
| 8,509,916 | B2 | 8/2013 | Byrd et al. |
| 8,744,595 | B2 * | 6/2014 | Tronnes ............ A61B 5/24 |
| | | | 607/116 |
| 9,002,496 | B2 | 4/2015 | Elsey |
| 9,043,191 | B2 | 5/2015 | Grady et al. |
| 9,974,887 | B2 | 5/2018 | Eversull et al. |
| 10,254,499 | B1 | 4/2019 | Cohen et al. |
| 10,327,862 | B2 | 6/2019 | Lubinski |
| 10,442,175 | B2 | 10/2019 | Schlachter |
| 10,548,355 | B2 | 2/2020 | Volpis et al. |
| 10,610,666 | B2 | 4/2020 | Stern |
| 10,751,507 | B2 | 8/2020 | Palmer et al. |
| 11,160,952 | B2 | 11/2021 | Bridgeman |
| 11,707,332 | B2 * | 7/2023 | Bell ............ A61B 34/20 |
| | | | 600/426 |
| 2004/0002677 | A1 | 1/2004 | Gentsler |
| 2007/0005041 | A1 | 1/2007 | Frassica et al. |
| 2007/0060863 | A1 | 3/2007 | Goeken et al. |
| 2008/0262472 | A1 | 10/2008 | Lunn et al. |
| 2012/0149985 | A1 | 6/2012 | Frassica et al. |
| 2014/0361460 | A1 | 12/2014 | Mark |
| 2015/0217517 | A1 | 8/2015 | Karpas et al. |
| 2016/0096323 | A1 | 4/2016 | Fry et al. |
| 2016/0101262 | A1 | 4/2016 | Root et al. |
| 2016/0184233 | A1 | 6/2016 | Palomar-Moreno et al. |
| 2016/0207220 | A1 | 7/2016 | Hack et al. |
| 2017/0156750 | A1 | 6/2017 | Root |
| 2017/0182290 | A1 | 6/2017 | Stern |
| 2017/0189553 | A1 | 7/2017 | Hunter |
| 2017/0259506 | A1 | 9/2017 | Ho et al. |
| 2018/0036123 | A1 | 2/2018 | Costello |
| 2018/0065320 | A1 | 3/2018 | Tyler |
| 2018/0104472 | A1 * | 4/2018 | Govea ............ A61N 1/05 |
| 2018/0117855 | A1 | 5/2018 | Girou et al. |
| 2018/0141274 | A1 | 5/2018 | Fink et al. |
| 2018/0168687 | A1 | 6/2018 | Drake et al. |
| 2018/0250498 | A1 | 9/2018 | Stern |
| 2018/0254099 | A1 | 9/2018 | Beydoun et al. |
| 2018/0257444 | A1 * | 9/2018 | Hack ............ B60D 1/06 |
| 2018/0289925 | A1 | 10/2018 | Palmer et al. |
| 2018/0370117 | A1 | 12/2018 | Gardiner et al. |
| 2019/0002625 | A1 | 1/2019 | Jiang et al. |
| 2019/0209080 | A1 | 7/2019 | Gullotti et al. |
| 2019/0240456 | A1 | 8/2019 | Pokorny et al. |
| 2019/0351185 | A1 | 11/2019 | Assouline et al. |
| 2020/0080237 | A1 | 3/2020 | Vogt et al. |
| 2020/0093505 | A1 | 3/2020 | Sinelnikov et al. |
| 2020/0230397 | A1 * | 7/2020 | Li ............ A61B 90/39 |
| 2021/0122115 | A1 | 4/2021 | Ramos |
| 2021/0154473 | A1 * | 5/2021 | Pobiel ............ A61N 1/3605 |
| 2021/0236767 | A1 | 8/2021 | Warnock, Jr. et al. |
| 2021/0298730 | A1 | 9/2021 | Baxter et al. |
| 2022/0032002 | A1 | 2/2022 | Baxter et al. |
| 2022/0032003 | A1 | 2/2022 | Baxter et al. |
| 2022/0032537 | A1 | 2/2022 | Baxter et al. |
| 2022/0233814 | A1 | 7/2022 | Mullins |

FOREIGN PATENT DOCUMENTS

| | | |
|---|---|---|
| EP | 1053039 | 11/2000 |
| KR | 101863192 | 6/2018 |
| WO | 2014/172545 | 10/2014 |
| WO | 2016/168505 | 10/2016 |
| WO | 2019/070899 | 4/2019 |
| WO | WO-2022236067 A1 * | 11/2022 ........... A61N 1/0553 |

OTHER PUBLICATIONS

Ascend Medical Technologies, "Design Guidelines for 3D X-Fusion Technology", ascendmedtech.com/design-guidelines, retrieved Oct. 25, 2019, 3 pages.
Ascend Medical Technologies, "Engineering Capabilities", ascendmedtech.com/design-guidelines, retrieved Oct. 25, 2019, 7 pages.
Baxter et al., U.S. Appl. No. 17/215,842, filed Mar. 29, 2021.
Dilberoglu et al., "Current trends and research opportunities in hybrid additive manufacturing", The International Journal of Advanced Manufacturing Technology, 113, 2021, pp. 623-648.
Gardeski et al., U.S. Appl. No. 17/215,842, filed Mar. 29, 2021.
Gardeski et al., U.S. Appl. No. 63/001,832, filed Mar. 30, 2020.
Ramos et al., U.S. Appl. No. 17/081,815, filed Oct. 27, 2020.
Ramos et al., U.S. Appl. No. 62/927,092, filed Oct. 28, 2019.
Warnock Jr. et al., U.S. Appl. No. 17/162,101, filed Jan. 29, 2021.
Warnock Jr. et al., U.S. Appl. No. 62/970,561, filed Feb. 5, 2020.
International Search Report and Written Opinion from PCT/US2021/043795 dated Oct. 20, 2021, 14 pages.
International Search Report and Written Opinion prepared for International Application No. PCT/US2021/043794, mailed Nov. 23, 2021. 11 pages.
International Search Report and Written Opinion from PCT Application No. PCT/US2021/024640 dated Sep. 13, 2021, 17 pages.
International Search Report and Written Opinion in PCT Application No. PCT/US2022/012966, dated Jun. 13, 2022, 19 pages.
Office Action issued in China for Application No. 202180021033.2 dated Mar. 19, 2025 (10 pages). English translation included.

* cited by examiner

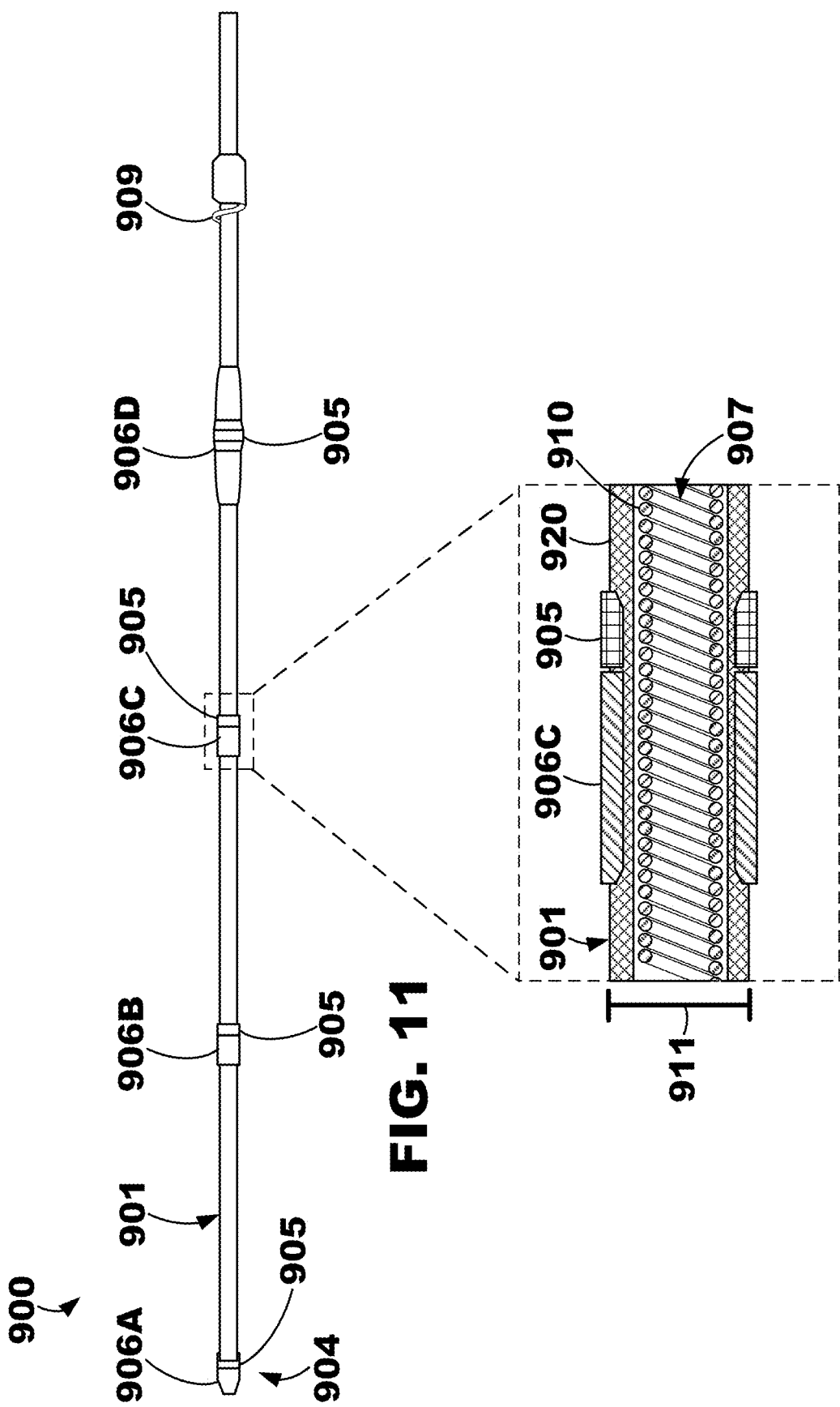

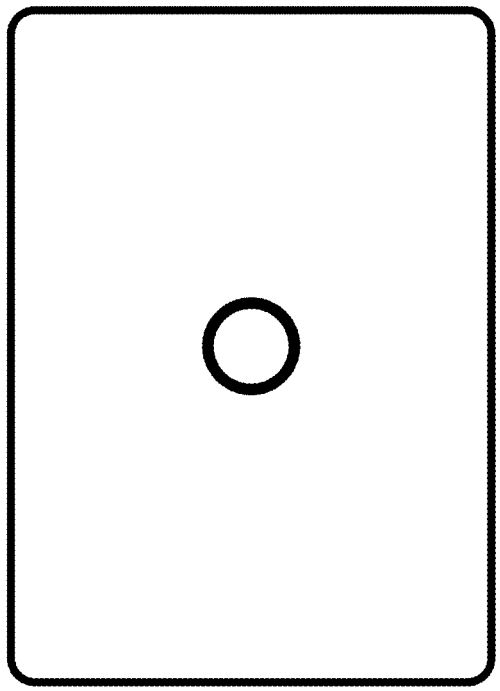
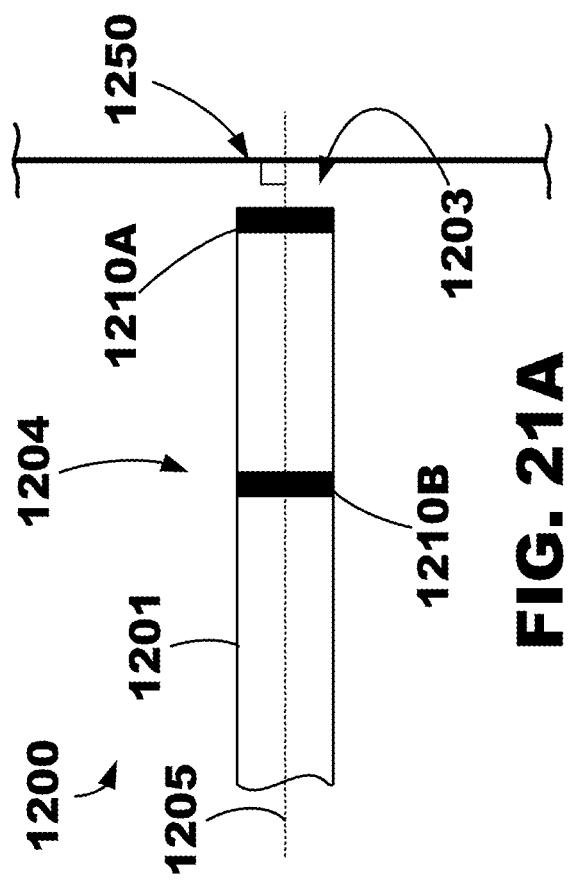

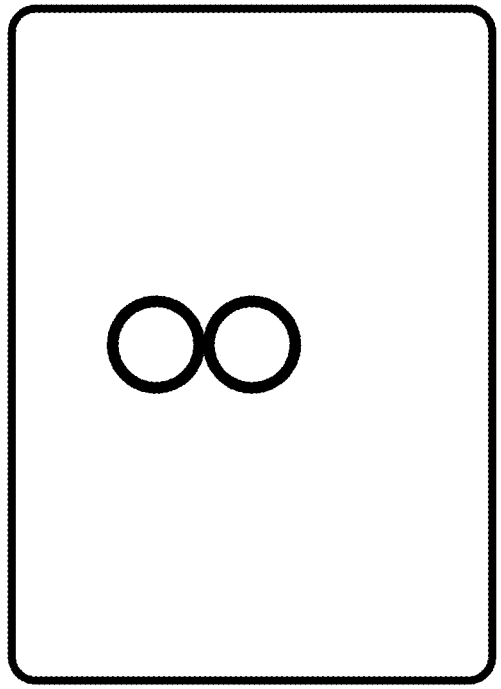
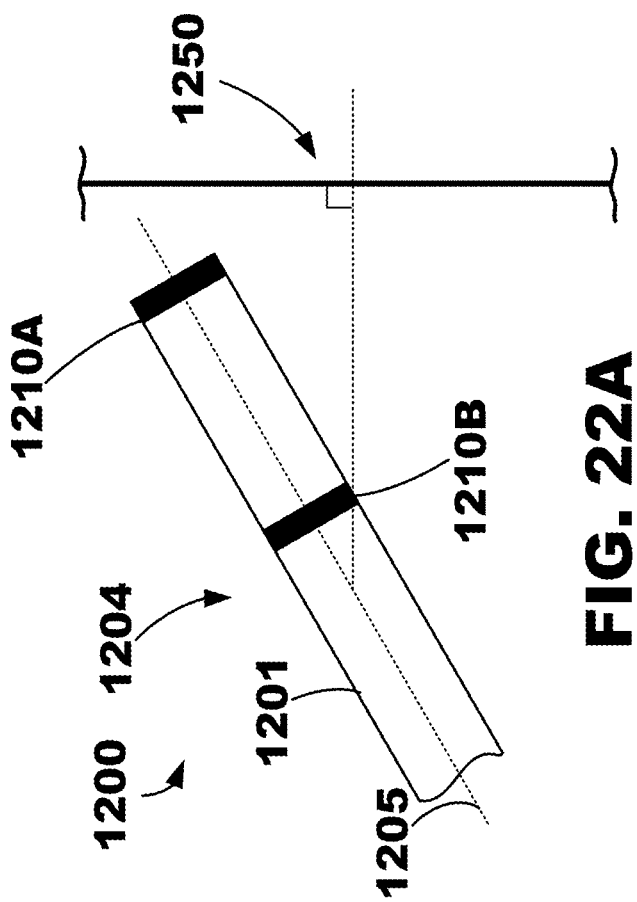
FIG. 22A
FIG. 22B

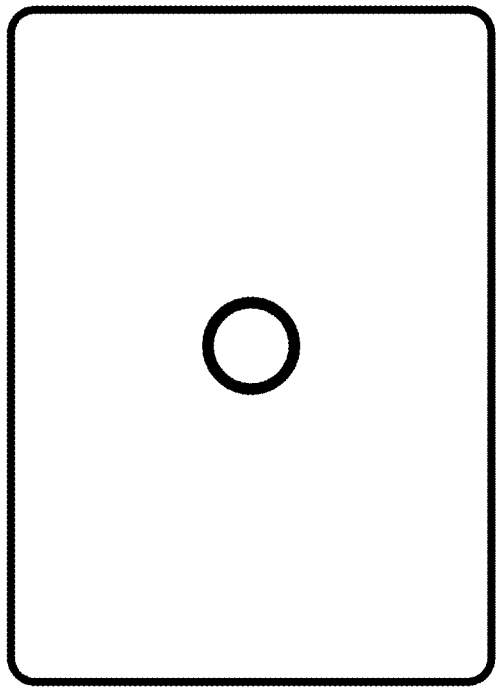
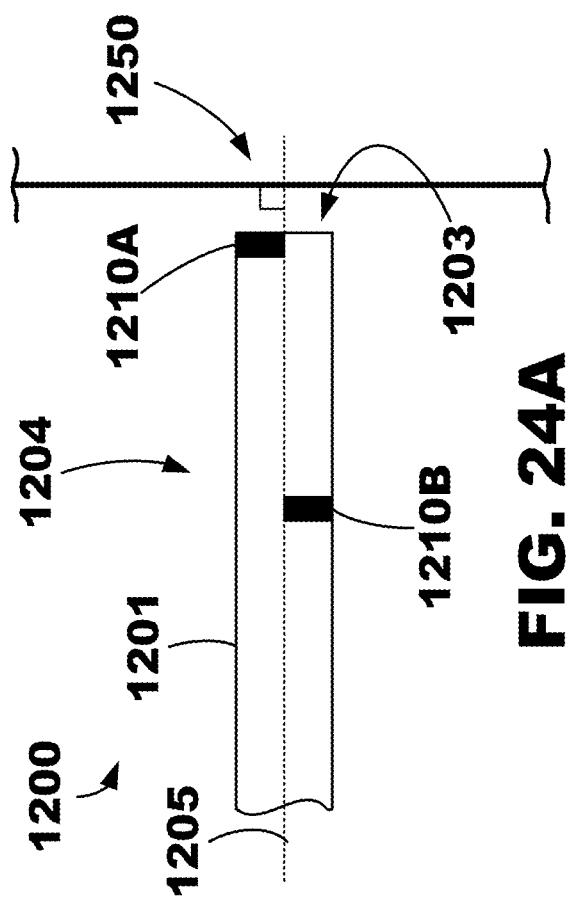

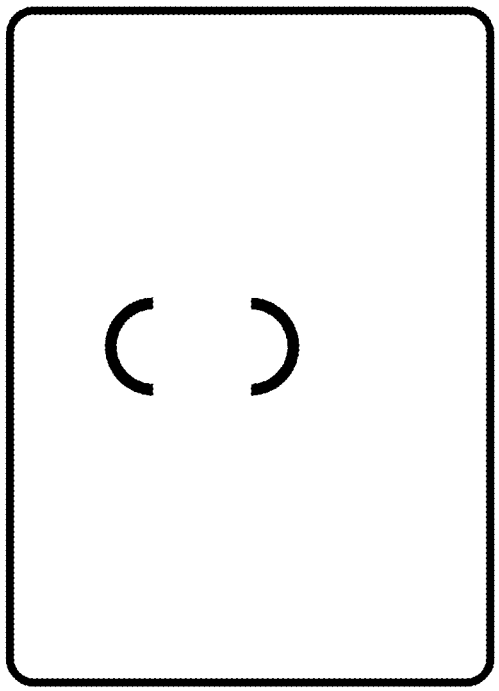
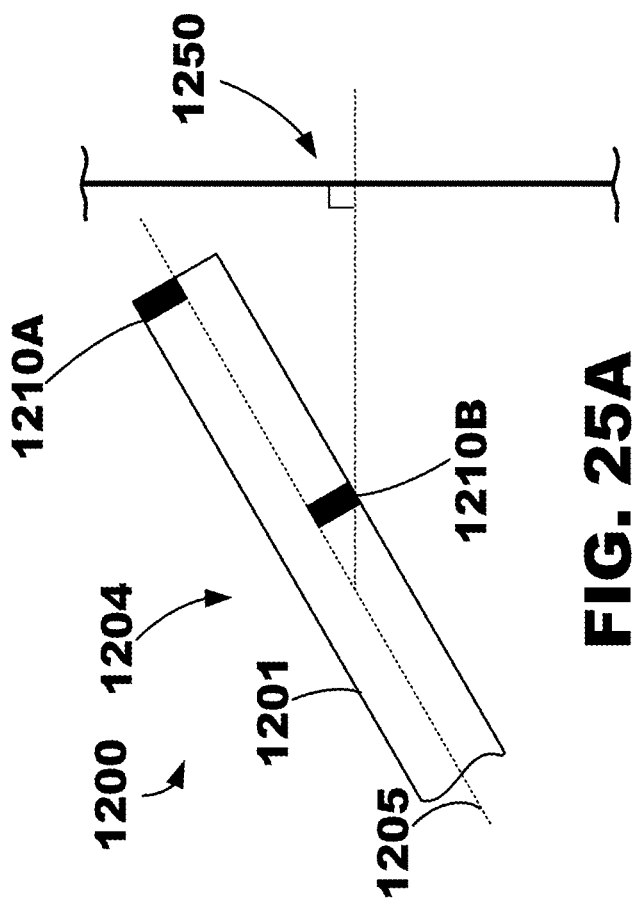

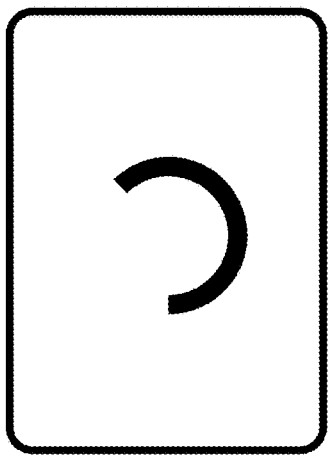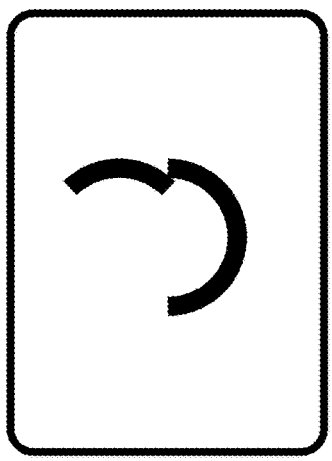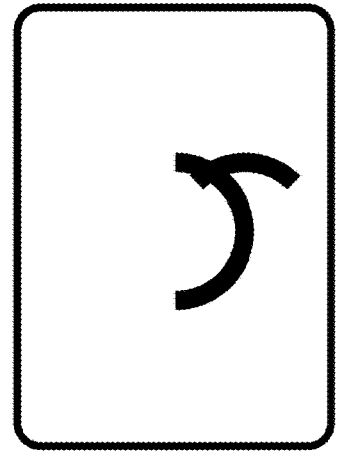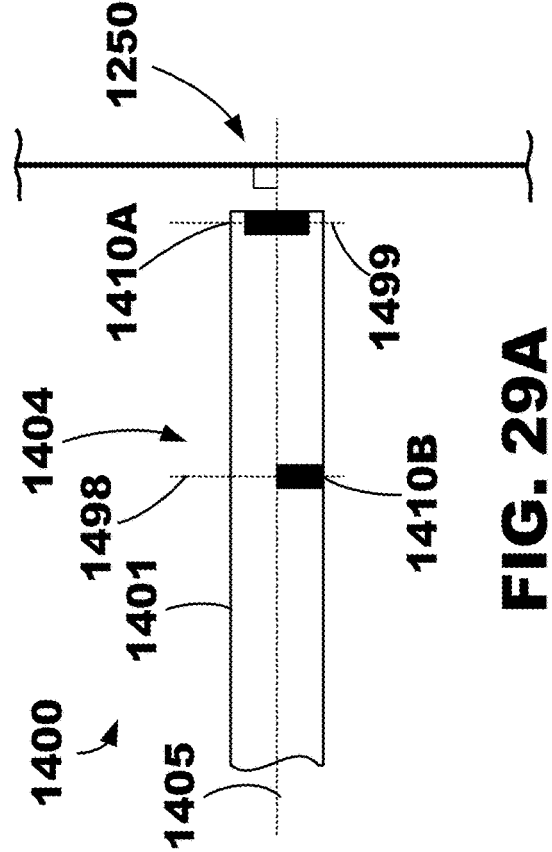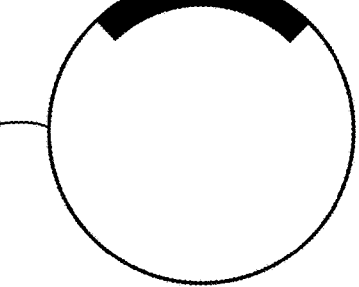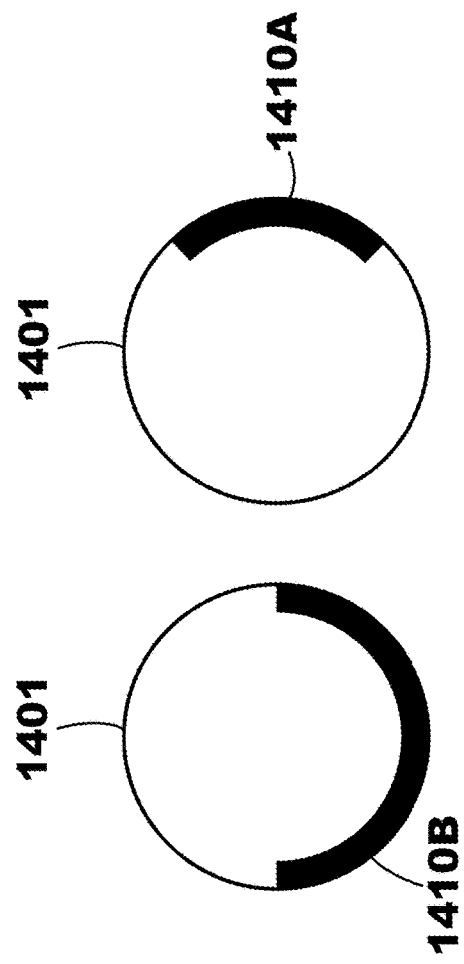

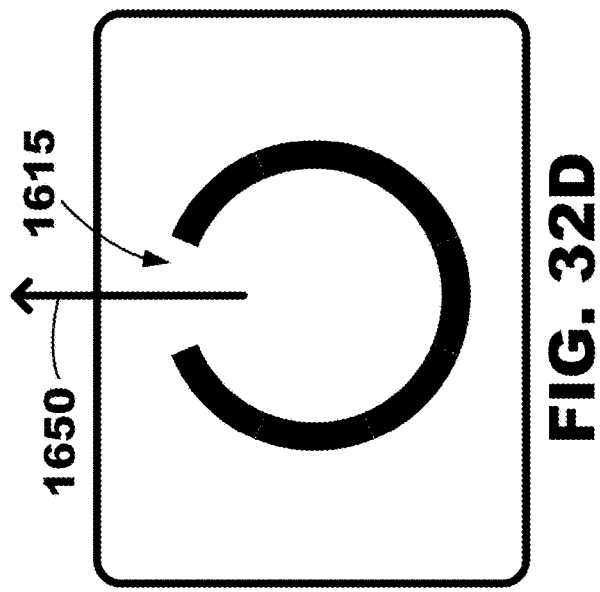
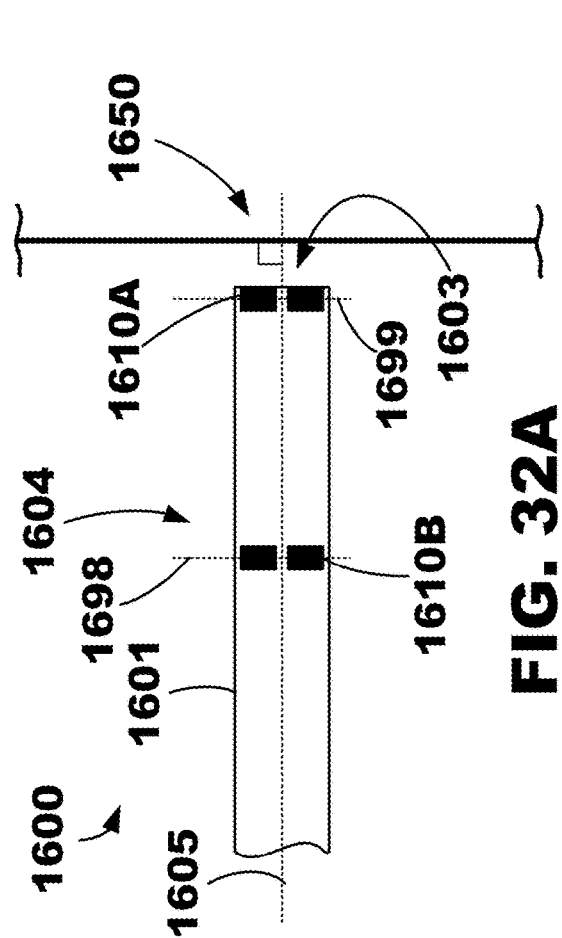
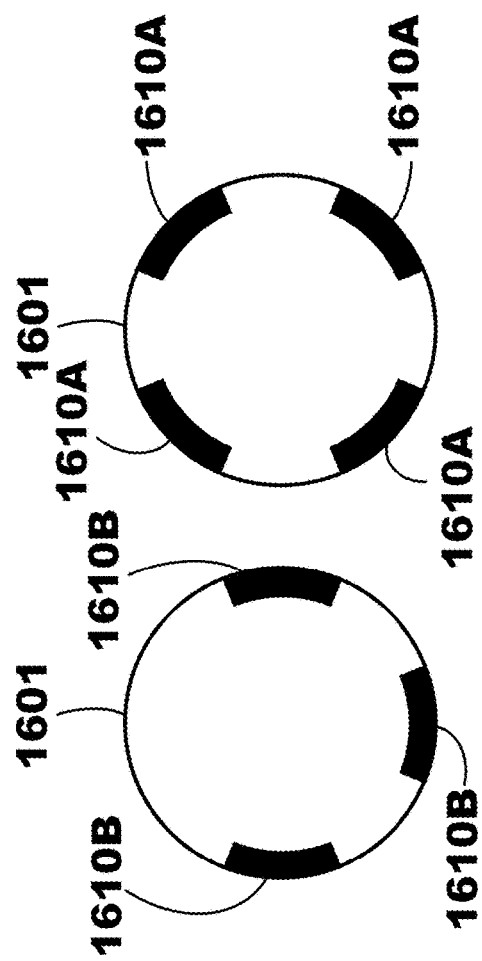

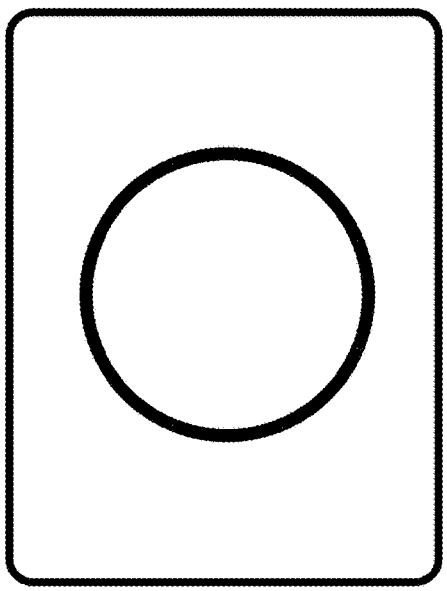
FIG. 33D
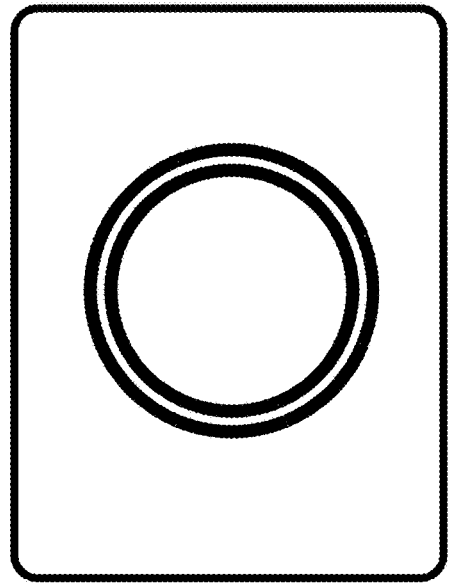
FIG. 33E
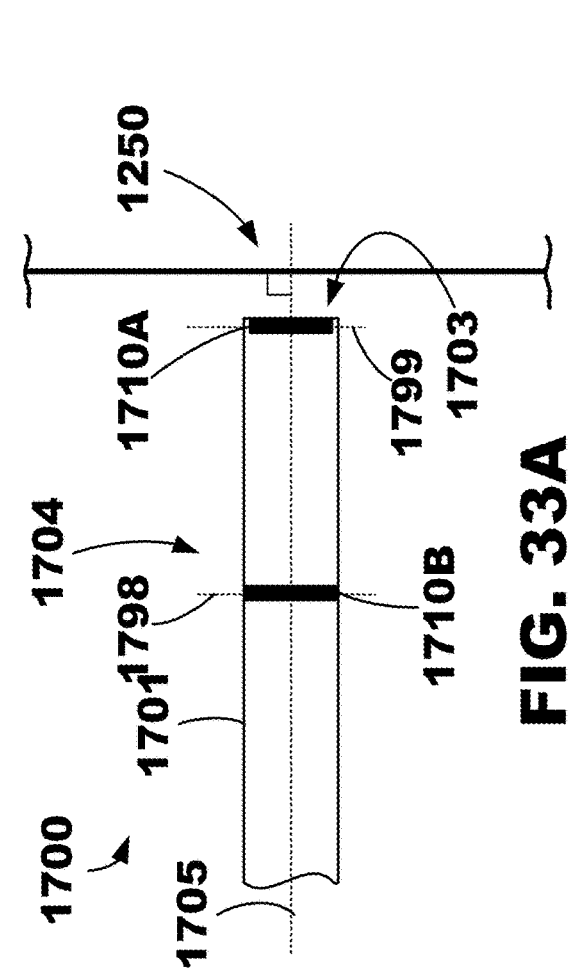
FIG. 33A
FIG. 33B
FIG. 33C
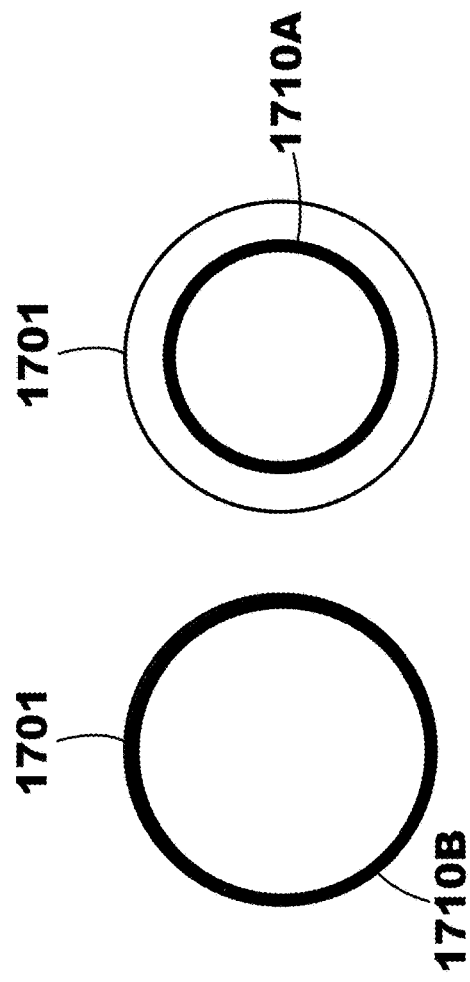

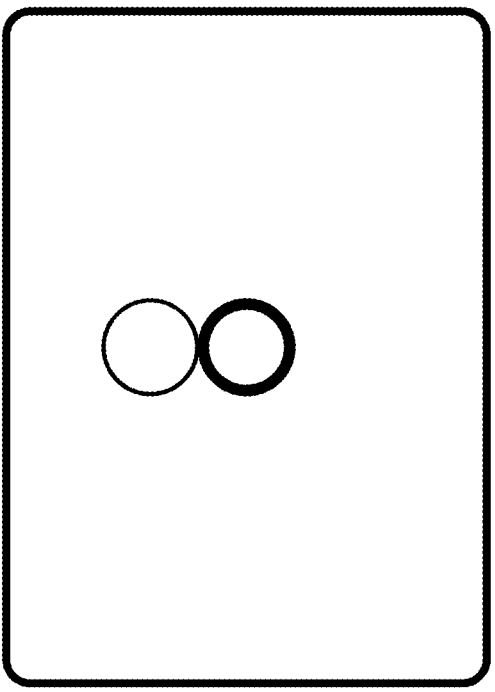
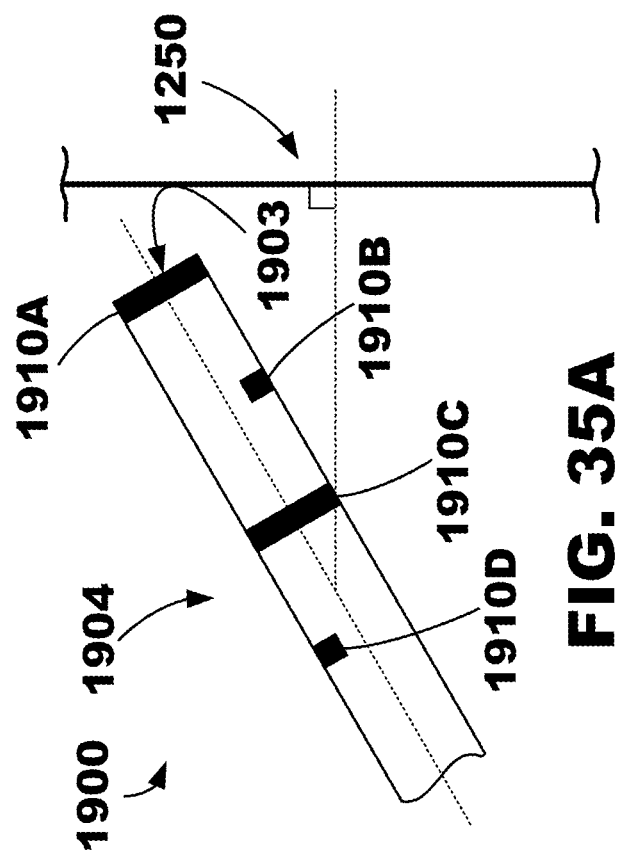

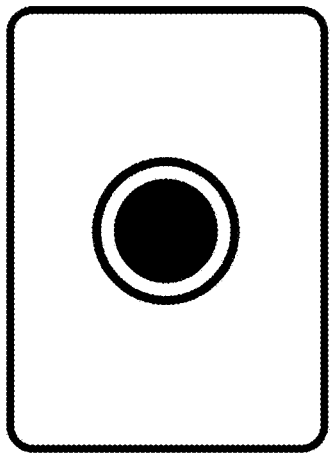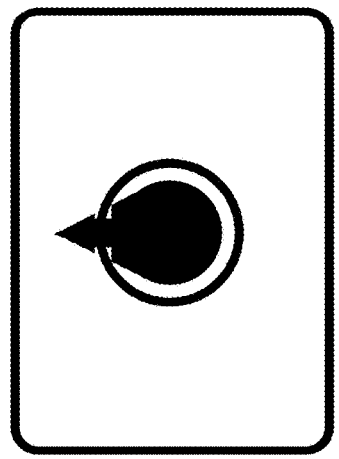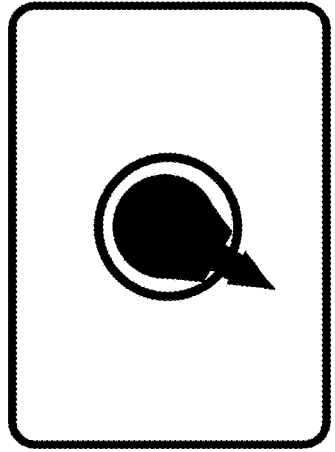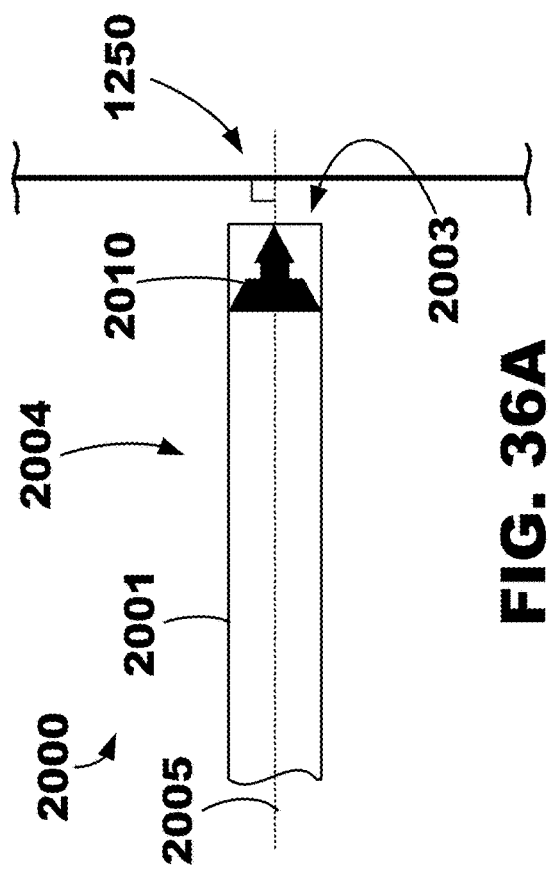

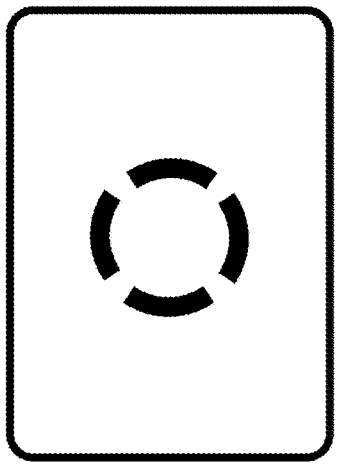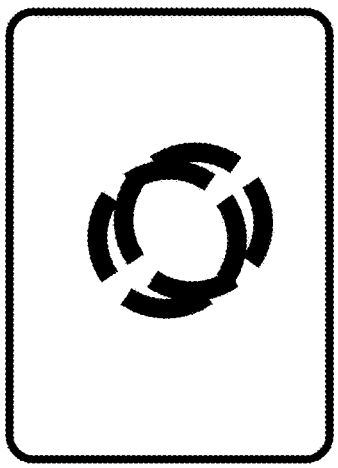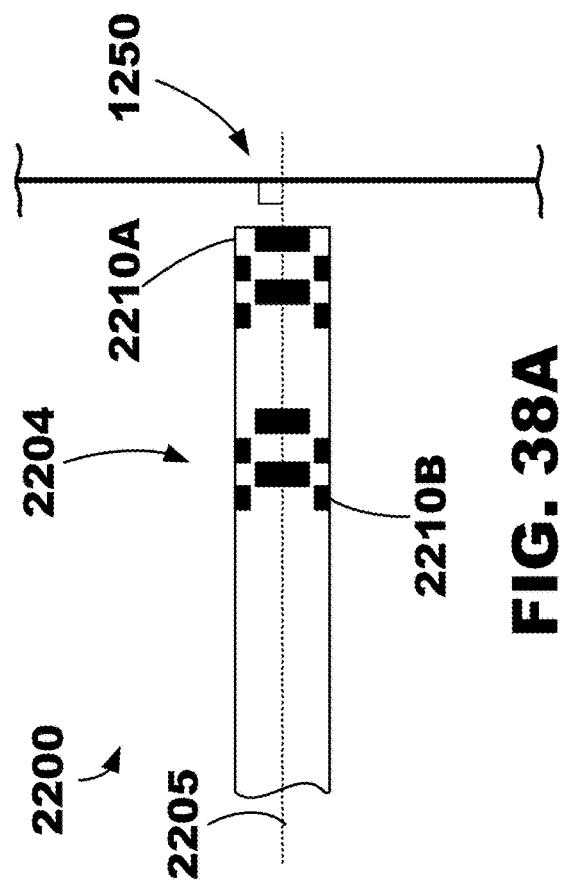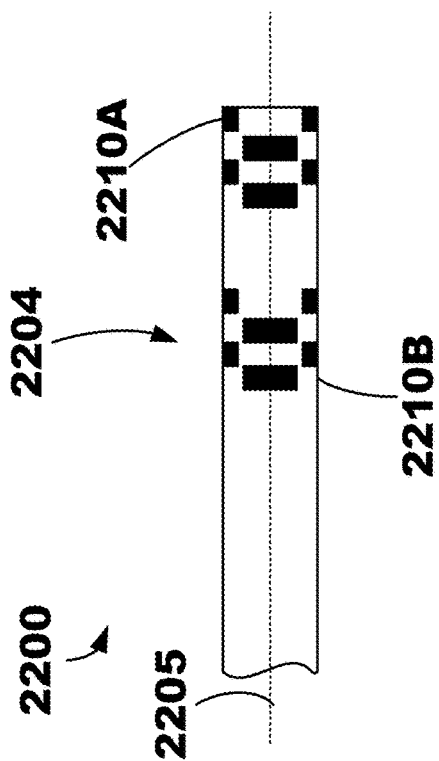

LEAD CONSTRUCTION INCLUDING ALIGNABLE MARKER ELEMENTS

This application claims the benefit of U.S. Provisional Patent Application 63/139,661 entitled "Lead Construction Including Alignable Marker Elements" and filed on Jan. 20, 2021, and U.S. Provisional Patent Application 63/139,662 entitled "Lead Construction" and filed on Jan. 20, 2021, each of which is incorporated herein by reference in its entirety.

This disclosure generally relates to medical devices and, in particular, additive manufacturing or 3D printing of medical devices, such as catheters and implantable stimulation leads, including alignable marker elements.

Medical catheters and leads are commonly used to access vascular and other locations within a body and to perform various functions at those locations, for example, delivery catheters may be used to deliver medical devices, such as implantable medical leads. A number of such medical devices are designed to be navigated through tortuous paths in a human body, such as through a patient's vasculature. Medical catheters and leads may be designed to be sufficiently flexible to move through turns, or curves, in the vasculature yet sufficiently stiff, or resilient, to be pushed through the vasculature. In many cases, such as those involving cardiovascular vessels, the route to the treatment or deployment site may be tortuous and may present conflicting design considerations that may require compromises between dimensions, flexibilities, material selection, operational controls, and the like. These contrasting properties can present challenges in designing and manufacturing catheters. Existing manufacturing processes, such as conventional extrusion, may also limit options in designing and manufacturing catheters.

Alignment of features of a catheter or delivery system in the body can be critical when deploying treatment to specific locations within the anatomy. Three-dimensional spatial orientation when navigating, delivering, and/or implanting an implantable apparatus (e.g., lead, catheter, or other implantable device) can be difficult while looking at imaging. For example, it is known that some implanters may believe that the implantable device (e.g., lead) they are implanting is located proximate the septum of the heart when, in reality, it is located proximate the free wall of the heart.

Cardiac resynchronization therapy (CRT) is an effective treatment for heart failure patients. CRT procedure involves simultaneous or different time pacing of the right ventricle (RV) and the left ventricle (LV). Implantation of the LV pacing lead is one of the determinants of CRT response. To obtain effective resynchronization, the final position of the LV pacing lead may target the latest activated areas of the left ventricle by placing the lead in the coronary sinus. However, positioning the LV lead may include several challenging technical issues and depends on the highly variable anatomy of the coronary vessels. Unfortunately, some patients are unable to receive CRT due to their venous anatomy being too small or difficult for the implanter to access with a lead (e.g., a lead may not be able to be navigated through the venous anatomy).

SUMMARY

The techniques of the present disclosure generally relate to additive manufacturing of medical devices, such as catheters and leads, that allows for further customization of the medical devices by providing an easier way to include components internal to the medical device. For example, the systems and techniques described herein may provide designing and printing an initial layer with internal spaces for components and then printing a finishing layer over, or on top of, the initial layer and components. These systems and techniques may allow for manufacturing more complex medical devices without increasing the complexity of manufacturing. Specifically, in one embodiment, the catheter may include internal grooves within which multiple lumen pull wires may be disposed. In another embodiment, the catheter may define an empty space for fluid travel during balloon inflation and may, e.g., include a bumped surface to help support the outer jacket.

The present disclosure further describes various multi-lumen and embedded components on a three-dimensionally (3D) printed or additively manufactured catheter, introducer, or implantable stimulation lead that provide a feature to be activated on the distal/proximal ends of the device while in vivo. The distal/proximal component(s) can aid in navigation, sensing, visualization, electrical stimulation, fixation, or be used to guide a secondary tool to a location. 3D printing with these features may allow such features to have more complexity than traditional manufacturing methods and can easily be combined with complex jacket shaping that cannot be achieved with current manufacturing methods.

Illustrative structures that may be manufactured or generated using the present disclosure may include lumens that are used for inflation, articulation, sensing, electrical or secondary tool components. Other processes to create catheters with multiple lumens are commonly shaped by reflowing extruded polymer over the components on a mandrel, which can lead to the catheter taking on the shape of the internal components with little control over the placement of internal components or the final jacket shape. When 3D printing, as described herein, the shaping of the jacket can be designed independently of the internal components and can be designed to focus on mechanical properties and anatomy interactions without impeding the function of the internal components. Further, internal features like those described in this disclosure can be combined with external features.

Additionally, it may be described that devices, such as catheters or leads, may be printed with embedded components without extrusion or reflow when using the methods and systems described herein. Because component placement can be done with precision and the 3D printing or additive manufacturing system may be described as being modular, tooling, code, etc. may be freely changed to add or remove a feature. Thus, preparing samples for a patient or in vivo testing can be greatly simplified. Further, it may be described that internal components can be embedded into a 3D printed device without impacting the outer jacket shape. Additionally, 3D printing may be described as "opening up" new cross sections and three-dimensional geometries that may not be able to be achieved with the existing manufacturing methods. Furthermore, these new shapes can be designed to be complementary with various internal embedded components.

One or more embodiments that may be formed or manufactured using the illustrative methods and systems described herein include a dual lumen unbraided tube made without an extruder, a dual lumen braided tube, a deflectable catheter with embedded pull-wire made without extrusion or reflow, and a lumen embedded into a raised geometry.

One illustrative implantable apparatus may include a body defining a distal end region extending along a distal end region axis and two or more alignable marker elements coupled to the body within the distal end region. Each of two or more alignable marker elements may define a complementary shape that complements the other alignable marker element(s) such that, when the distal end region is viewed axially, the two or more alignable marker elements form a fiducial shape indicative of acceptable alignment of the distal end region for positioning at a target site.

One illustrative additive manufacturing system may include one or more heating cartridges. Each heating cartridge may extend from a proximal side to a distal side and comprising a substrate inlet port at the proximal side and a substrate outlet port at the distal side and define an interior volume and a substrate channel extending through the interior volume from the proximal side to the distal side. Further, each heating cartridge defines a first filament port in fluid communication with the interior volume to receive a first filament. The system may further include a heating element thermally coupled to each heating cartridge of the one or more heating cartridges to heat the interior volume and a filament handling system comprising one or more motors to feed at least the first filament through the first filament port into the interior volume. The system may further include a substrate handling system comprising a head stock comprising a distal clamp to secure a distal portion of an elongate substrate, where the substrate is positioned to pass through the substrate channel when secured by the head stock, and one or more motors to translate or rotate one or both of the substrate when secured by the head stock and the heating cartridge relative to one another. The system may further include an intermediate component system positioned proximate the heating cartridge to position two or more alignable marker elements and a controller operably coupled to the heating element, one or more motors of the filament handling system, and one or more motors of the substrate handling system. The controller may be configured to control the one or more motors of the filament handling system to selectively control the feeding of the first filament into the interior volume, activate the heating element to melt any portion of the first filament in the interior volume, control one or more motors of the substrate handling system to move one or both of the substrate and the one or more heating cartridges relative to one another in at least a longitudinal direction to form a first elongate catheter jacket around the substrate, and control the intermediate component system to deposit the two or more alignable marker elements on the first elongate catheter jacket within a distal end region element such that, when the distal end region is viewed axially, the two or more alignable marker elements form a fiducial shape indicative of acceptable alignment of the distal end region for positioning at a target site.

One illustrative method for navigating an implantable apparatus in a patient's heart may include providing an implantable apparatus comprising a body defining a distal end region extending along a distal end region axis and two or more alignable marker elements coupled to the body within the distal end region, wherein each of the two or more alignable marker elements defines a complementary shape that complements the other alignable marker element(s) such that, when the distal end region is viewed axially, two or more alignable marker elements form a fiducial shape. The method may further include navigating the distal end region proximate a target site, generating an image taken perpendicular to the target site of the two or more alignable marker elements, and determining that the two or more alignable marker elements form the fiducial shape in the generated image indicating acceptable alignment of the distal end region.

One illustrative method of forming a lead may include providing a lead body extending from a proximal end region to a distal end region defining a lumen, where a conductor is positioned within the lumen, defining an opening through the lead body, extending the conductor outside of the lead body through the lumen, and positioning a C-shaped electrode proximate the conductor outside of the lead body. The method may further include electrically coupling C-shaped electrode to the conductor and mechanically coupling the C-shaped electrode onto the lead body.

One illustrative lead may include a lead body extending from a proximal end to a distal end and defining an S-shape region proximate the distal end, a first apex area within the S-shaped region and a second apex area within the S-shaped region. The lead may further include a first electrode positioned at the first apex area and a second electrode positioned at the second apex area.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 11 is a side view of an illustrative quadripolar lead that may be manufactured using the systems and methods described with respect FIGS. 1-6.

FIG. 12 is an expanded view of an illustrative electrode of the quadripolar lead of FIG. 11.

FIG. 21A depicts a side view of an acceptably aligned illustrative lead including two alignable marker elements being positioned proximate a target site.

FIG. 21B depicts an illustrative image of the lead of FIG. 21A taken perpendicular to the target site.

FIG. 22A depicts a side view of the illustrative lead of FIG. 21A in a less desirable alignment being positioned proximate the target site.

FIG. 22B depicts an illustrative image, taken perpendicular to the target site of FIG. 21A, where the lead is positioned and oriented as in FIG. 22A.

FIG. 24A depicts a side view of a desirably aligned illustrative lead including two alignable marker elements being positioned proximate a target site.

FIG. 24B depicts an illustrative image of the lead of FIG. 24A taken perpendicular to the target site.

FIG. 25A depicts a side view of the illustrative lead of FIG. 24A in a less desirable alignment being positioned proximate the target site.

FIG. 25B depicts an illustrative image, taken perpendicular to the target site of FIG. 24A, where the lead is positioned and oriented as in FIG. 25A.

FIG. 29A depicts a side view of an aligned illustrative lead including two alignable marker elements being positioned proximate a target site.

FIGS. 29B and 29C depict cross-sectional views of the lead of FIG. 29A.

FIG. 29D depicts an illustrative image, taken perpendicular to the target site of FIG. 29A, where the lead is positioned and oriented as shown in FIG. 29A.

FIGS. 29E and 29F depict illustrative images, taken perpendicular to the target site of FIG. 29A, where the lead is not positioned and oriented as intended.

FIG. 32A depicts a side view of an aligned illustrative lead including two alignable marker elements being positioned proximate a target site.

FIGS. 32B and 32C depict cross-sectional views of the lead of FIG. 32A.

FIG. 32D depicts an illustrative image, taken perpendicular to the target site of FIG. 32A, where the lead is positioned and oriented as shown in FIG. 32A.

FIG. 33A depicts a side view of an aligned illustrative lead including two alignable marker elements being positioned proximate a target site.

FIGS. 33B and 33C depict cross-sectional views of the lead of FIG. 33A.

FIG. 33D depicts an illustrative image, taken perpendicular to the target site of FIG. 33A, indicating that the lead is oriented towards the target site.

FIG. 33E depicts an illustrative image, taken perpendicular to the target site of FIG. 33A, indicating that the lead is oriented away from the target site.

FIG. 35A depicts a side view of an illustrative lead in an unintended and less desirable alignment being positioned proximate the target site.

FIG. 35B depicts an illustrative image, taken perpendicular to the target site of FIG. 35A, show the lead positioned and oriented as in FIG. 35A.

FIG. 36A depicts a side view of an aligned illustrative lead including a directionally indicative alignable marker element being positioned proximate a target site.

FIG. 36B depicts an illustrative image, taken perpendicular to the target site of FIG. 36A, where the lead is positioned and oriented as shown in FIG. 36A.

FIGS. 36C and 36D depict illustrative images, taken perpendicular to the target site of FIG. 36A, where the lead is not positioned and oriented as intended.

FIGS. 38A and 38B depict side views of an aligned illustrative lead including a plurality of alignable marker elements being positioned proximate a target site.

FIG. 38C depicts an illustrative image, taken perpendicular to the target site of FIG. 38A, where the lead is positioned and oriented as shown in FIG. 39A.

FIG. 38D depicts an illustrative image, taken perpendicular to the target site of FIG. 38A, where the lead is not positioned and oriented as intended.

DETAILED DESCRIPTION

Figure 1:
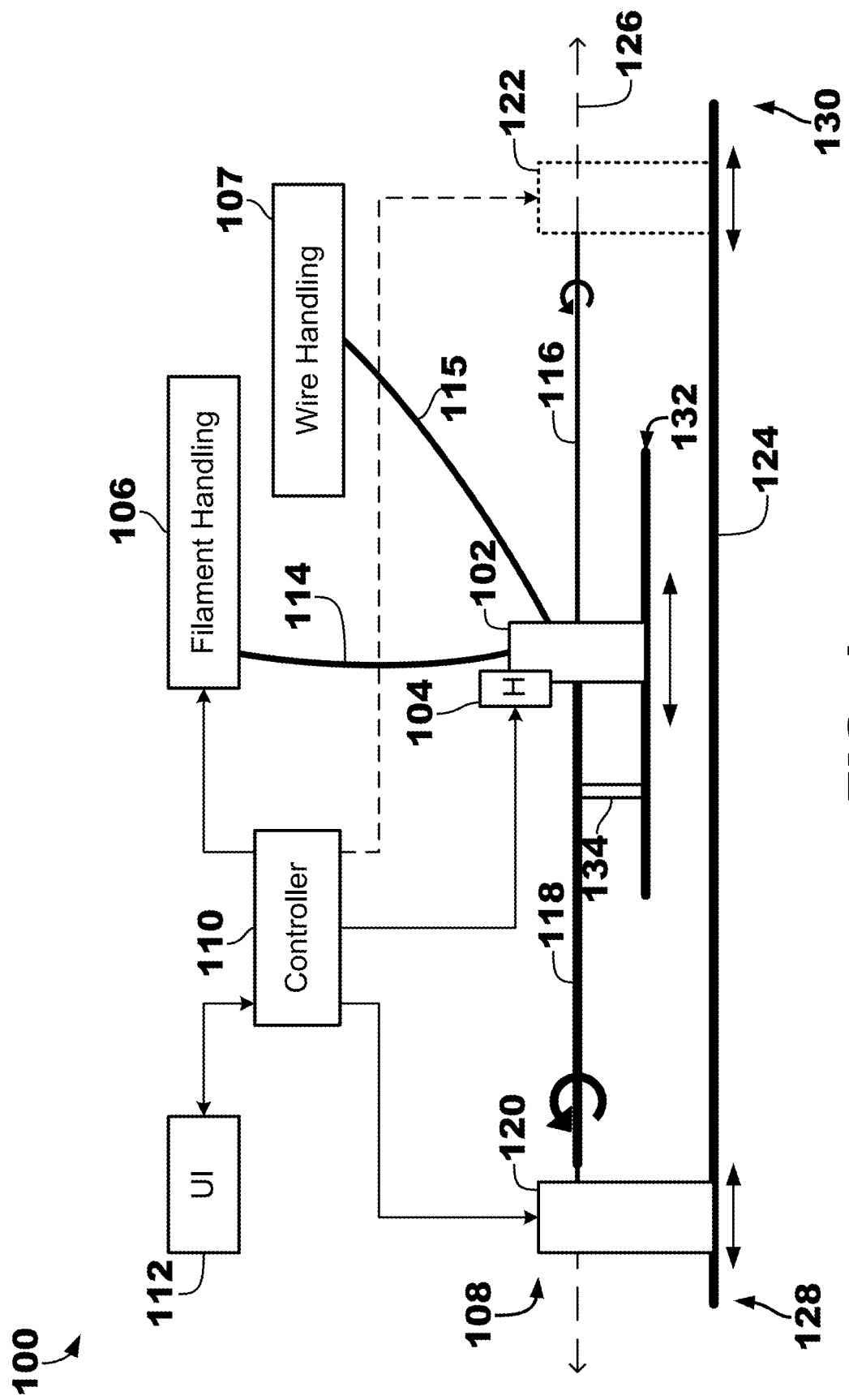
FIG. 1 is a conceptual diagram of an illustrative additive manufacturing system according to the present disclosure.

The present disclosure generally provides additive manufacturing systems and methods for medical devices, such as catheters and leads, that allows for providing more than one jacket or layer laid down to form the medical device. For example, one or more layers (e.g., an initial jacket or layer) may define shapes or structures within which internal components may be positioned and subsequent layers or jackets may cover or embed the internal components. The internal shapes and components included may be dictated by desirable functional characteristics or properties of the medical device. Specifically, components or empty space may be included on top of an initial print of filament material (e.g., a first layer or jacket) and a subsequent layer or jacket of filament material may be printed thereon. The printing may be done in multiple stages or as a part of a co-print with multiple printing head and tools, as described herein. Additionally, the present disclosure includes a method of coupling an electrode to a lead, various lead shapes and orientations, and leads including alignable marker elements, each of which may be facilitated using the additive manufacturing systems and methods described herein.

As used herein, the term "or" refers to an inclusive definition, for example, to mean "and/or" unless its context of usage clearly dictates otherwise. The term "and/or" refers to one or all of the listed elements or a combination of at least two of the listed elements.

As used herein, the phrases "at least one of" and "one or more of" followed by a list of elements refers to one or more of any of the elements listed or any combination of one or more of the elements listed.

As used herein, the terms "coupled" or "connected" refer to at least two elements being attached to each other either directly or indirectly. An indirect coupling may include one or more other elements between the at least two elements being attached. Either term may be modified by "operatively" and "operably," which may be used interchangeably, to describe that the coupling or connection is configured to allow the components to interact to carry out described or otherwise known functionality. For example, a controller may be operably coupled to a resistive heating element to allow the controller to provide an electrical current to the heating element.

As used herein, any term related to position or orientation, such as "proximal," "distal," "end," "outer," "inner," and the like, refers to a relative position and does not limit the absolute orientation of an embodiment unless its context of usage clearly dictates otherwise.

All scientific and technical terms used herein have meanings commonly used in the art unless otherwise specified. The definitions provided herein are to facilitate understanding of certain terms used frequently herein and are not meant to limit the scope of the present disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows one example of an additive manufacturing system 100 according to the present disclosure. The system 100 may be configured and used to produce a catheter, catheter component, lead, or subassembly. The system 100 may use or include consumable filament materials or pellet form resins having a wide variety of hardness levels. The system 100 may be configured to operate a wide variety of process conditions to produce catheters, catheter components, leads, or subassemblies using filaments or pellet form resins of various hardness levels. In general, the system 100 defines a distal region 128, or distal end, and a proximal region 130, or proximal end. The system 100 may include a platform 124 including a rigid frame to support one or more components of the system.

Further components of the system 100 and methods of use may be described in U.S. patent application Ser. No. 17/081,815, entitled "Additive Manufacturing for Medical Devices" filed on Oct. 27, 2020, U.S. Prov. Pat. App. Ser. No. 63/001,832 entitled "3D Printed Splines on Medical Devices and Methods to Manufacture the Same" filed on Mar. 30, 2020, U.S. Prov. Pat. App. Ser. No. 63/059,867, entitled "Systems and Methods for Manufacturing 3D Printed Medical Devices" filed on Jul. 31, 2020, U.S. Prov. Pat. App. Ser. No. 63/059,890, entitled "Systems and Methods for Manufacturing 3D Printed Medical Devices" filed on Jul. 31, 2020, U.S. Prov. Pat. App. Ser. No. 63/059,870, entitled "3D Printed Medical Devices Including Internal Shaping" filed on Jul. 31, 2020, and U.S. Prov. Pat. App. Ser. No. 63/130, 321, entitled "Medical Devices with Multi-plane Articulation" filed on Dec. 23, 2020, each of which are herein incorporated by reference in their entireties. For example, as shown in the illustrated embodiment, the system 100 may include one or more components, such as a heating cartridge 102, a heating element 104, a filament handling system 106, an optional wire handling system 107, a substrate handling system 108, a controller 110, and a user interface 112. The filament handling system 106 may be operably coupled to the heating cartridge 102. The filament handling system 106 may provide one or more filaments 114 to the heating cartridge 102. The optional wire handling system 107 may be used to provide one or more wires 115 to the heating cartridge 102. The heating element 104 may be operably coupled, or thermally coupled, to the heating cartridge 102. The heating element 104 may provide heat to melt filament material in the heating cartridge 102 from the one or more filaments 114 provided by the filament handling system 106. The optional wires 115 may not be melted by the heating cartridge 102. The substrate handling system 108 may be operably coupled to the heating cartridge 102. The substrate handling system 108 may provide a substrate 116 that extends through the heating cartridge. Melted filament material located in the heating cartridge 102 may be applied to the substrate 116. The substrate 116 or the heating cartridge 102 may be translated or rotated relative to one another by the substrate handling system 108. The substrate handling system 108 may be used to move the substrate 116 or the heating cartridge 102 relative to one another to cover the substrate 116 with the melted filament material to form a jacket 118. The optional wires 115 may be incorporated into the jacket 118 (e.g., molded into, bedded within, etc.).

The substrate 116 may also be described as a mandrel or rod. The jacket 118 may be formed or deposited around the substrate 116. In some embodiments, the jacket 118 may be formed concentrically around the substrate 116. In one example, the jacket 118 is formed concentrically and centered around the substrate 116.

Figure 6:
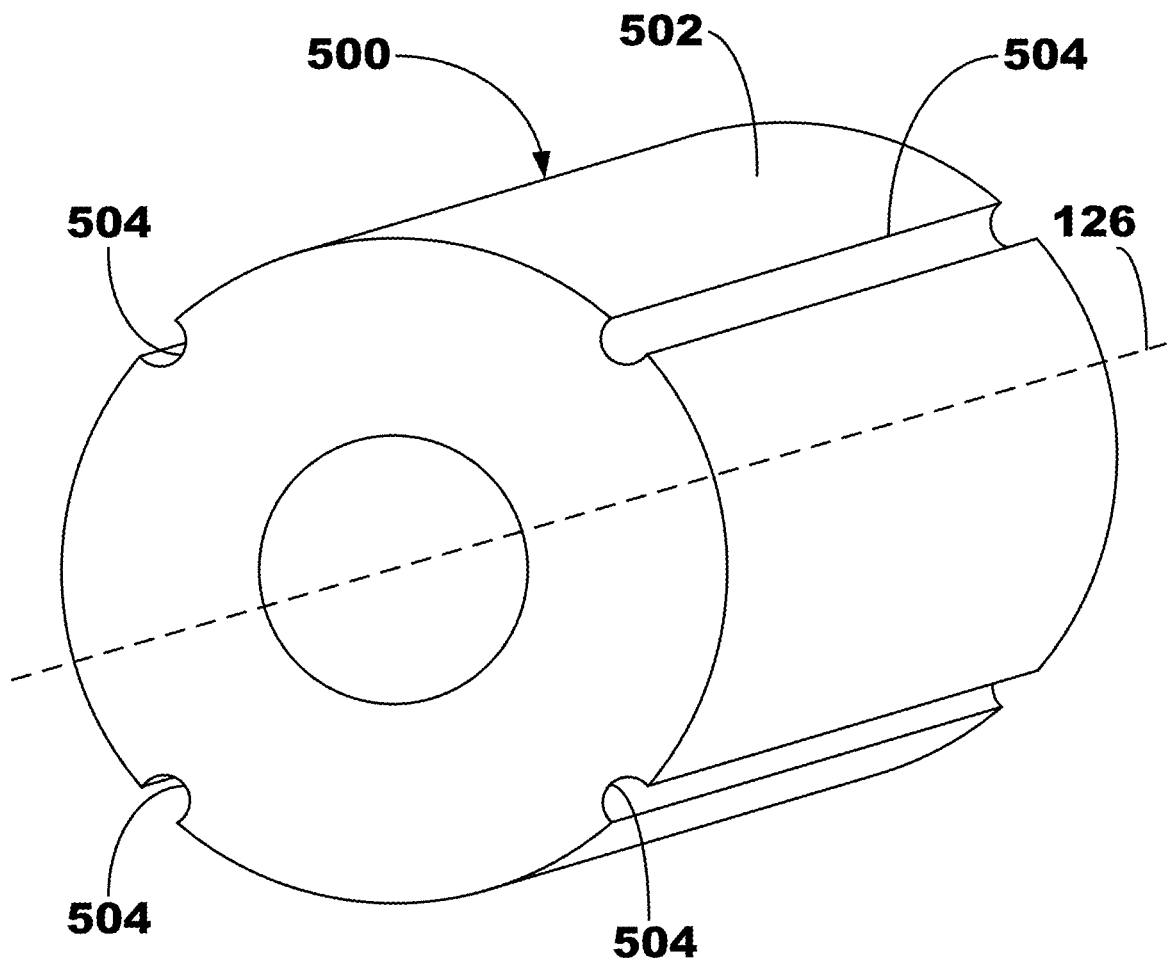
FIG. 6 is a conceptual diagram of an illustrative catheter jacket having a first jacket and cutouts that may be manufactured using the additive manufacturing system of FIG. 1.

When the system 100 is used to make a catheter or catheter component, the jacket 118 may be described as a catheter jacket. Some or all of the substrate 116 may be removed or separated from the jacket 118 and the remaining structure coupled to the jacket may form the catheter or catheter component, such as a sheath. One example of a catheter that may be formed by the system 100 is shown in FIG. 6.

The substrate 116 may be formed of any suitable material capable of allowing melted filament material to be formed thereon. In some embodiments, the substrate 116 is formed of a material that melts at a higher temperature than any of the filaments 114. One example of a material that may be used to form the substrate 116 includes stainless steel.

The controller 110 may be operably coupled to one or more of the heating element 104, the filament handling system 106, the substrate handling system 108, and the user interface 112. The controller 110 may activate, or initiate or otherwise "turn on," the heating element 104 to provide heat to the heating cartridge 102 to melt the filament material located therein. Further, the controller 110 may control or command one or more motors or actuators of various portions of the system 100. Furthermore, the controller 110 may control one or more motors or actuators the filament handling system 106 to provide one or more filaments 114. Further, the controller 110 may control one or more motors or actuators of the substrate handling system 108 to move one or both of the heating cartridge 102 or the substrate 116 relative to one another. Further still, the controller 110 may send or receive data to the user interface 112, for example, to display information or to receive user commands. Control of the components operably coupled to the controller 110 may be determined based on user commands received by the user interface 112. In some embodiments, the user commands may be provided in the form of a machine-readable code or coding language.

Any suitable implementation may be used to provide the substrate handling system 108. In some embodiments, the substrate handling system 108 may include one or more of a head stock 120, an optional tail stock 122, and one or more motors coupled to or included in the head stock or tail stock. One or both of the head stock 120 and the tail stock 122 may be coupled to the platform 124. A stock may be defined as a structure that holds or secures the substrate 116 during formation of the jacket 118. The head stock 120 is defined as the stock closest to the end of the substrate 116 where formation of the jacket 118 begins in the formation process. In the illustrated embodiment, the jacket 118 is shown proximal to the head stock 120 and distal to the heating cartridge 102.

When the substrate 116 is secured by one or both stocks 120, 122, the substrate is generally positioned to pass through a substrate channel defined by the heating cartridge 102. One or both stocks 120, 122 may include a clamp or other securing mechanism to selectively hold the substrate 116. Such a clamp may be operably coupled to a substrate motor. In some embodiments, the substrate motor may be used to control opening and closing of the clamp. In some embodiments, the substrate motor may be used to rotate the substrate 116 in a clockwise or counterclockwise direction about a longitudinal axis 126. A translation motor may be operably coupled between a stock 120, 122 and the platform 124. In some embodiments, the translation motor may be used to translate the stock 120, 122 in a longitudinal direction along the longitudinal axis 126. In some embodiments, the translation motor also may be used to translate the stock 120, 122 in a lateral direction different than the longitudinal axis 126. The lateral direction may be oriented substantially orthogonal, or perpendicular, to the longitudinal axis 126.

In some embodiments, the substrate handling system 108 may be configured to move the head stock 120 at least in a longitudinal direction (for example, parallel to the longitudinal axis 126) relative to the platform 124. The substrate 116 may be fed through the substrate channel of the heating cartridge 102 by movement of the head stock 120 relative to the platform 124. A distal portion of the substrate 116 may be clamped into the head stock 120. The head stock 120 may be positioned close to the heating cartridge 102 at the beginning of the jacket formation process. The head stock 120 may move distally away from the heating cartridge 102, for example in a direction parallel to the longitudinal axis 126. In other words, the head stock 120 may move toward the distal region 128 of the system 100 while pulling the secured substrate 116 through the heating cartridge 102. As the substrate 116 passes through the heating cartridge 102, melted filament material from the filament 114 may be formed or deposited onto the substrate 116 to form the jacket 118. The heating cartridge 102 may be stationary relative to the platform 124. In some embodiments, the tail stock 122 may be omitted.

In some embodiments, the substrate handling system 108 may be configured to move the heating cartridge 102 at least in a longitudinal direction (along the longitudinal axis 126) relative to the platform 124. The substrate 116 may be fed through the substrate channel of the heating cartridge 102. A distal portion of the substrate 116 may be clamped into the head stock 120. A proximal portion of the substrate 116 may be clamped into the tail stock 122. In one example, the heating cartridge 102 may be positioned relatively close to the head stock 120 at the beginning of the jacket formation process. The heating cartridge 102 may move proximally away from the head stock 120. The heating cartridge 102 may move toward the proximal region 130 of the system 100. As the heating cartridge 102 passes over the substrate 116, melted filament material may be deposited onto the substrate 116 to form a jacket. The head stock 120 and the tail stock 122 may be stationary relative to the platform 124. In another example, the heating cartridge 102 may start near the tail stock 122 and move toward the distal region 128.

One or more motors of the substrate handling system 108 may be used to rotate one or both of the substrate 116 and the heating cartridge 102 relative to one another. In some embodiments, only the substrate 116 may be rotated about the longitudinal axis 126. In some embodiments, only the heating cartridge 102 may be rotated about the longitudinal axis 126. In some embodiments, both the substrate 116 and the heating cartridge 102 may be rotated about the longitudinal axis 126.

The heating cartridge 102 may be part of a subassembly 132. The subassembly 132 may be coupled to the platform 124. In some embodiments, one or more motors of the substrate handling system 108 may be coupled between subassembly 132 and the platform 124 to translate or rotate the subassembly 132, including the heating cartridge 102, relative to the platform 124 or the substrate 116. In some embodiments, one or more motors of the substrate handling system 108 may be coupled between a frame of the subassembly 132 and the heating cartridge 102 to translate or rotate the heating cartridge relative to the platform 124.

In some embodiments, the substrate 116 may be rotated about the longitudinal axis 126 relative to the heating cartridge 102 to facilitate forming certain structures of the jacket. In one example, the substrate 116 may be rotated by one or both of the head stock 120 and the tail stock 122 of the substrate handling system 108. In another example, the heating cartridge 102 or subassembly 132 may be rotated by the substrate handling system 108.

The system 100 may include one or more concentricity guides 134. The concentricity guide 134 may facilitate adjustments to the concentricity of the jacket around the substrate 116 before or after the substrate passes through the heating cartridge 102. The concentricity guide 134 may be longitudinally spaced from the heating cartridge 102. In some embodiments, the spacing may be greater than or equal to 1, 2, 3, 4, or 5 cm. The spacing may be sufficient to allow the jacket 118 to cool down and no longer be deformable. In some embodiments, one or more concentricity guides 134 may be positioned distal to the heating cartridge 102 and to engage the jacket 118. In some embodiments, one or more concentricity guides 134 may be positioned proximal to the heating cartridge 102 to engage the substrate 116. The concentricity guide 134 may mitigate drooping of the substrate 116 and may mitigate susceptibility to eccentricity in the alignment of the stock 120, 122 and the heating cartridge 102.

Any suitable implementation may be used to provide the filament handling system 106. One or more filaments 114 may be loaded into the filament handling system 106. For example, filaments 114 may be provided in the form of wound coils. Filaments 114 may be fed to the heating cartridge 102 by the filament handling system 106. In some embodiments, the filament handling system 106 may include one, two, or more pinch rollers to engage the one or more filaments 114. In some embodiments, the filament handling system 106 may include one or more motors. The one or more motors may be coupled to the one or more pinch rollers to control rotation of the pinch rollers. The force exerted by the motors onto the pinch rollers and thus onto the one or more filaments 114 may be controlled by the controller 110.

In some embodiments, the filament handling system 106 may be configured to feed the filaments 114 including at least a first filament and a second filament. The jacket 118 may be formed from the material of one or both of the filaments 114. The filament handling system 106 may be capable of selectively feeding the first filament and the second filament. For example, one motor may feed the first filament and another motor may feed the second filament. Each of the motors may be independently controlled by the controller 110. Selective, or independent, control of the feeds may allow for the same or different feed forces to be applied to each of the filaments 114.

The filaments 114 may be made of any suitable material, such as polyethylene, PEBAX elastomer (commercially available from Arkema S.A. of Colombes, France), nylon 12, polyurethane, polyester, liquid silicone rubber (LSR), or PTFE.

The filaments 114 may have any suitable Shore durometer. In some embodiments, the filaments 114 may have, or define, a Shore durometer suitable for use in a catheter. In some embodiments, the filaments 114 have a Shore durometer of at least 25 A and up to 90 A. In some embodiments, the filaments 114 have a Shore durometer of at least 25 D and up to 80 D.

In some embodiments, the filament handling system 106 may provide a soft filament as one of the filaments 114. In some embodiments, a soft filament may have a Shore durometer less than or equal to 90 A, 80 A, 70 A, 80 D, 72 D, 70 D, 60 D, 50 D, 40 D, or 35 D.

In some embodiments, the filament handling system 106 may provide a hard filament and a soft filament having a Shore durometer less than the soft filament. In some embodiments, the soft filament has a Shore durometer that is 10 D, 20 D, 30 D, 35 D, or 40 D less than a Shore durometer of the hard filament.

The system 100 may be configured to provide a jacket 118 between the Shore durometers of a hard filament and a soft filament. In some embodiments, the filament handling system 106 may provide a hard filament having a Shore durometer equal to 72 D and a soft filament having a Shore durometer equal to 35 D. The system 100 may be capable of providing a jacket 118 having a Shore durometer that is equal to or greater than 35 D and less than or equal to 72 D.

The system 100 may be configured to provide a jacket 118 having, or defining, segments with different Shore durometers. In some embodiments, the system 100 may be capable of providing a jacket 118 having one or more of a 35 D segment, a 40 D segment, 55 D segment, and a 72 D segment.

The filaments 114 may have any suitable width or diameter. In some embodiments, the filaments 114 have a width or diameter of 1.75 mm. In some embodiments, the filaments 114 have a width or diameter of less than or equal to 1.75, 1.5, 1.25, 1, 0.75, or 0.5 mm.

Segments may have uniform or non-uniform Shore durometers. The system 100 may be configured to provide jacket 118 having one or more segments with non-uniform Shore durometers. In some embodiments, the jacket 118 may include continuous transitions between at least two different Shore durometers, for example, as shown in FIG. 6.

The controller 110 may be configured to change a feeding force applied to one or more of the filaments 114 to change a ratio of material in the jacket over a longitudinal distance. By varying the feeding force, the system 100 may provide different Shore durometer segments in a jacket 118, whether uniform or non-uniform. In one example, sharp transitions between uniform segments may be provided by stopping or slowing longitudinal movement while continuously, or discretely with a large step, changing the feeding force of one filament relative to another filament of the substrate 116 relative to the heating cartridge 102. In another example, gradual transitions between segments may be provided by continuously, or discretely with small steps, changing the feeding force of one filament relative to another filament while longitudinally moving the substrate 116 relative to the heating cartridge 102.

The one or more wires 115 provided by the wire handling system 107 may be introduced in any suitable manner. In some embodiments, the wires 115 may be attached to the substrate 116 and pulled by movement of the substrate. One example of a wire is a pull wire that may be used to steer the catheter produced by the system 100. In some embodiments, a particularly shaped heating cartridge may be used to accommodate one or more wires 115.

Any suitable type of heating element 104 may be used. In some embodiments, the heating element 104 may be a resistive-type heating element, which may provide heat in response to an electrical current. Other types of heating elements that may be used for the heating element 104 include a radio frequency (RF) or ultrasonic-type heating element. The heating element 104 may be capable of providing heat sufficient to melt the filaments 114. In some embodiments, the heating element 104 may heat the filaments 114 to greater than or equal to 235, 240, 250, or 260 degrees Celsius. In general, the one or more heating elements 104 may be used to heat the filaments 114 to any suitable melting temperature known to one of ordinary skill in the art having the benefit of this disclosure.

Figure 2:
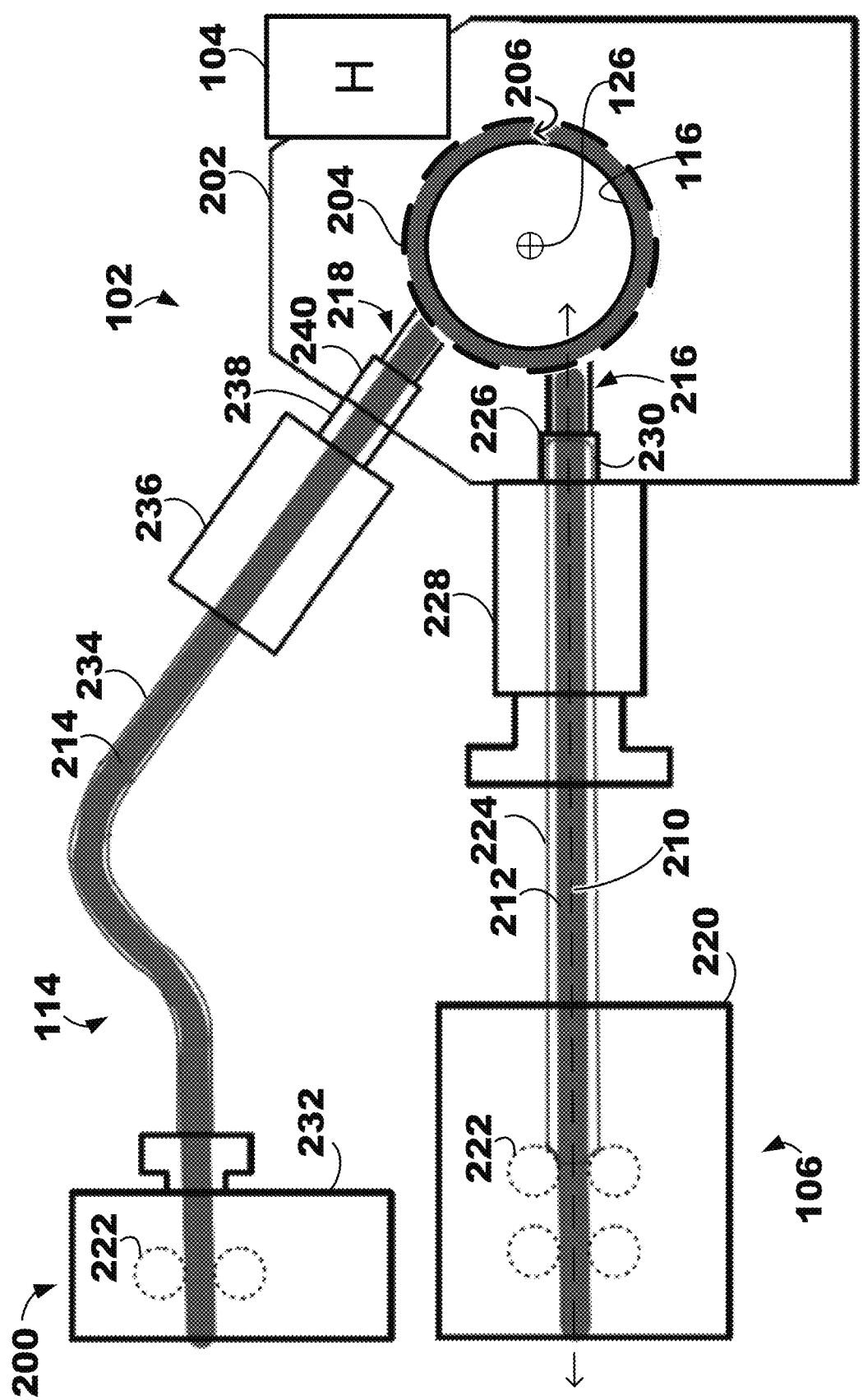
FIG. 2 is a conceptual diagram of an illustrative additive manufacturing apparatus for use with, for example, the additive manufacturing system of FIG. 1.

FIG. 2 shows one example of an additive manufacturing apparatus 200 of the additive manufacturing system 100 in an end view along the longitudinal axis 126, which is illustrated as a circle and cross. More detail of some components of the additive manufacturing system 100 are shown, such as the heating cartridge 102 and the filament handling system 106.

The heating cartridge 102 may include a heating block 202 at least partially defining an interior volume 204. The interior volume 204 may be heated by the heating element 104. The heating element 104 may be thermally coupled to the heating block 202 to melt filament material in the interior volume 204. In general, the system 100 may be configured to melt any portion of the filaments 114 in the interior volume 204. The heating element 104 may be disposed in an exposed or exterior volume defined in the heating block 202. The heating element 104 may be positioned proximate to or adjacent to the interior volume 204. In some embodiments, one, two, three, or more heating elements 104 may be thermally coupled to the heating block 202.

The heating block 202 may allow the substrate 116, which may be an elongate substrate or member, to pass through the heating block. The substrate 116 may be able to extend, or pass, through the interior volume 204. The substrate channel 206 defined by the heating cartridge 102 may extend through the interior volume 204. The substrate channel 206 may extend in a same or similar direction as the substrate 116. The substrate channel 206 may extend along the longitudinal axis 126.

A width or diameter of the interior volume 204 is larger than a width or diameter of the substrate 116. The width or diameter of the interior volume 204 or the substrate 116 is defined in a lateral direction, which may be orthogonal to the longitudinal axis 126. In one example, the lateral direction may be defined along a lateral axis 210. In some embodiments, the clearance between the substrate 116 and interior volume 204 is relatively small to facilitate changes in composition of filament material used to form the jacket 118 (FIG. 1) around the substrate 116.

The portion of the interior volume 204 around the substrate 116 may receive a flow of melted filament material from the filaments 114. When more than one filament material is provided to the interior volume 204, the filament materials may flow and blend, or mix, around the substrate 116.

In the illustrated embodiment, the filaments 114 includes a first filament 212 and a second filament 214. The first filament 212 may be provided into the interior volume 204 through a first filament port 216 at least partially defined by the heating block 202. The second filament 214 may be provided into the interior volume 204 through a second filament port 218 at least partially defined by the heating block 202. Each filament port 216, 218 may be at least partially defined by the heating block 202. Each filament port 216, 218 may be in fluid communication with the interior volume 204.

The filaments 114 may be delivered to the interior volume 204 in the same or different manners. In the illustrated embodiment, the first filament 212 is delivered to the interior volume 204 in a different manner than the second filament 214.

The filament handling system 106 may include a first handling subassembly 220. The first handling subassembly 220 may deliver the first filament 212 to the interior volume 204. The first handling subassembly 220 may include one or more pinch rollers 222. Each of the one or more pinch rollers 222 may be operably coupled to a motor. Any suitable number of pinch rollers 222 may be used. As illustrated, the first handling subassembly 220 may include two sets of pinch rollers 222. Pinch rollers 222 may be used to apply a motive force to the first filament 212 to move the first filament, for example, toward the interior volume 204.

The heating cartridge 102 may include a first guide sheath 224. The first guide sheath 224 may extend between the filament handling system 106 and the interior volume 204. The first guide sheath 224 may be coupled to the heating block 202. The first guide sheath 224 may extend into the first filament port 216 from an exterior of the heating block 202. The first guide sheath 224 may define a lumen in fluid communication with the interior volume 204. An inner width or diameter of the lumen may be defined to be greater than a width or diameter of the first filament 212. The first filament 212 may extend through the first guide sheath 224 from the pinch rollers 222 of the first handling subassembly 220 to the first filament port 216 and extend distally past the first guide sheath 224 into the interior volume 204.

As used herein with respect to the filaments 114, the term "distal" refers to a direction closer to the interior volume 204 and the term "proximal" refers to a direction closer to the filament handling system 106.

In some embodiments, a proximal end of the first guide sheath 224 may terminate proximate to one of the pinch rollers 222. A distal end of the first guide sheath 224 may terminate at a shoulder 226 defined by the first filament port 216. A distal portion or distal end of the first guide sheath 224 may be positioned proximate to or adjacent to the interior volume 204.

The inner width or diameter of the lumen of the first guide sheath 224 may be defined to be substantially the same or equal to an inner width or diameter of the first filament port 216, such as a smallest inner width or diameter of the first filament port. In other words, an inner surface of the first guide sheath 224 may be flush with an inner surface of the first filament port 216.

In some embodiments, the heating cartridge 102 may include a support element 228. The support element 228 may be coupled to the first guide sheath 224. The first guide sheath 224 may extend through a lumen defined by the support element 228. The support element 228 may be proximate to the heating block 202. In the illustrated embodiment, the support element 228 is coupled to the heating block 202. The support element 228 may include a coupling protrusion configured to be mechanically coupled to a coupling receptacle 230 defined by the first filament port 216. In some embodiments, the coupling receptacle 230 may define threads and the coupling protrusion of the support element 228 may define complementary threads.

The coupling receptacle 230 may terminate at the shoulder 226 of the first filament port 216. The coupling protrusion of the support element 228 may be designed to terminate at the shoulder 226. In some embodiments, a distal end of the support element 228 and the distal end of the first guide sheath 224 may engage the shoulder 226. In other embodiments, the distal end of the support element 228 may engage the shoulder 226 and the distal end of the first guide sheath 224 may engage a second shoulder (not shown) defined by the first filament port 216 distal to the shoulder 226.

When the first filament port 216 defines one shoulder, the first filament port 216 may define at least two different inner widths or diameters. The larger inner width or diameter may be sized to thread the support element 228 and the smaller inner width or diameter may be sized to match the inner width or diameter of the first guide sheath 224.

When the second filament port 218 defines two shoulders, the first filament port 216 may define at least three different inner widths or diameters. The largest inner width or diameter may be sized to thread the support element 228. The intermediate inner width or diameter may be sized to receive a distal portion of the first guide sheath 224. The smallest inner width or diameter may be sized to match the inner width or diameter of the first guide sheath 224.

The filament handling system 106 may include a second handling subassembly 232. The second handling subassembly 232 may deliver the second filament 214 to the interior volume 204. The second handling subassembly 232 may include one or more pinch rollers 222. Each of the one or more pinch rollers 222 may be operably coupled to a motor. Any suitable number of pinch rollers 222 may be used. As illustrated, the second handling subassembly 232 may include one set of pinch rollers 222. Pinch rollers 222 may be used to apply a motive force to the second filament 214.

The heating cartridge 102 may include one or more of a second guide sheath 234, a heat sink 236, and a heat break 238. The second guide sheath 234 may extend at least between the second handling subassembly 232 and the heat sink 236. The second guide sheath 234 may be coupled to the heat sink. The second guide sheath 234 may be coupled to the second handling subassembly 232. The heat sink 236 may be coupled to the heat break 238. The heat break 238 may be coupled to the heat block 202. The heat break 238 may extend into the second filament port 218 from an exterior of the heating block 202.

The second guide sheath 234 may define a lumen in fluid communication with the interior volume 204. The second filament 214 may extend through the second guide sheath 234 from the second handling subassembly 232 to the heat sink 236, through the heat sink 236, through the heat break, and through the second filament port 218. In some embodiments, the second guide sheath 234 may extend to the pinch rollers 222 in the second handling subassembly 232. In some embodiments, the second guide sheath 234 may extend at least partially into the heat sink 236.

The heat break 238 may be proximate to the heating block 202. The heat break 238 may be positioned between the heat sink 236 and the heating block 202. The heat break 238 may include a coupling protrusion configured to mechanically couple to a coupling receptacle 240 defined by the second filament port 218. In some embodiments, the coupling receptacle 240 may define threads and the coupling protrusion of the heat break 238 may define complementary threads. The second filament port 218 may include one or more shoulders such as those described with respect to the first filament port 216, except that the second filament port 218 may not be configured to receive the second guide sheath 234. The inner width or diameter of the support element 228 may be larger than the inner width or diameter of the heat break 238, for example, to accommodate the outer width or diameter of the first guide sheath 224. In other embodiments, the second filament port 218 may be configured to receive the second guide sheath 234 in a similar manner to the first filament port 216 receiving the first guide sheath 224.

Any suitable material may be used to make the guide sheaths 224, 234. In some embodiments, one or both guide sheaths 224, 234 may include a synthetic fluoropolymer. One or both guide sheaths 224, 234 may include polytetrafluoroethylene (PTFE). Another suitable material may include an ultra-high molecular weight polyethylene (UHMWPE).

Any suitable material may be used to make the support element 228. In some embodiments, the support element 228 may be a thermal insulator. The support element 228 may include a thermoplastic. The support element 228 may be made of a polyamide-imide, such as a TORLON polyamide-imide (commercially available from McMaster-Carr Supply Co. of Elmhurst, Illinois). Other suitable materials may include liquid-crystal polymer, polyaryletherketone (PAEK), polyphenylene sulfide, and polysulfone.

The support element 228 may provide mechanical support to the first guide sheath 224. The support element 228 may include a substantially rigid material. In some embodiments, the support element 228 include a material having a higher durometer than material used to make the first guide sheath 224.

Any suitable material may be used to make the heat sink 236. The heat sink 236 may include a high thermal conductivity material. In some embodiments, the heat sink 236 includes aluminum.

Any suitable material may be used to make the heat break 238. The heat break 238 may include a low thermal conductivity material. In some embodiments, the heat break 238 includes titanium. The heat break 238 may include a necked portion to reduce the amount of material between a proximal portion and a distal portion of the heat break. The necked portion may facilitate a reduced thermal conductivity between the proximal portion and the distal portion of the heat break 238.

In general, use of the apparatus 200 may facilitate using softer filaments at high feed forces and pressures, which tend to compress the soft filament and may result in jamming. Using higher feed forces and pressures may allow for a greater range of process conditions and may provide a consistent jacket around the substrate. In particular, use of the first guide sheath 224 extending at least partially into the first filament port 216 may facilitate the use of softer filament and greater "push-ability." Additionally, or alternatively, the use of the support element 228 may also facilitate the use of softer filament and greater "push-ability." In other embodiments, the apparatus 200 may include a screw or static mixer to help push a softer filament. In other words, the screw or static mixer may provide a cavity for softer filament material to be moved forward between the threads of the screw.

Figure 3:
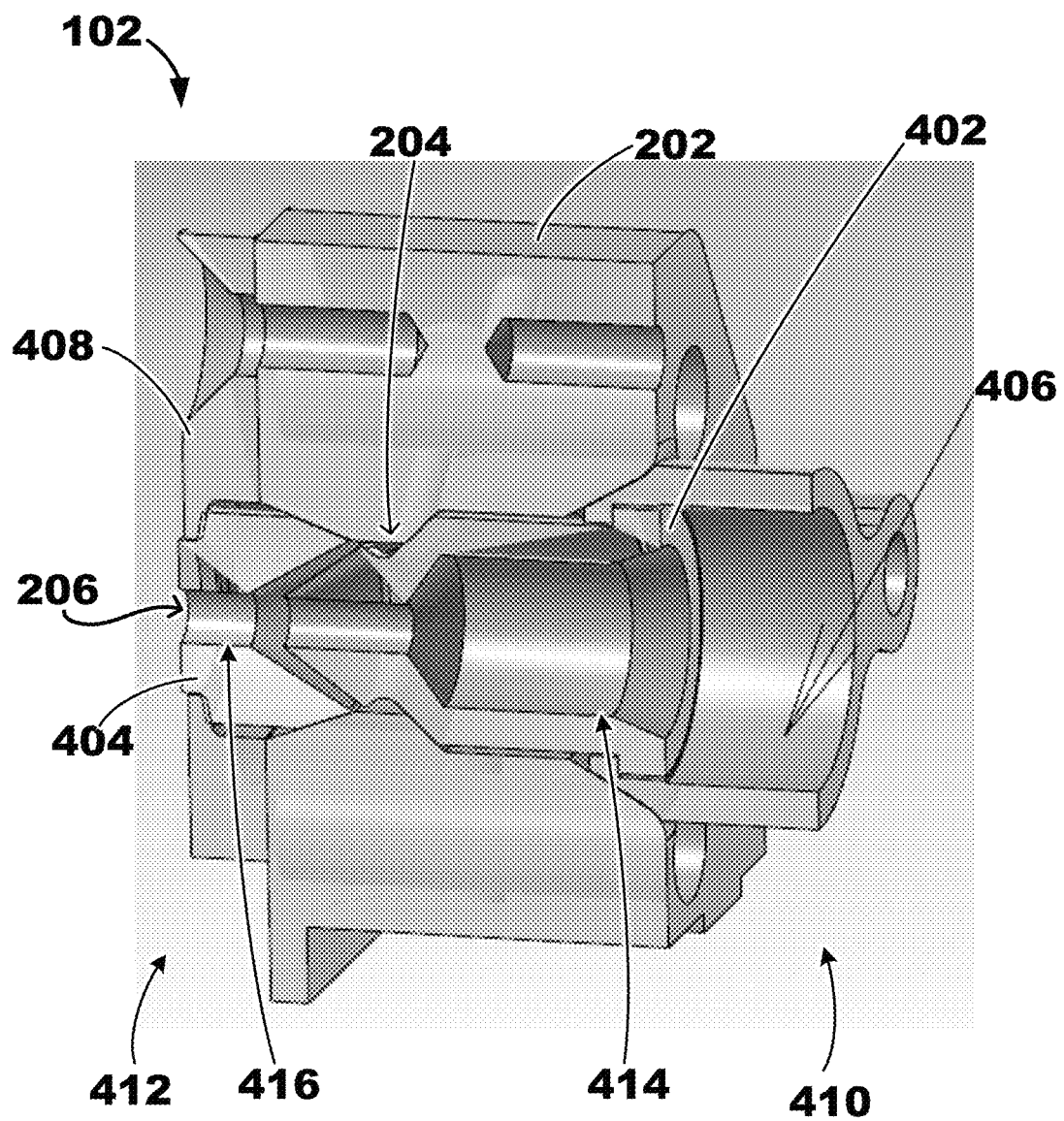
FIG. 3 is a conceptual diagram of an illustrative heating cartridge for use with, for example, the additive manufacturing system of FIG. 1.

FIG. 3 shows a partial cross-sectional side view of one example of the heating cartridge 102. The heating cartridge 102 or the heating block 202 may extend from a proximal side 410 to a distal side 412. In some embodiments, the heating cartridge 102 may include one or more of the heating block 202, an inlet die 402 coupled to the proximal side 410 of the heating block, an outlet die 404 coupled to the distal side 412 of the heating block, a proximal retaining plate 406 to facilitate retaining the inlet die adjacent to the heating block, and a distal retaining plate 408 to facilitate retaining the outlet die adjacent to the heating block.

The inlet die 402 and the outlet die 404 may be retained in any suitable manner. In the illustrated embodiment, the outlet die 404 may be retained by a distal shoulder of the distal retaining plate 408. In some embodiments, the inlet die 402 may be retained by the proximal retaining plate 406 between a distal shoulder of the proximal retaining plate 406 and a fastener, such as a nut with a lumen extending through, which may be threaded to the retaining plate to engage a proximal surface of the inlet die. The retaining plates 406, 408 may be fastened to the heating block 202 in any suitable manner.

The inlet die 402 may at least partially define a substrate inlet port 414. The outlet die 404 may at least partially define a substrate outlet port 416. The inlet die 402 may at least partially define the interior volume 204. The outlet die 404 may at least partially define the interior volume 204. In some embodiments, an exterior surface of the inlet die 402, an interior surface of the outlet die 404, and an interior surface of the heating block 202 may cooperatively define the interior volume 204.

The substrate channel 206 may be described as extending from the proximal side 410 to the distal side 412 of the heating cartridge 102, or vice versa. The substrate channel 206 may extend through the interior volume 204. As shown, the substrate channel 206 may extend through one or more of the proximal retaining plate 406, the inlet die 402, the heating block 202, the outlet die 404, and the distal retaining plate 408.

Figure 4:
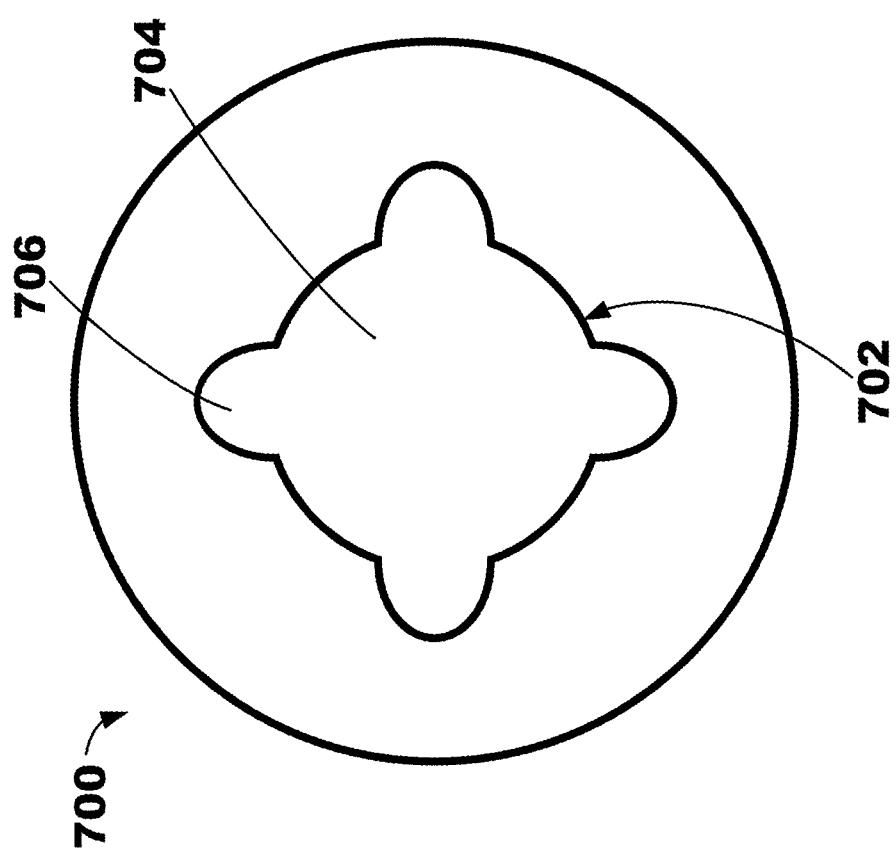
FIG. 4 is a conceptual diagram of an illustrative outlet die that may be used, for example, in the heating cartridge in the additive manufacturing system of FIG. 1.

FIG. 4 shows an end view of one example of an inlet or outlet die 700 that may be used in the heating cartridge 102 (FIG. 1). The die 700 may define a substrate inlet or outlet port 702. The port 702 may define a main region 704 and one, two, three, four, or more cutouts 706, or cutout regions. In the illustrated embodiment, the port 702 defines four cutouts 706.

When the interior cross-sectional shape die 700 is used in an outlet die, the jacket formed by the heating cartridge 102 may include a number of protrusions corresponding to the number of cutouts 706 used in the die 700. For example, the illustrated die 700 would produce four protrusions on the jacket.

In some embodiments, one or more of the cutouts 706 may be sized to receive a wire 115 (FIG. 1), such as a pull wire, which may be provided by the wire handling system 107 (FIG. 1). In some embodiments, the interior cross-sectional shape of die 700 may be used in both the input die and the outlet die to accommodate the wires 115 pulled through the cutouts 706.

Figure 5:
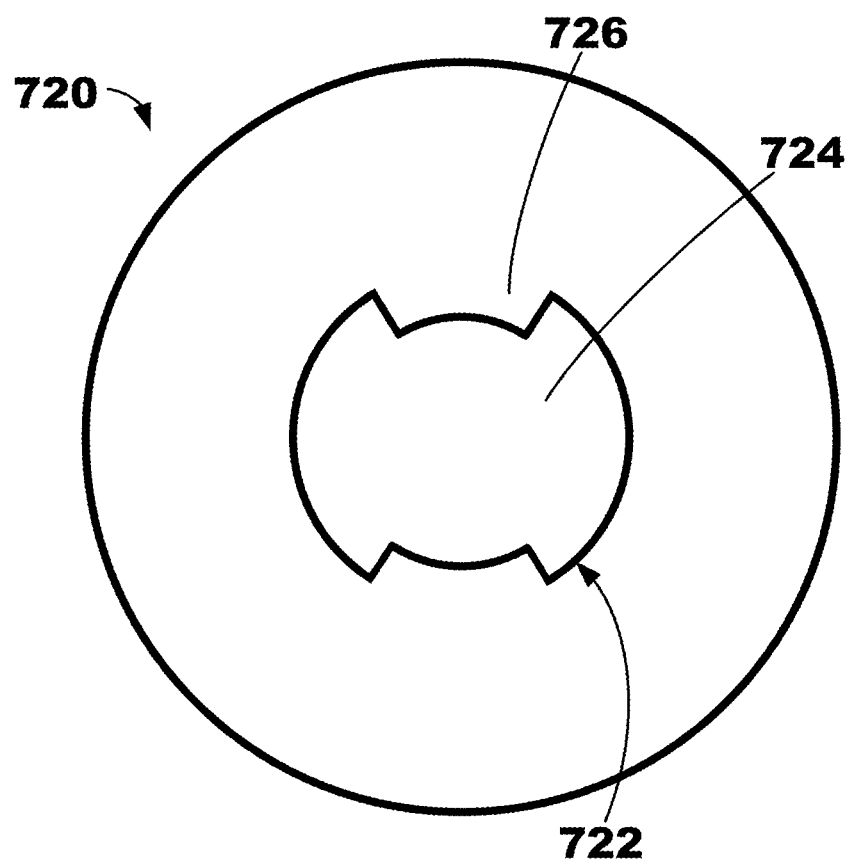
FIG. 5 is a conceptual diagram of another illustrative outlet die that may be used, for example, in the heating cartridge in the additive manufacturing system of FIG. 1.

FIG. 5 shows an end view one example of an inlet or outlet die 720 that may be used in the heating cartridge 102 (FIG. 1). The die 720 may define a substrate inlet or outlet port 722. The port 722 may define a main region 724 and one, two, three, four, or more protrusions 726, or cutout regions. In the illustrated embodiment, the port 722 defines two protrusions 726, or teeth.

When the interior cross-sectional shape die 720 is used in an outlet die, the jacket formed by the heating cartridge 102 may include a number of channels corresponding to the number of protrusions 726 used in the die 720. For example, the illustrated die 720 would produce two channels on the jacket.

The shape and feature of the outlet die 720 may control the shape and features of a resultant first jacket 500. For example, as shown in FIG. 6, the first jacket 500 defines cutouts 504 in the outer surface 502 of the first jacket 500. The first jacket 500 may be similar to the jacket 118 described herein, but may be the initial jacket that is formed and may include geometrical features thereon (e.g., the cutouts 504) upon which a second jacket may be subsequently formed. The cutouts 504 may be a result of the corresponding outlet die through which the first jacket 500 was formed. For example, the first jacket 500 of FIG. 6 defines four symmetrical cutouts having a partially circular shape. Therefore, the outlet die through which the first jacket 500 was formed included four symmetrical protrusions that are semi-circular and extend towards the center of the opening of the outlet die. Further, the cutouts 504 may extend along and parallel to the longitudinal axis 126 or may spiral or corkscrew around the outer surface 502 of the first jacket 500. While FIG. 6 illustrates four symmetrical cutouts 504, the features defined within the first jacket 500 may be any suitable shape and/or size.

After forming the first jacket 500 including features as shown in FIG. 6, one or more internal components (e.g., a lumen, a pull wire, a liner, marker elements, alignable marker elements, electrodes, electrode couplings, etc.) may be formed or deposited on the first jacket 500 (e.g., within the features defined in the first jacket 500). For example, the internal components may be positioned within channels, between protrusions, or within protrusions formed in the first jacket. A pull wire 115 may be provided by the wire handling system 107 (e.g., as shown in FIG. 1) and positioned within the cutout 504. Specifically, the number of pull wires may correspond to the number of internal components formed on the first jacket 500. As shown in FIG. 6, there may be four pull wires positioned in the first jacket 500 (e.g., one pull wire in each cutout 504). By positioning the pull wires within the pre-formed cutouts 504, the pull wires may be more effectively and consistently spaced apart.

Thereafter, a second jacket may be formed around the first jacket 500 and any internal components positioned therein. The second jacket may be formed similar to the first jacket 500 (or, e.g., as described herein as it pertains to the jacket 118) such as by feeding a second filament into the interior cavity of the heating cartridge, melting the second filament within the interior cavity, and moving the heating cartridge to form the second jacket. Further, the second jacket may be formed using the same heating cartridge as the first jacket or a different heating cartridge.

For example, in one or more embodiments, the heating cartridge 102 of the system 100 (e.g., as shown in FIG. 1) may make multiple passes (e.g., two) along the substrate to form each of the first and second jackets. Once the heating cartridge 102 extends the length of the substrate 116 to form the desired length first jacket 500, the heating cartridge 102 may return to the starting position and begin forming the second jacket. In other words, a first filament may be fed into and melted within the interior cavity of the heating cartridge 102 to form the first jacket and a second filament may be fed into and melted within the interior cavity of the same heating cartridge 102 to form the second jacket. In such embodiments, the first and second filaments may be the same filament being fed into the heating cartridge 102 (e.g., if the heating cartridge 102 only includes a single filament port). Although in some embodiments, as described herein, the heating cartridge 102 may include at least two filament ports. Therefore, the first jacket may be formed from a first filament and the second jacket may be formed from a second filament different than the first filament. In one or more embodiments, the first and second jackets may be formed from any combination of both the first and second filaments.

Figure 7:
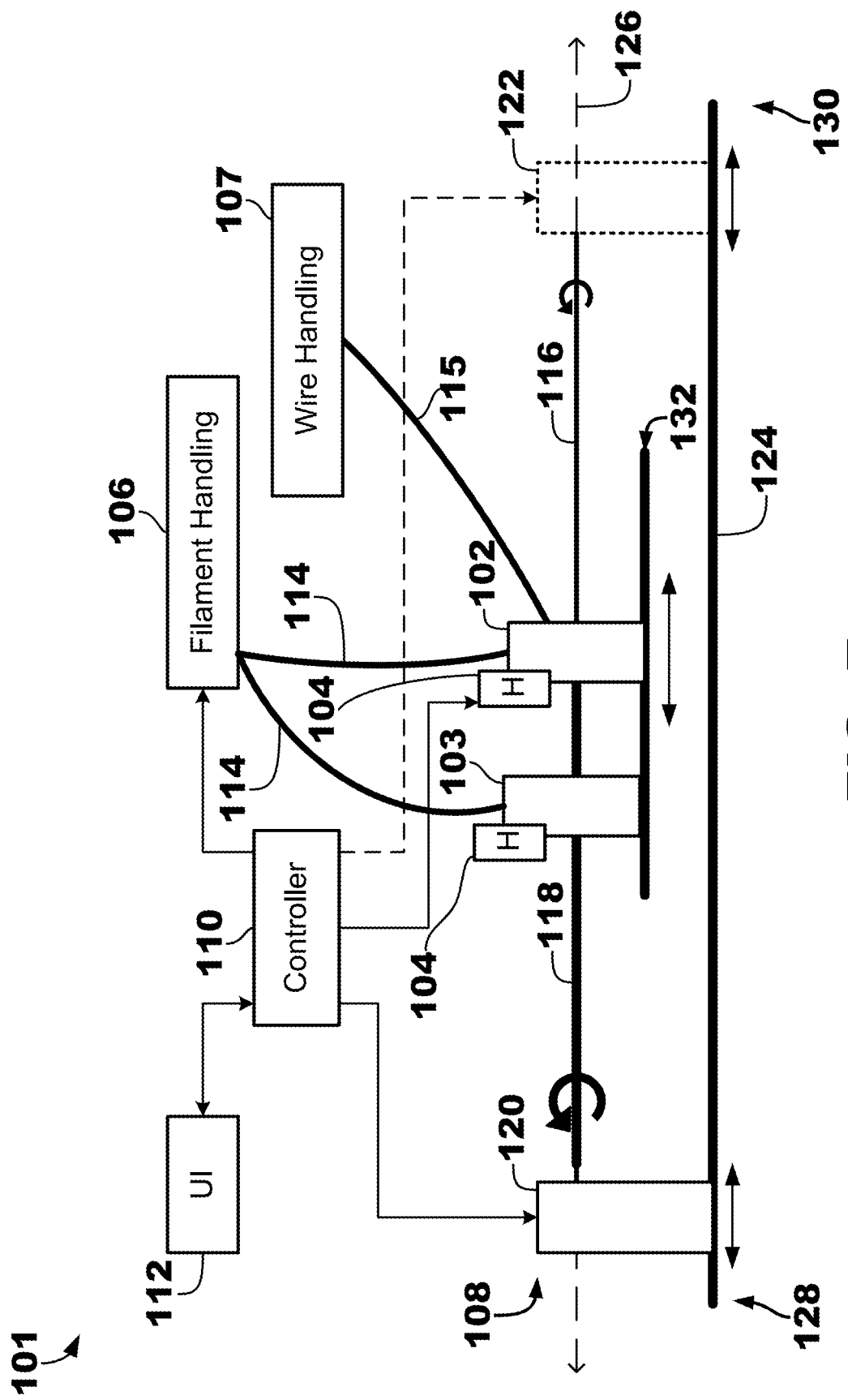
FIG. 7 is a conceptual diagram of another illustrative additive manufacturing system according to the present disclosure.

Also, as shown in FIG. 7, the system 101 may include an additional heating cartridge 103 that is distal to or trailing the heating cartridge 102. Specifically, the additional heating cartridge 103 may be longitudinally spaced (e.g., along the longitudinal axis 126) apart from the heating cartridge 102. The system 101 may include all of the same components as system 100 described in combination with FIG. 1, but include the additional heating cartridge 103. Further, the additional heating cartridge 103 may include all of the same features as the heating cartridge 102, but may be physically separate from the heating cartridge 102. In such embodiments, the heating cartridge 102 may form the first jacket and the additional heating cartridge 103 may subsequently form the second jacket around the first jacket. For example, the heating cartridge 102 may define a first filament port in fluid communication with the interior volume to receive the first filament and the additional heating cartridge 103 may define a second filament port in fluid communication with the interior volume of the additional heating cartridge to receive the second filament.

Even though the heating cartridges are separate components, the first and second filament may include a same or different filament material. Further, each of the heating cartridge 102 and the additional heating cartridge 103 may include two or more filament ports such that the jacket may be formed from a mixture of materials. As described herein, by combining filament materials into a single jacket, the characteristics (e.g., the flexibility) of the jacket may be customized. The one or more pull wires located within the catheter (e.g., between the first and second jacket) may produce varying types of movement of the catheter depending on the characteristics of the material mixture of the first and second jackets. For example, if the second jacket (e.g., outer jacket) is stiffer than the first jacket (e.g., inner jacket), the pull wires may provide greater range of motion.

As shown in each of FIGS. 1 and 7, the wire handling system 107 (which may include the one or more pull wires) may feed the pull wires 115 through the heating cartridge 102 to be positioned along the catheter. When the system 100 (e.g., as shown in FIG. 1) includes a single heating cartridge 102 making multiple passes, the pull wire 115 may be positioned after the first jacket is formed and prior to the second jacket being formed. When the system 101 (e.g., as shown in FIG. 7) includes a heating cartridge 102 and an additional heating cartridge 103, the pull wire 115 may be configured to be positioned between the heating cartridge 102 and the additional heating cartridge 103 (e.g., between the formation of the first and second jackets).

Figure 8:
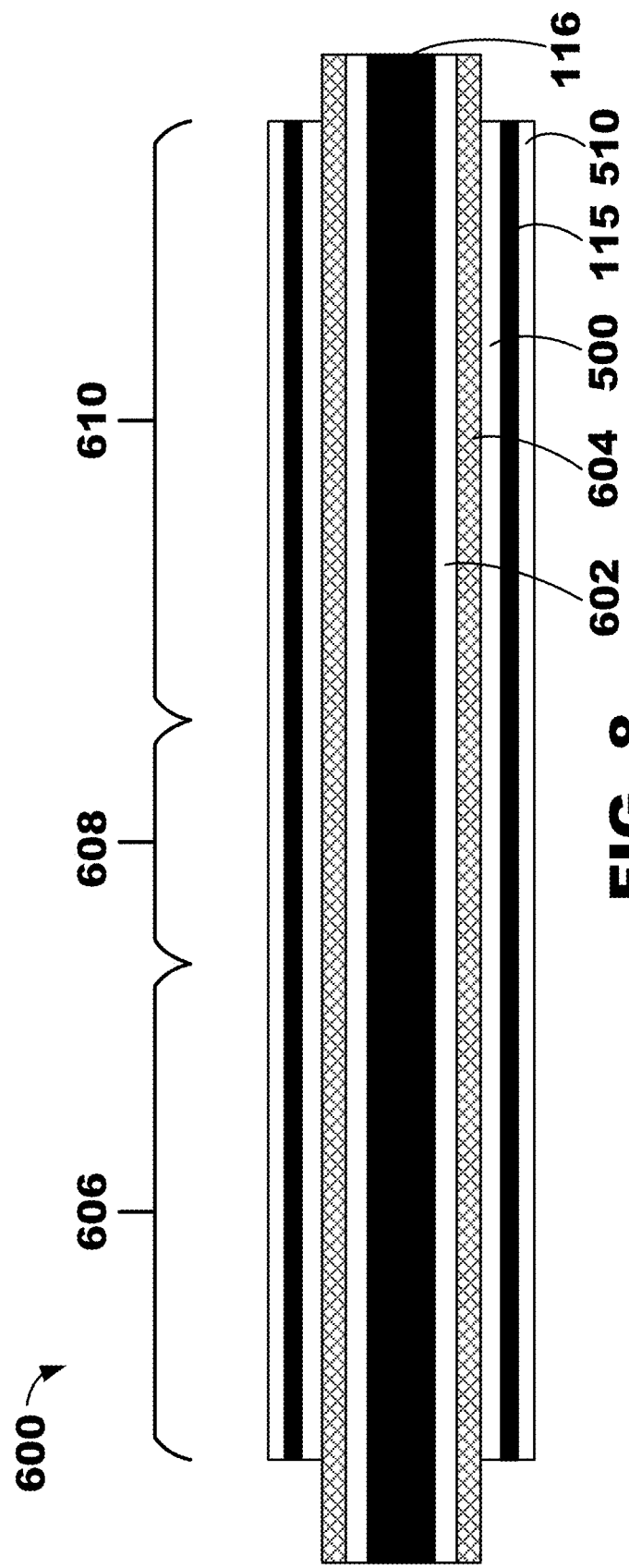
FIG. 8 is a conceptual diagram of the illustrative catheter jacket of FIG. 6 including pull wires and a second jacket using the additive manufacturing system described herein.

FIG. 8 shows one example of a catheter 600 that may be manufactured using the system 100 before the substrate 116 is removed. The substrate 116 may include a lubricious coating on its exterior surface to facilitate removal. The lubricious coating may extend around the circumference of the substrate 116. One example of a lubricious coating is a PTFE coating.

The substrate 116 may be covered with a liner 602, such as a PTFE layer. The liner 602 may be placed over the lubricious coating. The liner 602 may extend around the circumference of the substrate 116. The liner 602 may be covered with a braid 604, such as a stainless-steel braid layer. The braid 604 may be placed over the liner 602. The braid 604 may extend around the circumference of the liner 602. The braid 604 may be porous. The first jacket 500 may be applied to the braid 604. When the first jacket 500 is formed, the liner 602 may adhere to the first jacket 500 through pores in the braid 604.

As described herein the first jacket 500 may be formed with one or more cutouts (e.g., see FIG. 6). As shown in FIG. 8, the cutouts are filled with pull wires 115 extending along the length of the catheter 600. Thereafter, the second jacket 510 may be formed around the first jacket 500 and the pull wires 115.

In the illustrated embodiments, the catheter 600 includes a first segment 606, a second segment 608, and a third segment 610. Each segment 606, 608, 610 may have different durometers. In some embodiments, the first segment 606 may have a high durometer, the third segment 610 may have a low durometer, and the second segment 608 may have a continuously varying durometer in a longitudinal direction between the durometers of the first and third segments. For example, the first segment 606 may have a Shore durometer equal to 72 D, the third segment 610 may have a Shore durometer equal to 35 D, and the second segment 608 may have a Shore durometer that gradually changes from 72 D to 35 D over its length. Further, the first and second jackets 500, 510 may have the same or differing profiles extending along the longitudinal direction.

Figure 9:
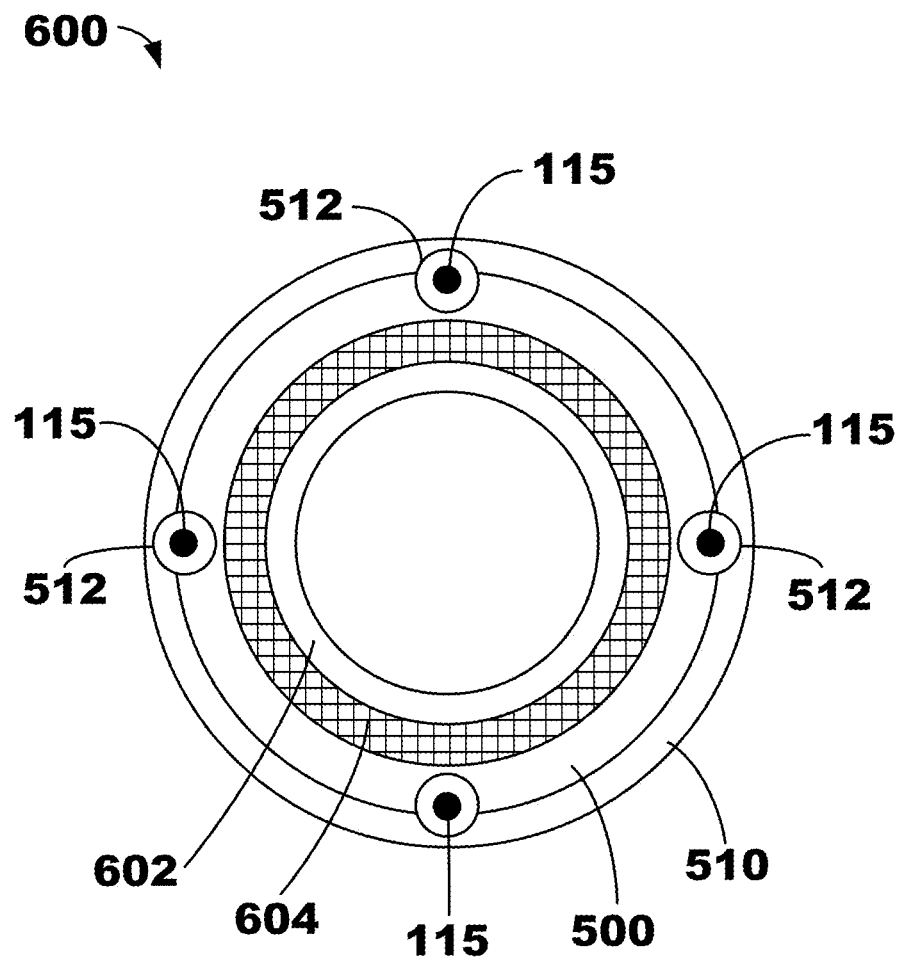
FIG. 9 is cross-sectional conceptual diagram of the illustrative catheter of FIG. 8.

FIG. 9 illustrates the catheter 600 of FIG. 8 from the conceptual cross-sectional view and without the substrate 116 positioned therein. As described herein, the first jacket 500 is formed around the braid 604 and the liner 602. The pull wires 115 are positioned within a portion of the first jacket 500 and surrounded by a liner 512 (e.g., a PTFE pull wire liner). The second jacket 510 may be formed around the first jacket 500 and the pull wire liners 512. The pull wires 115 may be symmetrically positioned around and embedded in the catheter 600. The process of embedding internal components as described herein may assist in easily spacing those internal components in a concentric way that may benefit mechanical properties and physician handling (e.g., moving the pull wires).

Figure 10:
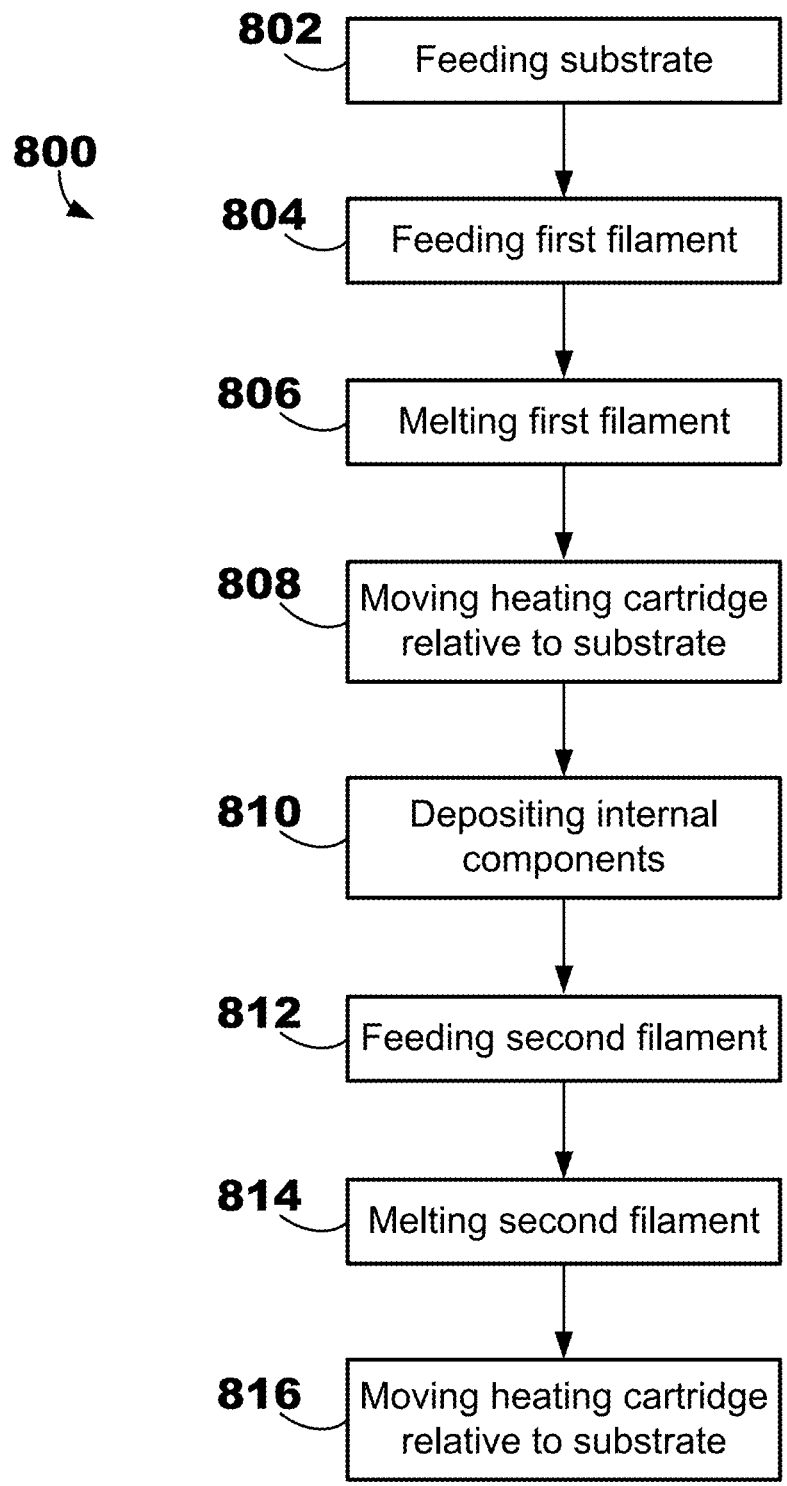
FIG. 10 is a flow diagram that illustrates one example of a method for use with, for example, the additive manufacturing system of FIG. 1.

FIG. 10 shows one example of a method 800 of using the systems 100, 101 (FIGS. 1 and 7) for additive manufacturing. The method 800 may be used to manufacture an implantable medical device. The method 800 may include feeding the substrate 802, for example, through a substrate channel in one or more heating cartridges. The substrate channel may be in fluid communication with an interior cavity of the heating cartridge. The method 800 may include feeding at least a first filament 804 through a filament port of the heating cartridge into the interior cavity. The method 800 may include melting the first filament 806, for example, in the interior cavity. Any portion of the filaments contained in the interior cavity may be melted.

The method 800 may include moving the heating cartridge relative to the substrate 808, for example, at least in a longitudinal direction to form a first jacket comprising material from at least the first filament. The heating cartridge or substrate may also be rotated relative to one another. The jacket may be formed from material of at least the first filament. In some embodiments, the jacket may be formed from material of at least the first filament and the second filament. In one or more embodiments, the outlet die may form various surface features within the outer surface of the first jacket.

For example, in one or more embodiments, forming the first jacket may include defining one or more protrusions extending from an outer surface of the first jacket. In one or more embodiments, forming the first jacket may include defining one or more channels or cutouts extending inward from an outer surface of the first jacket.

The method 800 may also include depositing one or more internal components 810 on the first jacket (e.g., relative to the features formed on the surface of the first jacket). For example, the one or more components may be deposited between the one or more protrusions or within the one or more channels. The method 800 may further include feeding at least a second filament 812 through a filament port of the heating cartridge into the interior cavity and melting the second filament 814 in the interior cavity of the one or more heating cartridges.

The method 800 may include moving the heating cartridge relative to the substrate 816, for example, at least in a longitudinal direction to form a second jacket comprising material from at least the second filament. The heating cartridge or substrate may also be rotated relative to one another. The jacket may be formed from material of at least the second filament. In some embodiments, the jacket may be formed from material of at least the first filament and the second filament. Further, the first and second jackets may be formed by a single heating cartridge making multiple passes along the substrate or by two separate heating cartridges that are spaced apart from one another.

An illustrative lead described herein may include an innovative electrode design and connection between such electrode and a conductor wire to reduce the outer diameter. Furthermore, the illustrative lead may not utilize insulation core tubing that is often used between an electrode and a coil and/or jacket of existing leads. In one embodiment, the illustrative lead utilizes a platinum-lawrencium electrode, 004 Ag/MP 35 nw/Si conductor coil, a polyurethane lead body, and a monolithic controlled release device (MCRD) silicon ring.

The illustrative leads described herein may be thinner than current leads so as to track better into small vessels (e.g., better trackability). Further, the illustrative leads may have better "pushability" and utilize less than around 80% force utilized with prior leads when placed into curved paths. Additionally, although the outer diameter of the illustrative leads may be reduced (e.g., 3 Fr, less than 3 Fr, etc.), the leads may still be compatible with current delivery systems (e.g., 0.014 inch guidewires), which means that the physicians may not have to change their clinical practice to implant these illustrative leads. Furthermore, the illustrative leads can improve CRT response by targeting optimal pacing options that are not reachable by other leads. Still further, the illustrative leads could be potentially used for other pacing therapy like hypoglossal nerve stimulation for sleep apnea.

Additionally, the leads become thinner (e.g., smaller outer diameter such as less than 4 Fr or less than 4 Fr), contact between the electrodes and the coronary vessel wall may be decreased than thicker leads. Consequently, a pacing capture threshold (PCT) for the thinner leads may tend to be higher, which can lead to a quicker depletion of the battery.

The illustrative leads described herein are designed to overcome such challenges of thinner leads (e.g., less than 4 Fr, less than 3 Fr, etc.) to lower the PCT and be sure the lead can deliver acceptable electrical signals without hampering the battery longevity. Generally, such leads utilize platinum-lawrencium electrodes, polyurethane tubing shaped with a specific design, and a conductive inner coil.

As described herein, the illustrative lead may include a lead body is used directly as insulating core tubing. An electrode may be a one-part platinum-lawrencium tube with a slit. In one or more embodiments, the illustrative leads may be manufactured, made, or formed by cutting a slit into the lead body and extending a conducting wire out of the lead body. Then, the lead body may be thermo-bonded over 2 millimeters to reduce the outer diameter on the section where the electrode will be positioned. The thermo-bonded process may also close the previous slit that was made to extend the conducting wire. The electrode may be opened a bit (e.g., using the slit) and slid over the lead body until it reaches the reduced diameter section. Then, the conducting wire may be optionally welded from the exterior on the electrode. Lastly, the electrode may be closed by deformation (e.g., crimping) and then welding the slit.

In view thereof, various illustrative leads and constructions thereof are depicted in FIGS. 11-17 that may provide thinner leaders that may better navigate small, tortious paths such as some coronary vessels than previous leads. For example, an illustrative quadripolar lead 900 that may be manufactured using the systems and methods described with respect FIGS. 1-6 is depicted in FIG. 11. The lead 900 may extend from a proximal end to a distal end 904. The distal end region, which extends from the distal end 904 for a selected length towards to the proximal end, is depicted in FIG. 11.

In this embodiment, the lead 900 may include four electrodes 906 coupled to a lead body 901. It is to be understood that other embodiments similar to lead 900 may include less than four electrode or more than four electrodes. In particular, this lead 900 includes a tip electrode 906A and three ring, or body, electrodes 906B, 906C, 906D. The tip electrode 906A is located at the distal end 904 of the lead 900 so as to be positioned furthest along a vessel while the remaining ring electrodes 906B, 906C, 906D may be distributed along vessel. The electrodes 906 may include one or more conductive materials so as to be able to sense electrical cardiac activity and deliver electrical cardiac therapy to cardiac tissue. For example, the electrodes 906 may include one or more of platinum, platinum alloy, and/or other materials known to be usable in implantable electrodes.

The ring electrodes 906B, 906C, 906D may be spaced apart along the lead body 901 to, e.g., provide various sensing and pacing locations when the lead 900 is implanted. Additionally, as shown the lead 900 may include a coil-style fixation element 909 located proximal to the ring electrode 906D. The fixation element 909 may be configured to fixate, or couple, the lead 900 to cardiac tissue so as to secure the lead 900 from moving after positioning the lead 900 in the desired location (e.g., to position the electrodes 906 in acceptable locations to provide the desired sensing and pacing capabilities for a selected therapy).

The lead 900 may be thinner or have smaller diameter 911 than typical leads. For example, the lead 900 may be less than 4 French (4 Fr), which is less than 1.333 millimeters (mm) in diameter. Further, for example, the lead 900 may be 3 Fr, which is a 1 mm diameter. Further, for example, the lead 900 may be 3.5 Fr, which is a 1.166666 mm diameter. Further, for example, the lead 900 may be less than 3 Fr. To facilitate the small size, or diameter, of the lead 900, the present disclosure describes an electrode coupling construction (or arrangement) and method of manufacturing such lead that will be described with respect to the FIGS. 12-15.

An expanded, cross-sectional view of an illustrative ring electrode 906C of the quadripolar lead 900 of FIG. 11 is depicted in FIG. 12. As shown, the ring electrode 906C is positioned around the lead body 901, and additionally, a coil conductor 910 is located inside a lumen 907 of the lead body 901. The coil conductor 910 is electrically and mechanically coupled to the ring electrode 906C as will be described further herein.

Additionally, the lead 900 shown in FIGS. 11-12 also includes monolithic controlled release devices (MCRD) 905, each located proximate one of the electrodes 906. The MCRDs 905 may be integrated with or separate from the electrodes 906 and may be coupled to the lead body 901 in the same or similar way as the electrodes 906.

Cross-sectional views showing an illustrative method of coupling the electrode 906C to the lead body 901 are depicted in FIGS. 13A-E. First, a lead body 901 is provided. The lead body 901 may be manufactured or formed using the additive manufacturing systems and processes described herein with respect to FIGS. 1-10. Generally, similar to as described with respect to FIGS. 11, the lead body 901 may extend from a proximal end to a distal end 904 and defining a lumen 907. Further, a conductor 910 may be positioned within the lumen 907.

It to be understood that only a small portion or region of the lead 900 is depicted in FIGS. 13A-E to show or illustrate the coupling of the electrode 906C thereto. In one embodiment, the small portion or region of the lead 900 depicted in FIGS. 13A-E includes two different diameters for two different regions of the lead body 901. In particular, the lead body 901 includes an extension region 912 and an electrode coupling region 914. The electrode coupling region 914 is where the electrode 906C is coupled to the lead body 901. The extension region 912 defines a first outer diameter 913 and the electrode coupling region 914 defines a second outer diameter 915 that is less than the first outer diameter 913. For example, the first outer diameter may be between about 0.75 mm and about 1.25 mm and the second outer diameter may be between about 0.5 mm and about 1 mm. In at least one embodiment, the first outer diameter may be about 3 Fr or 1 mm, and the second outer diameter may be about 0.7 mm.

The electrode coupling region 914 may provide an indentation, or space, 919 to receive the ring electrode 906C such that, e.g., an outer surface 920 of the lead body 901 may be substantially flush with an outer surface 928 of the ring electrode 906C when the ring electrode 906C is attached thereto. The indentation 919 may define a depth that is the difference between the first outer diameter 913 and the second outer diameter 915. Further, as shown in this embodiment, the indentation 919 may also define beveled sides transitioning the electrode coupling region 914 to the extension region 912 that correspond to beveled sides of the electrode 906C, which shown be shown in FIGS. 13C-13D. In other embodiments, the indentation 919 may have straight side walls.

As described herein, the lead body 901 including the extension regions 912 and electrode coupling regions 914 may be formed, or manufactured, using the additive manufacturing systems and processes described herein with respect to FIGS. 1-10. For example, when the electrode coupling regions 914 are formed, or created, less material may be applied to the substrate (e.g., rod, mandrel, core, conducting coil wrapped over the substrate, etc.) than when forming the extension regions 912 to define the second outer diameter 915 that is smaller than the first outer diameter 913.

Next, an opening 952 may be defined through the lead body 901 and a coupling portion, or segment, 950 of the coil conductor 910 may be extended outside of the lead body 901. In this example, the opening 952 is made in the electrode coupling region 914 of the lead body 901. More specifically, the opening 952 may be made through the wall of the lead body 901 from the exterior to the lumen 907 of the lead body 901.

In one or more embodiments, the opening 952 through which the coupling portion 950 of the coil conductor 910 is extended may be closed or "filled-in." For example, the electrode coupling region 914 may be thermo-bonded, which may reflow the polymer of the lead body 901 thereby closing or filling in any remaining gaps of the opening 952 around the conductor 910 extending therethrough.

Figure 15:
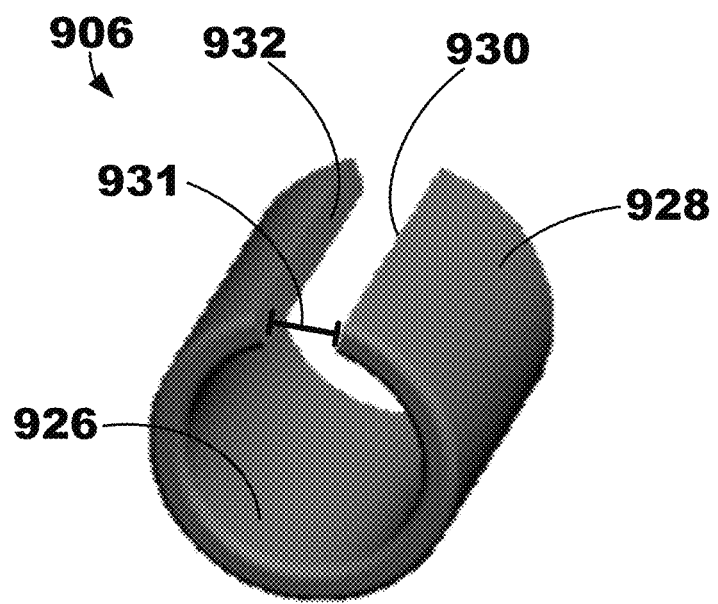
FIG. 15 is perspective view of the electrode of FIGS. 12-14.

Then, the ring electrode 906C may be positioned proximate the conductor outside of the lead body 901 in the electrode coupling region 914. An illustrative ring electrode 906 prior to fixation, or prior-fixation electrode 906, to the lead body 901 is depicted in FIG. 15. As shown, the prior-fixation electrode 906 may define a C-shape. More specifically, the prior-fixation electrode 906 may extend around a circumference from a first end 930 to a second end 932 and defines a gap 931 between the first end 930 and the second end 932. Further, the ring electrode 906C prior to fixation to the lead body 901 may be described as defining an inner surface 926, an outer surface 928, and a thickness 927 between the inner surface 926 and the outer surface 928. The thickness 927 of the ring electrode 906C prior to fixation to the lead body 901 is less than or equal to half of the difference between the first outer diameter 913 and the second outer diameter 915 of the lead body 901.

Figure 13A:
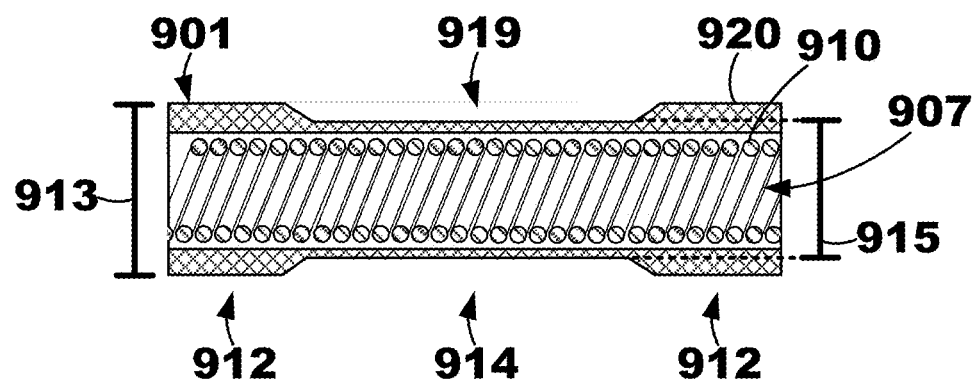
FIGS. 13A-13E are cross-sectional views showing an illustrative method of coupling the electrode of FIG. 12 to the quadripolar lead of FIG. 11.
Figure 13B:
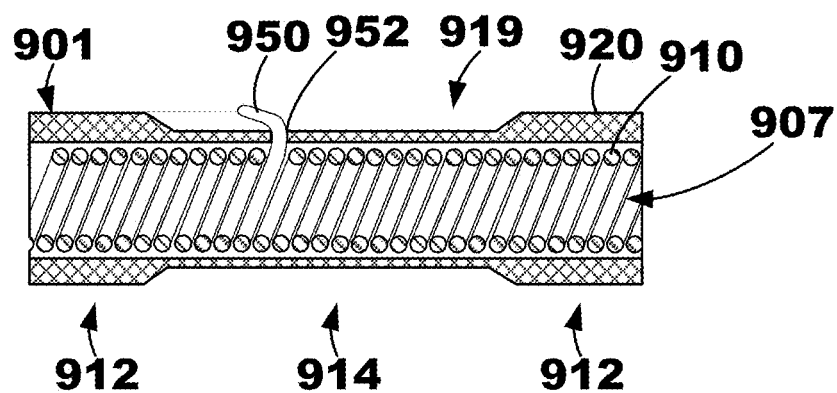
Figure 13C:
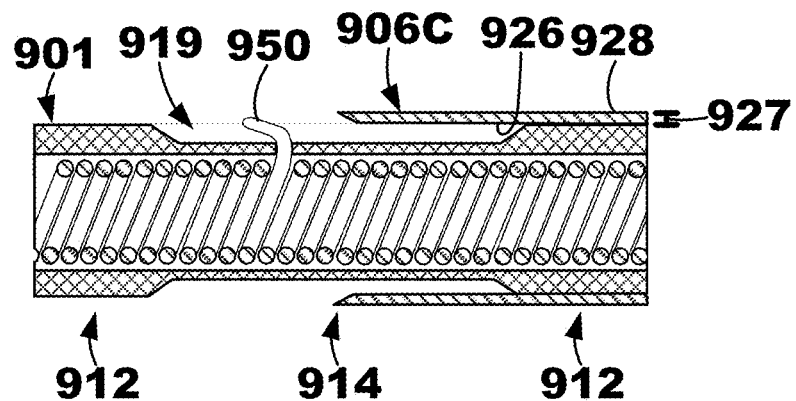
Figure 13D:
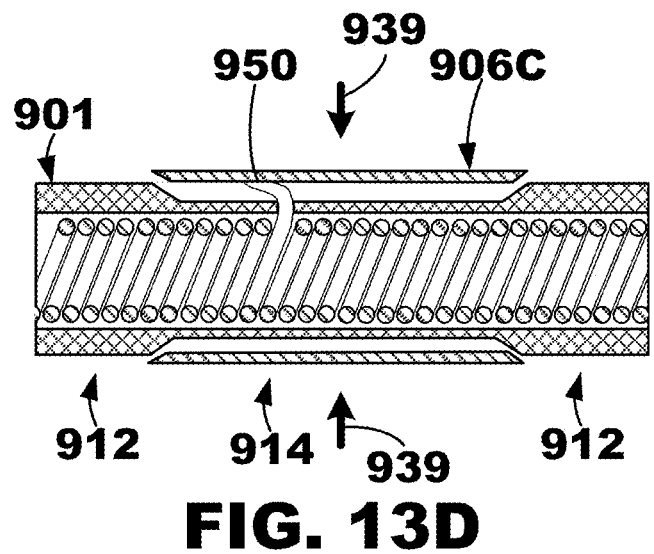

The ring electrode 906C may define a C-shape. More specifically, the ring electrode 906C may define an inner diameter that is slightly greater than the first outer diameter 913 of the extension region 914 the lead body 901, e.g., so as to be able to be moved thereabout. This, the C-shaped ring electrode 906C may be slide down, or over, the lead body 901 to the electrode coupling region 914 as shown in FIGS. 13C-13D.

Then, the ring electrode 906C may be mechanically coupled to the lead body 901 and electrically coupled to the coil conductor 910 (in particular, the segment or portion of the coil conductor 910 that extends outside of the lumen 907 of lead body 901). The electrode 906C may be mechanically coupled to the lead body 901 in a variety of ways. In at least one example, the electrode 906C may be deformed, or inwardly radially crushed, as indicated by arrows 939 to decrease the inside diameter of the ring electrode 906C to contact and fixate the inner surface 926 to the outer surface 920 of the lead body 901. In one or more embodiments, in doing so, the gap 931 defined between the first end 930 and the second end 932 may be closed. In other words, mechanically coupling the C-shaped electrode 906C onto the lead body 901 may include applying a force as indicated by arrows 939 to the C-shaped electrode 906C to deform the C-shaped electrode 906C to close the gap 931 such that the first end 930 contacts the second end 932.

Likewise, the electrode 906C may be electrically coupled to the coil conductor 910 in a variety of ways. For example, the mechanical coupling described herein may be sufficient to press the coil conductor 910 and the inner surface of the 926 of the ring electrode 906C into contact so as to provide a durable, acceptable electrical coupling therebetween. Further, for example, the electrode 906C and the coil conductor 910 may be laser welded together thereby electrically coupling to each other. In at least one embodiment, laser welding is applied to the outer surface of the C-shaped electrode to electrically couple the inner surface 926 to the coil conductor 910.

Figure 13E:
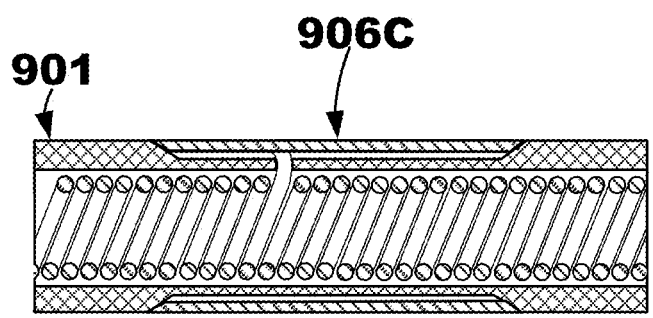

As a result, the outer surface 928 of the electrode 906C may be flush or substantially flush with the outer surface 920 of the extension region 914 of the lead body 901 as shown in FIG. 13E. Thus, the electrode coupling region 914 of the lead body 901, after the electrode 906C has been coupled thereto, may define a diameter that is less than or equal to about 1.33333 mm such as, e.g., 1.0 mm.

Figure 16:
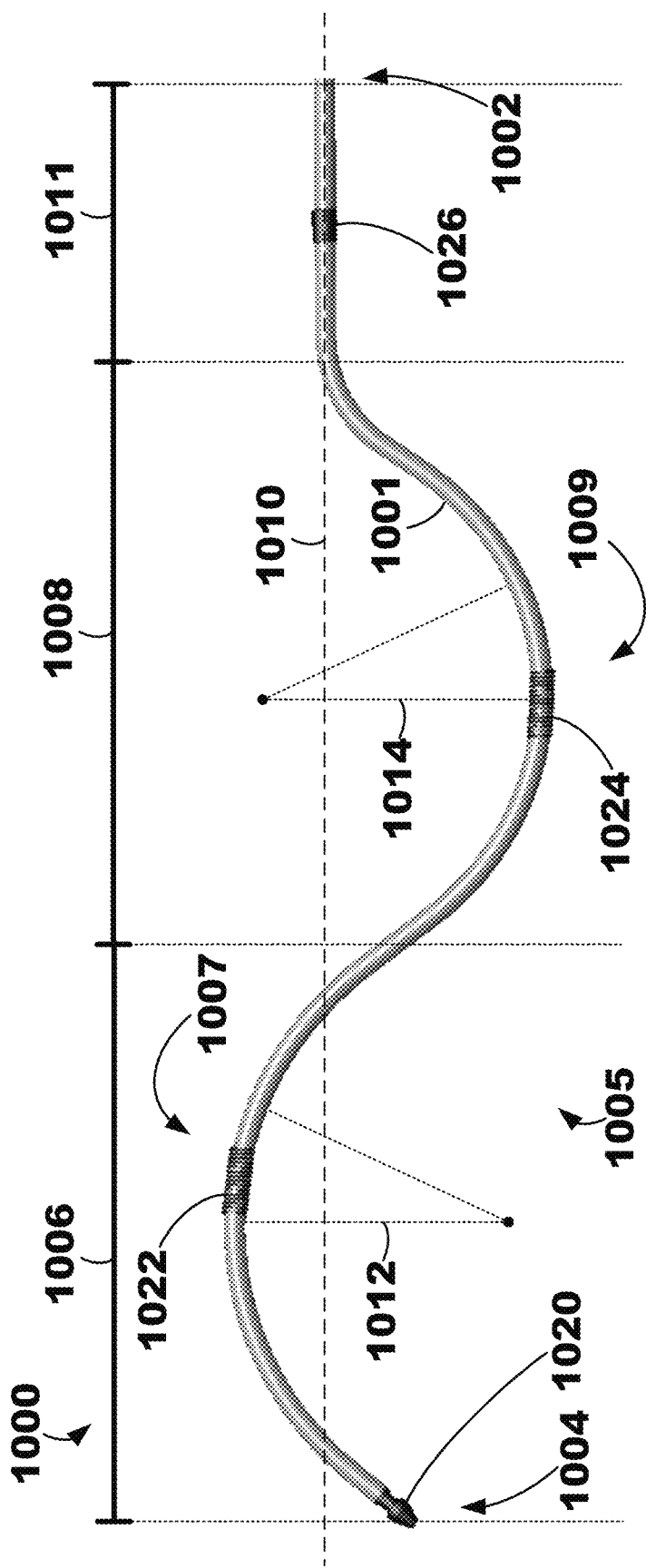
FIG. 16 is a side view of an illustrative quadripolar lead that may be manufactured using the systems and methods described with respect FIGS. 1-6 and 13-14.
Figure 17:
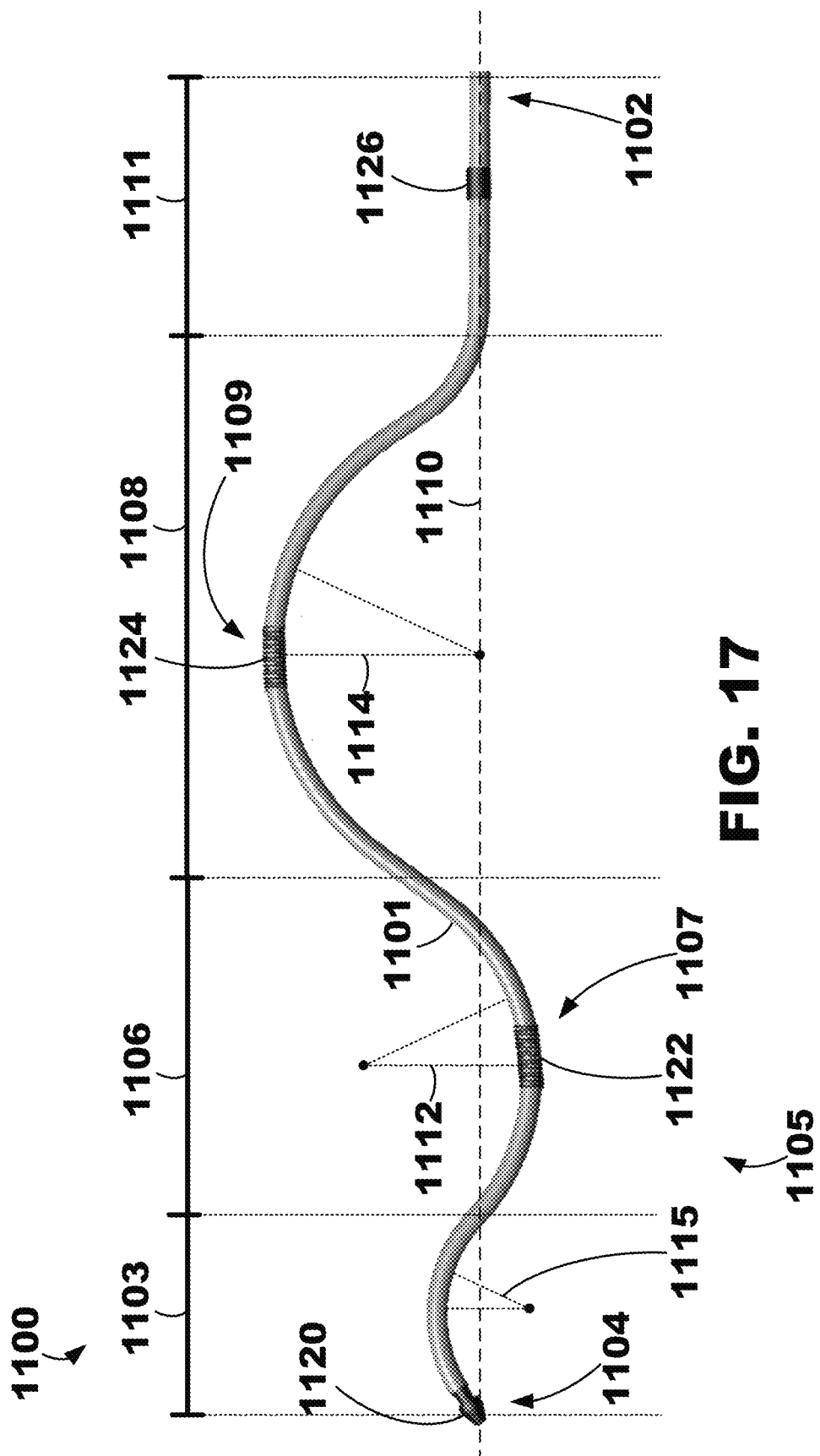
FIG. 17 is a side view of another illustrative quadripolar lead that may be manufactured using the systems and methods described with respect FIGS. 1-6 and 13-14.
Figure 27:
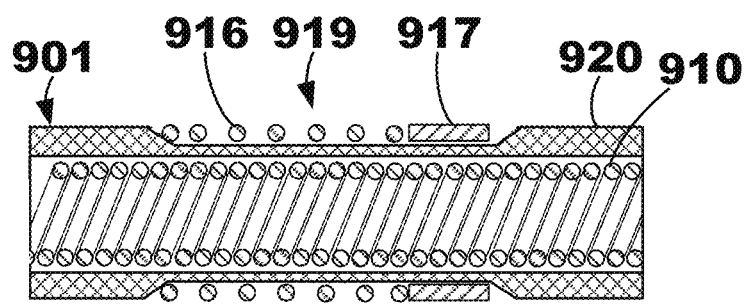
FIG. 27 is a cross-sectional view showing an illustrative electrode configuration for the quadripolar leads of FIGS. 11 and 16-17.

Additionally, although embodiment depicted in FIGS. 11-13 utilizes a ring electrode 906, it is be understood that the lead 900 may also utilize a coil electrode 916 and a C-shaped electrode 917 as depicted in FIG. 27. More specifically, for example, the coil electrode 916 may be electrically coupled (e.g., welded) to C-shaped electrode 917, which may be electrically coupled to the coil conductor 910 through the body 901 and mechanically coupled to the body 901, e.g., in a similar way as described herein with respect to FIGS. 13A-E. For instance, as shown, the coil electrode 916 and ring electrode 917 is positioned in the indentation such that an outside of the coil electrode 916 is flush with the outer surface 920 of the body 901. The coil electrode 916 may be described as being beneficial to bring support to a thinner (e.g., 3Fr) lead to maintain a S-shape as shown in FIGS. 16-17.

Figure 14A:
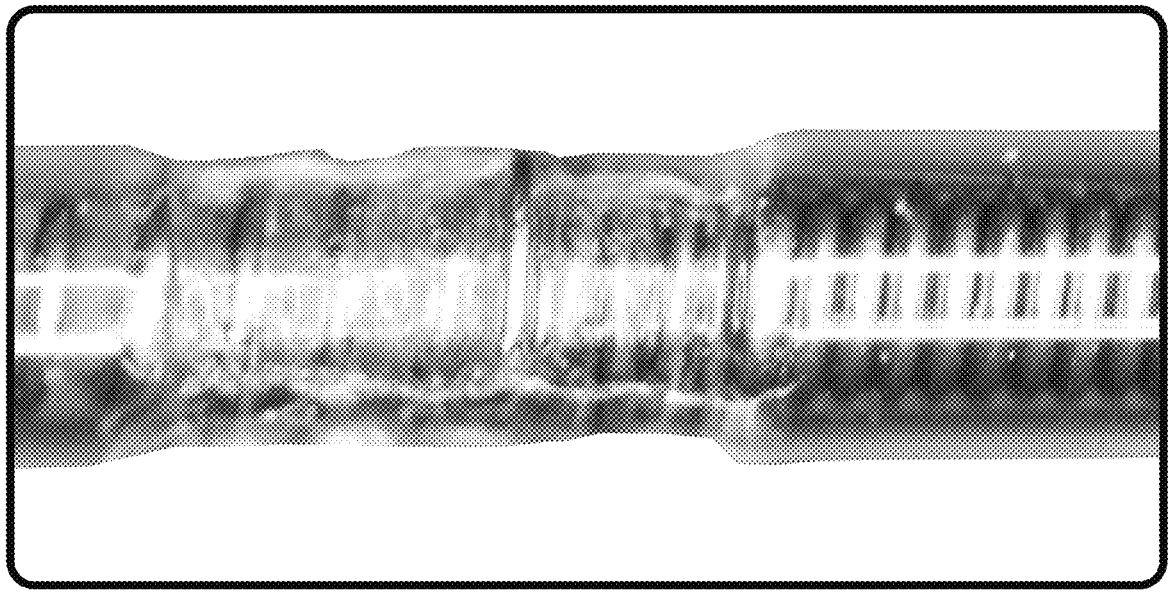
FIGS. 14A-14E are photographic side views showing an illustrative method of coupling the electrode of FIG. 12 to the quadripolar lead of FIG. 11.
Figure 14B:
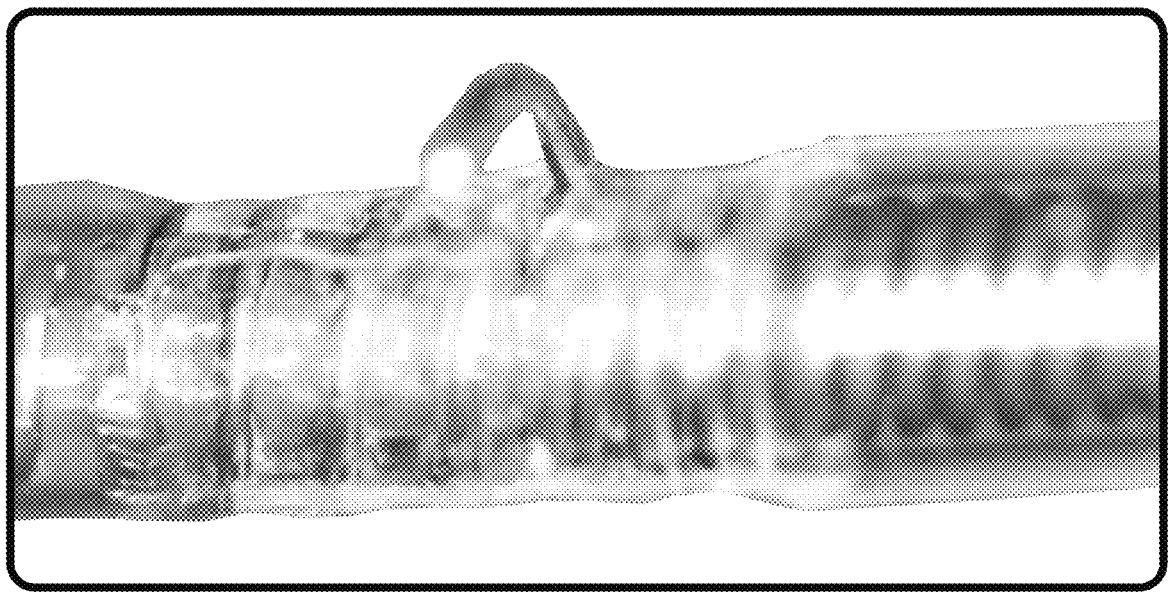
Figure 14C:
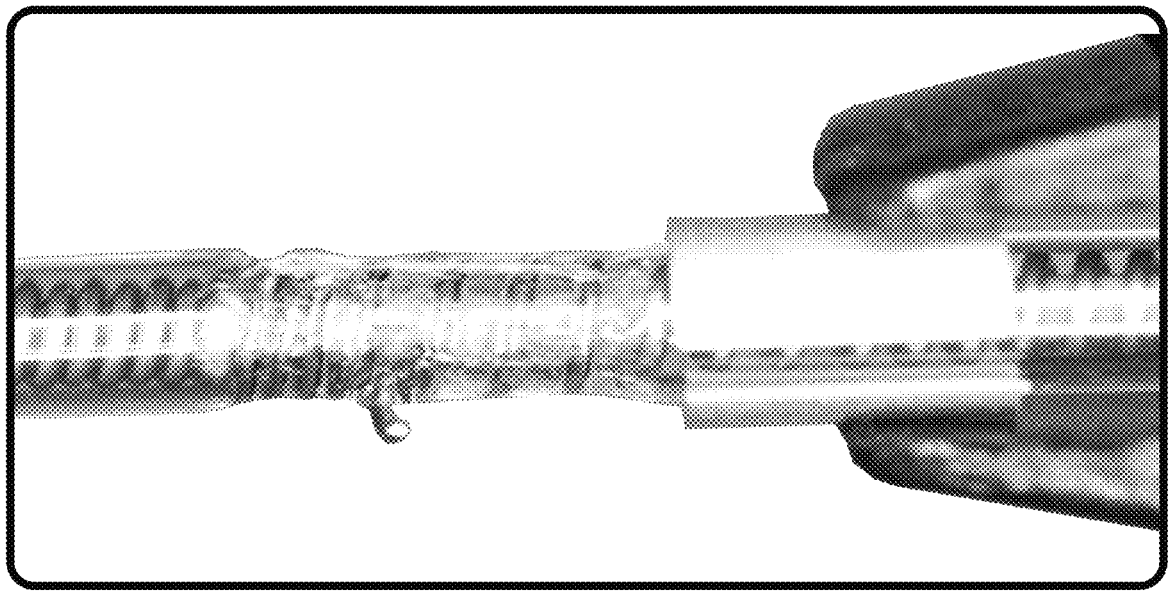
Figure 14D:
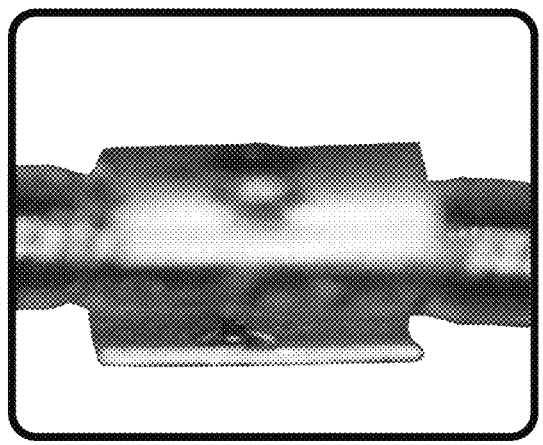
Figure 14E:
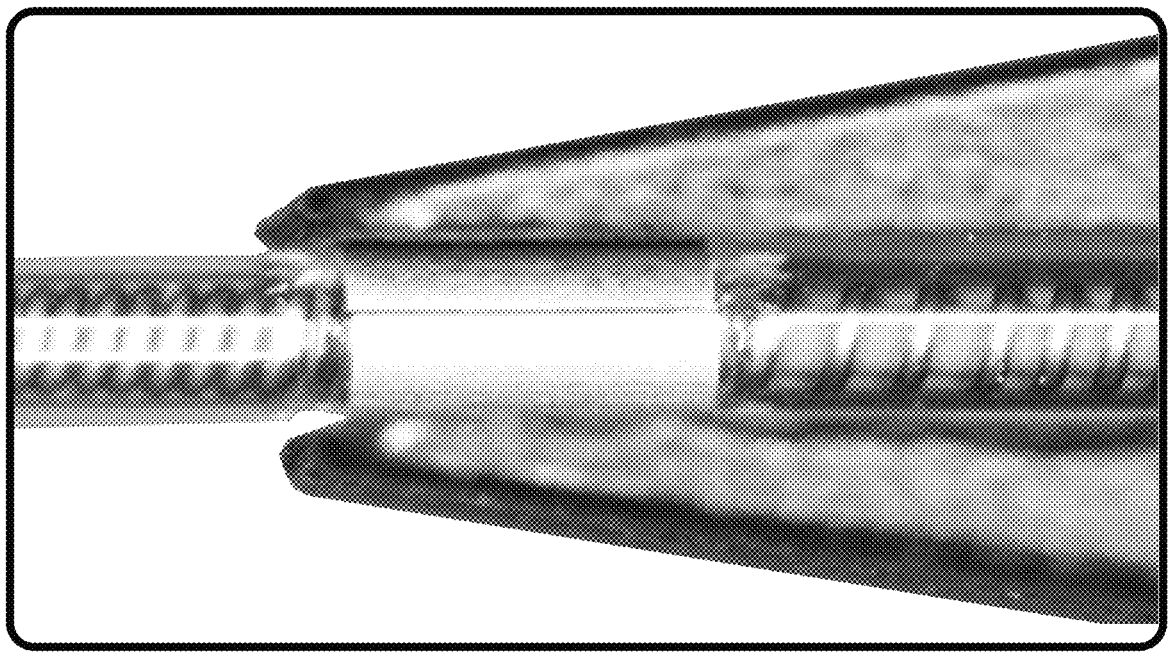

Photographic side views showing an illustrative method of coupling an electrode to a quadripolar lead are depicted in FIGS. 14A-E. As shown in FIG. 14A, a lead body including an electrode coupling region (e.g., an indentation) may be provided. An opening may be made (e.g., formed) through the lead body and a coil conductor may be extended through the opening as shown in FIG. 14B. After the coil conductor is extended therethrough, the lead body may be thermo-bonded to reflow the polymer to seal the opening. A C-shaped electrode may be slide, or moved, along the lead body as shown in FIG. 14C, and then electrically coupled to the coil conductor (e.g., through las welding) as shown in FIG. 14D. Lastly, the C-shaped electrode may be deformed through crimping as shown in FIG. 14E to mechanically coupled the electrode to the lead body.

The illustrative thinner leads (e.g., defining an outer diameter less than 1.333 mm) described herein may have various shapes and configurations. A few illustrative shapes and configurations are depicted in FIGS. 16-17. The lead 1000 of FIG. 16 may be described as having a lead body 1001 extending from a proximal end 1002 to a distal end 1004 and defining an S-shape region 1005 proximate the distal end 1004, a first apex area 1007 within the S-shaped region and a second apex area 1009 within the S-shaped region.

Each apex area 1007, 1009 may be described as the areas of the lead body 1001 that deviate a maximum distance away from a central axis 1010. More specifically, the lead body 1001 may be described as further defining a straight portion 1011 positioned proximal to the S-shaped region 1005. The straight portion 1011 may extend along and define the central axis 1010 when undeflected. The one or both of the first and second apex areas 1007, 1009, when undeflected, may be located away from the axis 1010 at a perpendicular radial distance that is greater than any other the remainder of the lead body 1001. Additionally, it may be described that the first apex area 1007 is located on the opposite side of the axis 1010 than the second apex area 1009.

Furthermore, each of the apex areas 1007, 1009 may be centered within one of the curve portions 1006, 1008 of the S-shaped region 1005. In this example, the first curve portion 1006 defines a first radius 1012 and the second curve portion 1008 defines a second radius 1014, and, when the lead 1000 is undeflected, the second radius 1014 is same the first radius 1012.

The lead 1000 may be described as being a quadripolar lead as the lead 1000 includes four electrodes. It is be understood that the lead 1000 may include more or less than four electrodes. In particular, as shown, the lead 1000 includes a tip electrode 1020, a first coil electrode 1022, a second coil electrode 1024, and a ring electrode 1026. The tip electrode 1020 is located and coupled to the distal end 1004 of the lead body 1001. The first coil electrode 1022 is coupled to the lead body 1001 and positioned at the first apex area 1007, and the second coil electrode 1024 is coupled to the lead body 1001 and positioned at the second apex area 1009. The positioning of the coil electrodes 1022, 1024 at the apex areas 1007, 1009 may facilitate consistent contact with a vessel wall to, e.g., to sense signals therefrom, to delivery pacing therapy thereto, etc.

In other words, the illustrative lead 1000 depicted in FIG. 16. may be described as a combination of a S-shaped 3 Fr lead with coil electrodes 1022, 1024. The coil electrodes 1022, 1024 may allow for a better conformability to the curved lead body and to the vessel wall. In other words, the coil electrodes 1022, 1024 may keep, or maintain, flexibility, and therefore, the electrodes 1022, 1024 can be designed longer than the usual tubular ring electrodes. In addition, the coil electrodes 1022, 1024 may be placed on, or positioned at, the apex areas 1007, 1009 of the S-shape 1005 to ensure contact between the coil electrodes 1022, 1024 and the vessel. In particular, the S-shape 1005 will press the coil electrodes 1022, 1024 onto the coronary vessel wall.

The lead 1000 of FIG. 17 may be described as having a lead body 1101 extending from a proximal end 1102 to a distal end 1104 and defining a S-shape region 1105 proximate the distal end 1104, a first apex area 1107 within the S-shaped region 1105, and a second apex area 1009 within the S-shaped region 1105.

Each apex area 1107, 1109 may be described as the areas of the lead body 1101 that deviate a maximum distance away from a central axis 1110. More specifically, the lead body 1001 may be described as further defining a straight portion 1111 positioned proximal to the S-shaped region 1005. The straight portion 1111 may extend along and define the central axis 1010 when undeflected. The one or both of the first and second apex areas 1107, 1109, when undeflected, may be located away from the axis 1110 at a perpendicular radial distance that is greater than any other the remainder of the lead body 1101. Additionally, it may be described that the first apex area 1107 is located on the opposite side of the axis 1110 than the second apex area 1109.

Furthermore, each of the apex areas 1107, 1109 may be centered within one of three curve portions 1106, 1108, 1103 of the S-shaped region 1105. In this example, the first curve portion 1106 defines a first radius 1112 and the second curve portion 1008 defines a second radius 1114, and, when the lead 1000 is undeflected, the second radius 1114 is greater than the first radius 1112. Additionally, the end curve portion 1103, that is distal from the, the first curve portion 1106, may define a third radius 1115 that is less than the first radius 1112.

The lead 1100 may be described as being a quadripolar lead as the lead 1100 includes four electrodes. It is be understood that the lead 1100 may include more or less than four electrodes. In particular, as shown, the lead 1100 includes a tip electrode 1120, a first coil electrode 1122, a second coil electrode 1124, and a ring electrode 1126. The tip electrode 1120 is located and coupled to the distal end 1104 of the lead body 1101. The first coil electrode 1122 is coupled to the lead body 1101 and positioned at the first apex area 1107, and the second coil electrode 1124 is coupled to the lead body 1101 and positioned at the second apex area 1109. The positioning of the coil electrodes 1122, 1124 at the apex areas 1107, 1109 may facilitate consistent contact with a vessel wall to, e.g., to sense signals therefrom, to delivery pacing therapy thereto, etc.

The illustrative lead 1100 depicted in FIG. 17. may be described as being similar to the lead 1000 of FIG. 16, except that the radius of the curved portions 1108, 1106, 1103 of the S-shape 1105 decreases over the length of the lead towards the distal end 1104. The two most distal electrodes 1120, 1122 may be placed into smaller vessels compared to the remaining electrodes 1124, 1126 which may be located into larger, more proximal sections of the coronary vessels. The curve radius decreasing along the illustrative lead 1100 of FIG. 17 may provide an ability of the lead 1100 to adapt to different vessel diameters.

Generally, the illustrative leads of FIGS. 16-17 may lower the pacing capture threshold, provide better contact between the electrodes and the vessel walls, provide flexible electrodes that conform to the curved lead body and to the vessel wall, adapt to the variability of the diameters over the coronaries, and, due to the flexibility of the coil electrodes, provide better trackability in tortuous vessels.

The present disclosure provides various design-based methods to create an alignment or targeting feature within a delivery system, catheter, sheath, lead, or similar device. Additionally, the present disclosure could also be applied to valve delivery, stent, or any other implant delivery system. In one or more embodiments, it may be described that the present disclosure utilizes one or more markers (e.g., radiopaque markers, echogenic markers, etc.) of a specific geometric design (e.g., hemispherical annulus, annular ring/marker band, or other shape) that can be used to create a target fiducial shape when aligned. The markers may be spaced and aligned to provide a different target fiducial shape or image when in different imaging planes (e.g., fluoroscopic imaging, ultrasound imaging, etc.). When the alignment of the markers is correct, the catheter, lead, or other implantable device may be positioned in 90-degree opposition to a target site (e.g., the target site may be a substantially planar wall such as the septal wall). Thus, the alignment of the marks in 90-degree opposition may be described as giving a visual signal (e.g., a fiducial shape) to the implanting physician within the image thereby indicating that the catheter, lead, or other implantable device is aligned correctly prior to, e.g., fixating or deploying the device screw the lead or catheter or deploy the device in the preferred, target location with the appropriate, desired angle.

An additional approach would be to use one marker on a delivery catheter shaft and another marker on a lead being delivered by the delivery catheter. The proximal marker can be located on the delivery catheter shaft and the distal marker can be located on the lead body. Alternately, the proximal marker could also be located on the lead body and the distal marker could be located on the delivery catheter shaft. Both options would result in the markers forming a "target" fiducial shape when the delivery catheter and the lead are properly aligned.

The present disclosure may be described as making a difficult implanting procedure significantly easier as it provides a visual signal (e.g., fiducial shape) to the implanter that they are in the proper alignment to deploy therapy. This can translate into significant reductions in complications, procedure time, and procedure/implanter efficacy that would result in less devices used and better outcomes for the patient. Simplification of the delivery process of implantable cardiac devices, specifically the utilization of existing technologies with new modalities to create a repeatable, predictable implant are valuable, can lead to more efficient procedures, better patient outcomes, and reduced implant times.

Furthermore, the present disclosure may be described as providing marker bands that when aligned in a prescribed fluoroscopic or ultrasound projection will help the implanter navigate toward a desired target site or structure. In one or more embodiments, the described technology incorporates the use of radiopaque or echogenic materials incorporated in the design of delivery systems or implantable devices in conjunction with methods that guide an implanting physician to use and align the delivery tools for ideal fixation or implantation of devices. When used in a prescribed orientation, these markers may guide and help the implanter navigate three-dimensionally while the implanter is viewing a two-dimensional image (e.g., a fluoroscopic or echogenic image).

In at least one embodiment, the present disclosure provides methods that includes pre-procedure or intraprocedural imaging (e.g., computing tomography (CT), ultrasound, etc.) to identify general structures or points within the anatomy that are relevant to the implant procedure. This may include, among other things, septal wall thickness, septal wall angle with relation to the tricuspid valve plane, right ventricle orientation and size, etc. Further, the method may include selection of proper device for implantation having proper specifications, which may include lead length, catheter length, catheter shape, etc. The method may further include using simple tools, algorithms, and tip cards for pre-procedure planning of imaging views based on the previous steps or processes.

In embodiments where implantable electrodes are to be implanted in the septum to, e.g., deliver cardiac conduction system pacing therapy, the method may include typical access procedures to navigate and deliver the device (e.g., delivery catheter, lead, etc.) to the right ventricle. Additionally, in one or more embodiments, the bundle of His may be mapped to, e.g., confirm a generalized implant location and establish iso-centered orientation of right anterior and left anterior oblique fluoroscopic planes, which may have been determined during pre-procedure or intraprocedural imaging. The imaging plane developed pre-procedure may be confirmed and adjustments may be made during the implant operation. Then, the method may include moving the device to the target location and aligning the markers (e.g., radiopaque markers, echogenic markers, etc.) as viewed "live" using imaging. Once the markers are aligned as shown in the imaging plane, the device may be deployed and fixated at the target site or location.

In one or more embodiments utilizing echogenic catheters, a trans-thoracic echo (TTE) may be utilized to obtain optimal four chamber, short axis, and other relevant views that show the interventricular septum (IVS). Alternatively, TEE or intracardiac echocardiography (ICE) could be used to achieve similar relevant views to guide this procedure. Further, the device may be tracked with distal region or features coated with echogenic material to the target location and the position and orientation of the distal tip of the device may be evaluated using the imaging views. Based on the imaging, the device location and orientation may be adjusted to obtain perpendicular orientation of the device to the septum, and then the device may be deployed and fixated at the target site or location.

In other words, in one embodiment, when a distal end region of an implantable device, such as a delivery catheter or lead, that includes two or more alignable marker elements is a perpendicularly aligned to a target location such as the septum, the marker elements may create a fiducial shape (e.g., a circle, an aperture, a sight ring, etc.) known to the implanter. Thus, the implanter, upon viewing the imaging during implant, will know whether the implantable device is appropriately aligned for implantation or delivery. The present disclosure may be described as being able to reduce complexity for implanters and provide greater procedural efficiency and predictability, which will decrease complications and save valuable resources for hospital systems. Additionally, in one or more embodiments, when the two or more alignable marker elements are not perpendicularly aligned to a target location such as the septum, the marker elements may create a non-alignment fiducial shape (e.g., overlapping circles or portions of a circle, staggered rings, arrows, etc.) to indicate to the implanter that the implantable device is not aligned or imperfectly aligned. Furthermore, non-alignment fiducial shape may include features that allow the implanter to understand the direction the implantable device may be moved, flexed, or other manipulated to position the implantable device in proper alignment.

Figure 18:
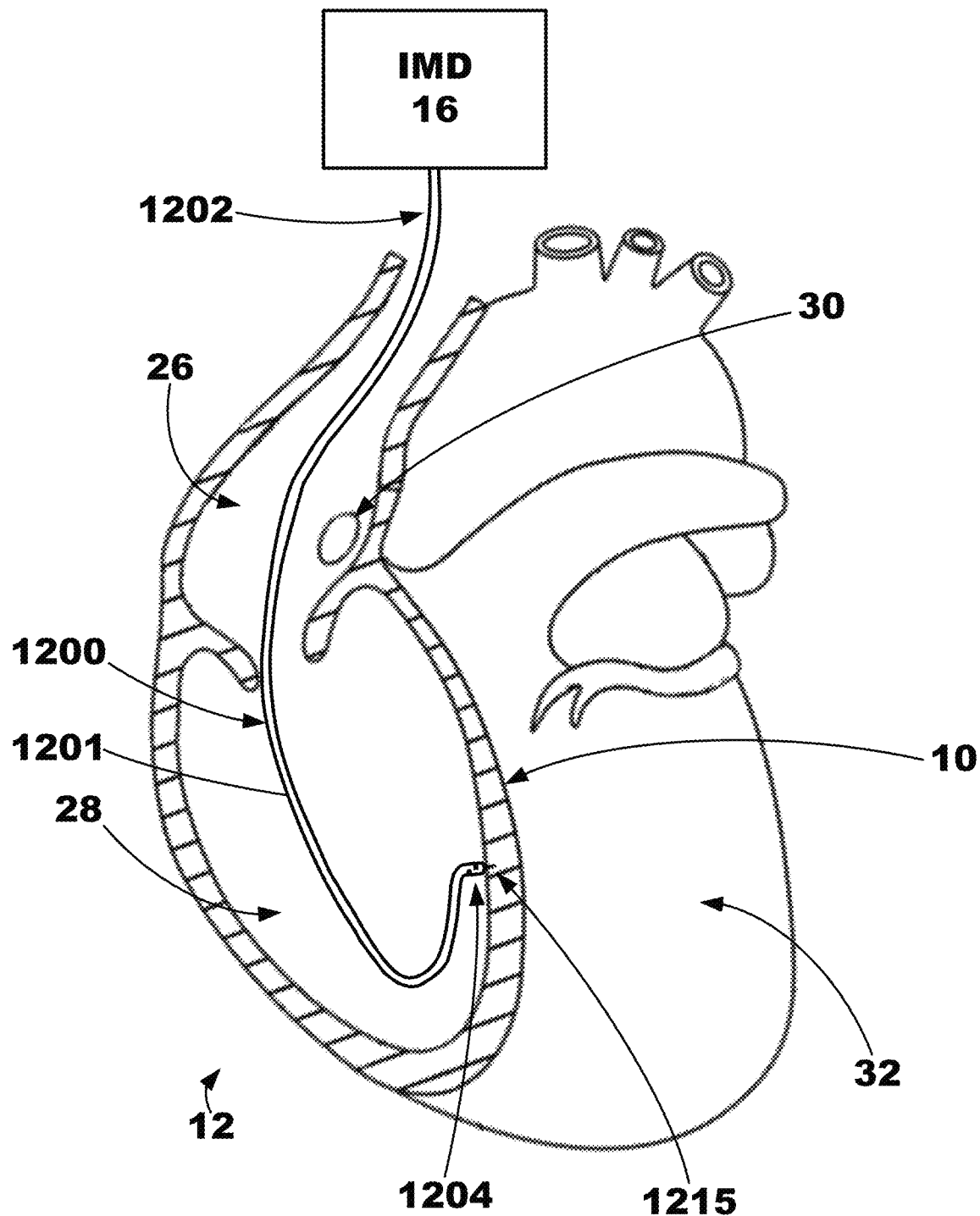
FIG. 18 is an illustrative view of a lead including two alignable marker elements implanted in the septal wall of the right ventricle.

In view thereof, an illustrative lead 1200 implanted in a patient's heart 12 in FIG. 18. More specifically, the lead 1200 may extend into the heart 12 of the patient to sense electrical activity of the heart 12 and/or to deliver electrical stimulation to the heart 12, and in particular, to sense electrical activity and/or to deliver electrical stimulation to the interventricular septum 10 of the heart 12. For example, the lead 1200 may be configured to delivery cardiac conduction system pacing therapy to the left and/or right bundle branches, the bundle of His, etc. from a location in the septum 10. Further, for example, the lead 1200 may be configured to delivery traditional myocardial pacing therapy to left and/or right ventricular myocardial tissue from a location in the septum 10. In the example shown in FIG. 18, the lead 1200 extends through one or more veins (not shown), the superior vena cava (not shown), the right atrium 26, and into the right ventricle 28. Then, the lead 1200 is positioned adjacent to the septum 10 in the right ventricle 28. Additionally, although a single lead is depicted in FIG. 18, it is to be understood that the lead 1200 may be used with one or more additional leads or leadless devices configured to sense electrical activity and/or deliver pacing therapy to the left ventricle, right ventricle, right atrium, etc. For example, the lead 1200 may be used in conjunction with a traditional left ventricular coronary sinus lead extending through one or more veins, the vena cava, the right atrium 26, and into the coronary sinus 30 to a region adjacent to the free wall of the left ventricle 32 of the heart 12 and/or a right atrial lead extending through one or more veins and the vena cava, and into the right atrium 26 of the heart 12.

Additionally, as diagrammatically shown, the lead 1200 may be operably coupled to an implantable medical device (IMD) 16. The IMD 16 may sense, among other things, electrical signals attendant to the depolarization and repolarization of the heart 12 via electrodes coupled to the lead 1200 or another lead such as a left ventricular lead, right atrial lead, etc. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., A-V delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMB. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode.

The septal pacing lead 1200 may be described as including a body 1201 extending from a proximal end region 1202 to a distal end region 1204. The proximal end region or portion 1202 may be located proximate the IMD 16 for operably coupling thereto and the distal end region or portion 1204 may be locatable, or positioned, at a target site, which in the example depicted in FIG. 18 is the intraventricular septum 10.

In the embodiment depicted, the distal end region 1204 may extend along a distal end region axis 1205. More specifically, the distal end region axis 1205 may be a straight, uncurving line, which the distal end region 1204 may extend along, and thus, the distal end region 1204 may also define a straight, uncurving line. In other embodiments, the distal end region 1204 may not extend along an axis, and may, for example, define a variety of different shapes or curves, and the alignable marker elements described further herein, may be configured to take into account the shape and curvature of the distal end region 1204.

Figure 19A:
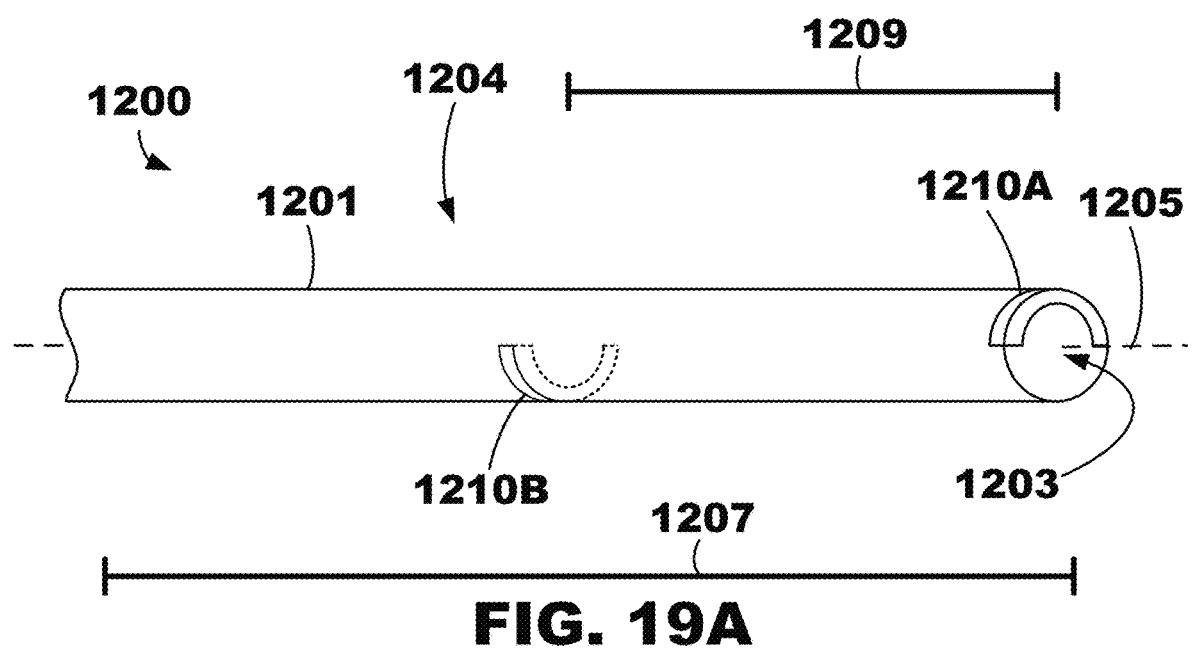
FIG. 19A is an illustrative view of the lead of FIG. 18.

The distal end region 1204 of the lead 1200 is depicted in FIG. 19A. As shown in this embodiment, the lead 1200 further includes two alignable marker elements 1210A, 1210B coupled to the body 1201. Each of the alignable marker elements 1210 defines a complementary shape that complements the other alignable marker element such that, when the distal end region 1204 is viewed axially, the two alignable marker elements 1210 form a fiducial shape indicative of acceptable alignment of the distal end region 1204 for positioning at a target site (e.g., in alignment with the target site).

The alignable marker elements 1210 may include one or more materials capable of being imaged when located inside a patient (e.g., capable of being imaged through tissue) such as, e.g., when located inside the heart of a patient. For example, the alignable marker elements 1210 may include one or more of radiopaque materials viewable through fluoroscopy, echogenic materials viewable with ultrasound, etc. The radiopaque materials may include one or more of gold, platinum, platinum/iridium, titanium, tantalum, barium silicate, barium tungsten, barium sulfate, bismuth trioxide, bismuth oxychloride, bismuth subcarbonate, and/or combinations or compounds thereof. The echogenic materials may include one or more of perfluorocarbon, coated tungsten, tungsten carbide particles distributed within a base polymeric material, etc.

The alignable marker elements 1210 may be partially or fully embedded within the body 1201 of the lead 1200 such that some or no portions of the alignable marker elements 1210 may be exposed to, e.g., body fluid, tissue, etc. In one embodiment, the alignable marker elements 1210 may also provide other functionality such as pacing and/or sensing electrodes, and thus, may be electrically coupled to circuity including conductors and the IMD 16.

The distal end region 1204 may define a distal end region length 1207 that may vary depending on application. The distal end region 1204 may be defined by the portion of the lead body 1201 that extends in a straight line along the distal end region axis 1205. In the present application of pacing the septum 10 from the right ventricle 28, the distal end region length 1207 may be between about 5 millimeters (mm) and about 20 mm. Additionally, the alignable marker elements 1210 may be spaced apart from each other at a spacing distance 1209. In other words, the most distal alignable marker element 1210A, which may be referred to as the distal alignable marker element 1210A, may be located the spacing distance 1209 away from the most proximal alignable marker element 1210B, which may be referred to as the proximal alignable marker element 1210B. Similar to the distal end region length 1207, the spacing distance 1209 may vary depending on application. In the present application of pacing the septum 10 from the right ventricle 28, the spacing distance 1209 may be between about 3 mm and about 30 mm. In at least one embodiment, the spacing distance 1209 is 10 mm. Additionally, the spacing distance 1209 may be selected and/or the shape and size of the alignable marker elements may be adjusted depending on the target site and tolerance of implantation thereto. For example, when implanting a lead into the intraventricular septum, acceptable alignment may be within 20% to being substantially perpendicular to the septum. Thus, the spacing distance 1209 may be selected and/or the size and shape of the alignable marker elements 1210 may be adjusted to achieve the with 20% of perpendicular for this implant location.

Furthermore, the distal alignable marker element 1210A may be located proximate the distal end 1203 of the lead 1200, which may be configured to be adjacent, or in contact, with the target site or location when the lead 1200 is properly implanted. Additionally, although not shown in FIG. 19A but shown in FIG. 18, the lead 1200 may further include a fixation element 1215 extending from the distal end 1203 configured to fixate or attached the distal end 1203 of the lead 1200 to the target site. In one embodiment, the fixation element 1215 may be a helical fixation element that may be "screwed" into tissue such as the septum 10.

As described herein, each of the alignable marker elements 1210 defines a complementary shape that complements the other alignable marker element such that, when the distal end region 1204 is viewed axially, the two alignable marker elements 1210 form a fiducial shape indicative of acceptable alignment of the distal end region 1204 for positioning at a target site. The complementary shapes of the alignable marker elements 1210 can be virtually any shape or size so as to provide the functionality of being able to determine whether the distal end region 1204 is properly aligned at the target site when viewed axially (e.g., looking along the distal end region axis 1205, in imaging plane perpendicular to the distal end region axis 1205, etc.). Additionally, as will be described further herein, the complementary shapes of the alignable marker elements 1210 can be virtually any shape or size so as to provide the functionality of being able to determine in what direction the distal end region 1204 is not aligned to the target site when viewed axially (e.g., looking along the distal end region axis 1205, in imaging plane perpendicular to the distal end region axis 1205, etc.).

For example, the complementary shape of each of the two alignable marker elements 1210 in FIG. 19A is a semicircle. The semicircular shape of the proximal alignable marker element 1210B opens in an opposite direction to the semicircular shape of the distal alignable marker element 1210A. Thus, when the distal end region 1204 of FIG. 19A is imaged axially, the fiducial shape would be the combination of the two opposite semicircles, which is a single circle. Additionally, when the distal end region 1204 of FIG. 19A is imaged off axis, the two opposite semicircles would not combine to form, or define a single circle, and thus, not providing a fiducial shape.

Figure 19B:
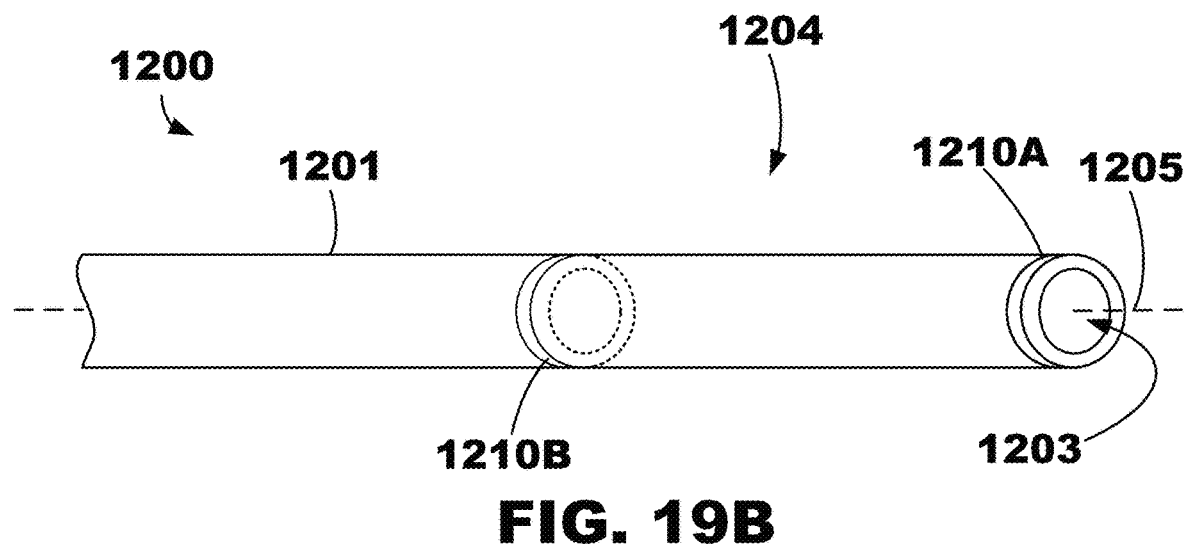
FIG. 19B is an illustrative view of another lead including two alignable marker elements.

Another example is depicted in FIG. 19B where each of the two alignable marker elements 1210 has the same complementary shape, which is a circle. Thus, when the distal end region 1204 of FIG. 19B is imaged axially, the fiducial shape would be the combination of the two circles, which is a single circle. Additionally, when the distal end region 1204 of FIG. 19B is imaged off axis, the two circles of the two alignable marker elements 1210 would not combine to form, or define a single circle, and instead, would depict two separate circles or two circles only partially overlapping, and thus, not provide a fiducial shape.

Other examples of complementary shapes for the alignable marker elements may include complete or partial triangles, pentagons, squares, rectangles, alphanumeric symbols, "puzzle" shapes, a zig-zag, etc.

Figure 20A:
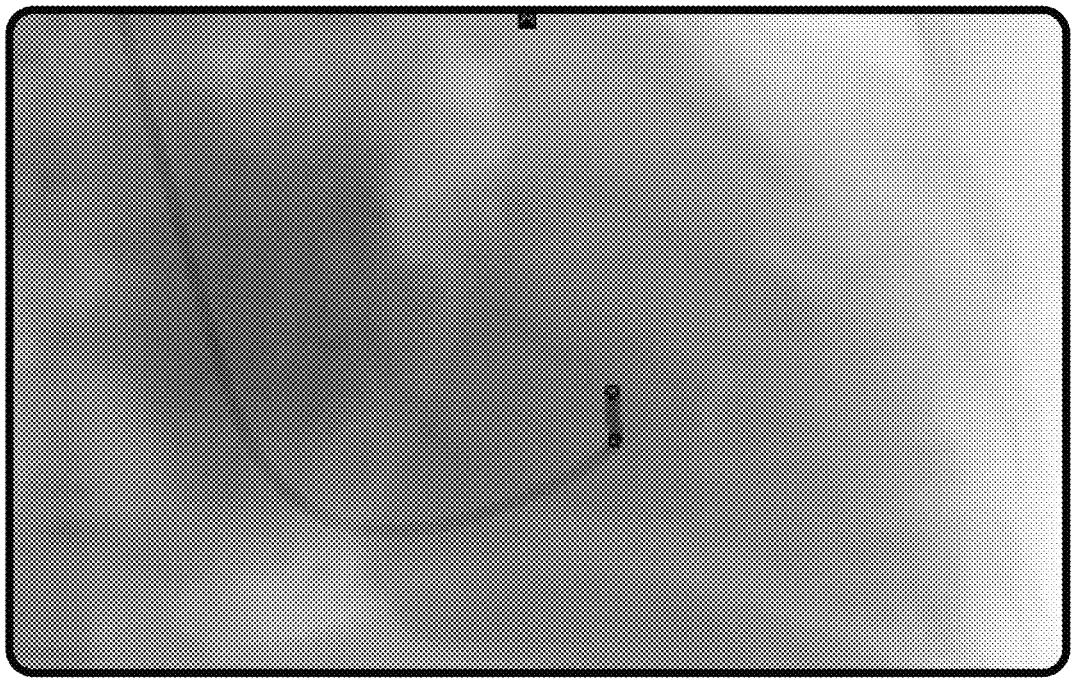
FIGS. 20A-20B are simulated right anterior oblique (RAO) fluoroscopic images taken 20 degrees off perpendicular to the septum depicting a lead including two alignable marker elements where the lead is not in intended alignment for implantation into the septum and where the lead is in intended alignment for implantation into the septum, respectively.
Figure 20B:
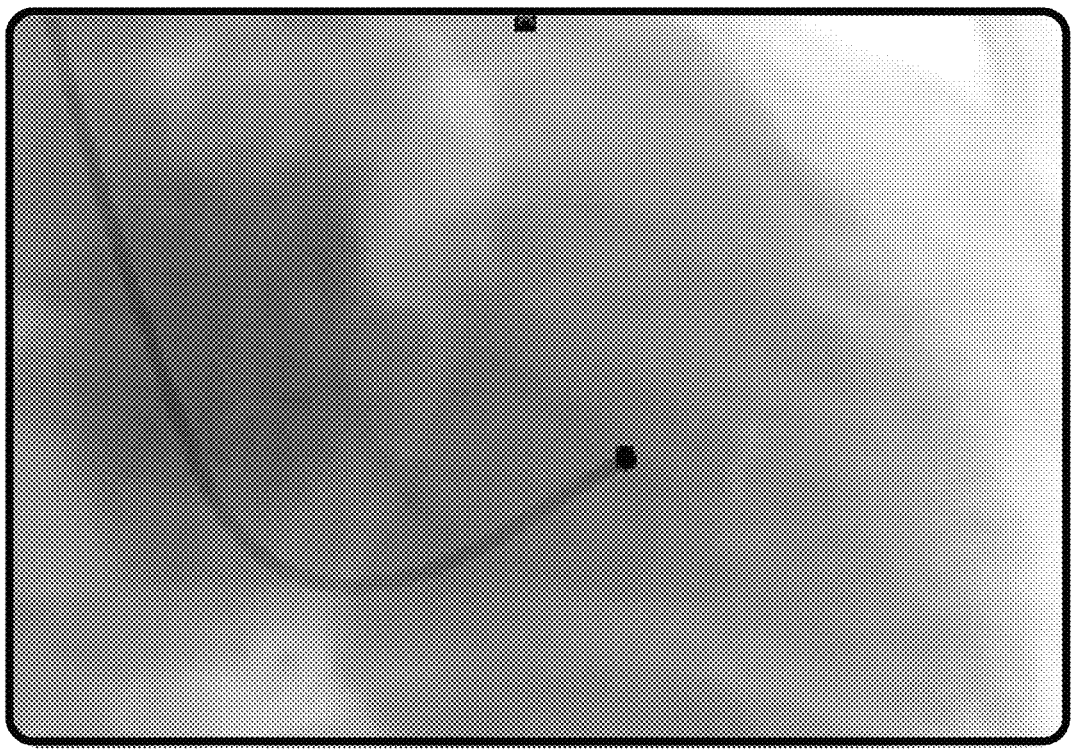

Simulated right anterior oblique (RAO) fluoroscopic images taken 20 degrees off perpendicular to the septum depicting the lead 1200 including two alignable marker elements 1210 of FIG. 19B are shown in FIGS. 20A and 20B. As shown, the distal end region 1204 is not in alignment in FIG. 20A as the two alignable marker elements 1210, which are both circles, do not even partially overlap to create the fiducial shape of a single circle. Instead, the simulated RAO fluoroscopic image clearly shows two separate circles, each from a different alignable marker element 1210, thereby indicating that the distal end region 1204 is not aligned perpendicularly to the RAO imaging plane.

Conversely, the distal end region 1204 is in alignment in FIG. 20B as the two alignable marker elements 1210, which are both circles, overlap to create the fiducial shape of a single circle. More specifically, the simulated RAO fluoroscopic image clearly shows a single circle as opposed to two separate circles or a shape formed by partially overlapping circles, thereby indicating that the distal end region 1204 is aligned perpendicularly to the RAO imaging plane.

Another illustrative lead 1200 is depicted in FIGS. 21-23 that includes two alignable marker elements 1210 that each have complementary shapes that are complete circles. More specifically, diagrammatic side views of the distal lead region 1204 with respect to a target site and illustrative images taken perpendicular to the target site are shown with the distal lead region 1204 in alignment in FIGS. 21A and 21B and out of alignment in FIGS. 22A 22B. More specifically, as shown in FIG. 21A, the distal end region axis 1205 of the distal end region 1204 is substantially perpendicular to the target site 1250, e.g., the intraventricular septum, and thus, the image taken perpendicular to the target site depicted in FIG. 21B depicts the fiducial shape of a single circle. Further, as shown in FIG. 22B, the distal end region axis 1205 of the distal end region 1204 is substantially not perpendicular to the target site 1250, e.g., the intraventricular septum, (e.g., instead, the distal end region axis 1205 is about 30 degrees away from perpendicular), and thus, the image taken perpendicular to the target site depicted in FIG. 22B does not depict the fiducial shape of a single circle, and instead, depicts two separate circles.

Figure 23A:
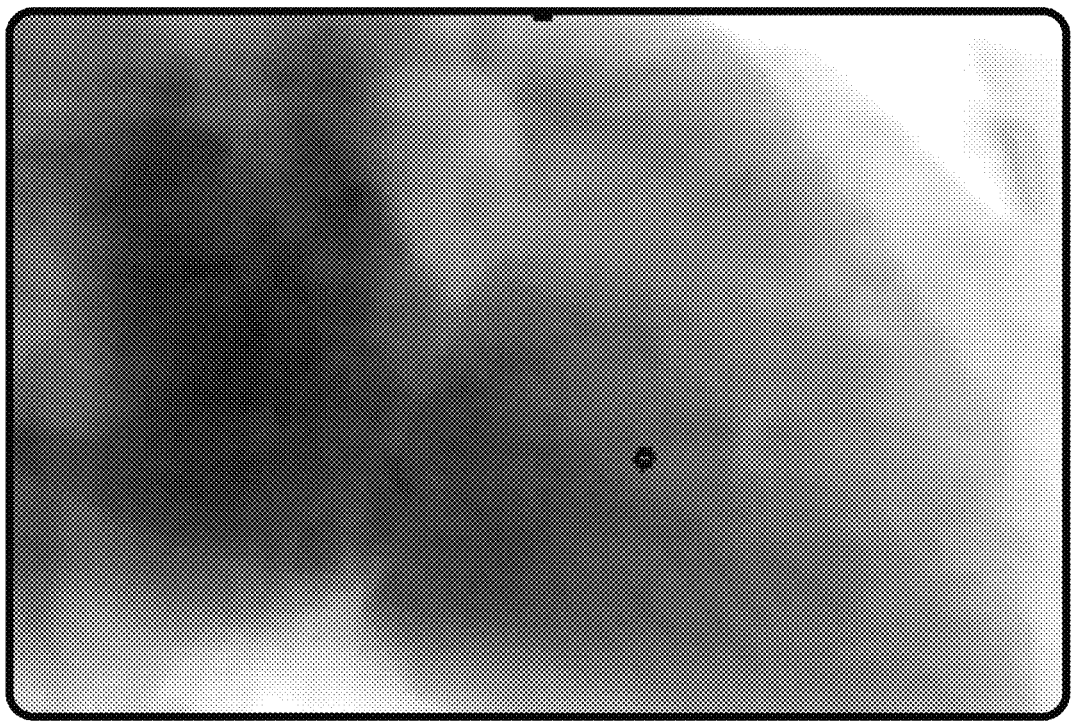
FIG. 23A is a simulated RAO fluoroscopic image taken 20 degrees off perpendicular to the septum depicting the lead of FIG. 21A including two alignable marker elements where the lead is in intended alignment similar to as shown in FIGS. 21A-21B.
Figure 23B:
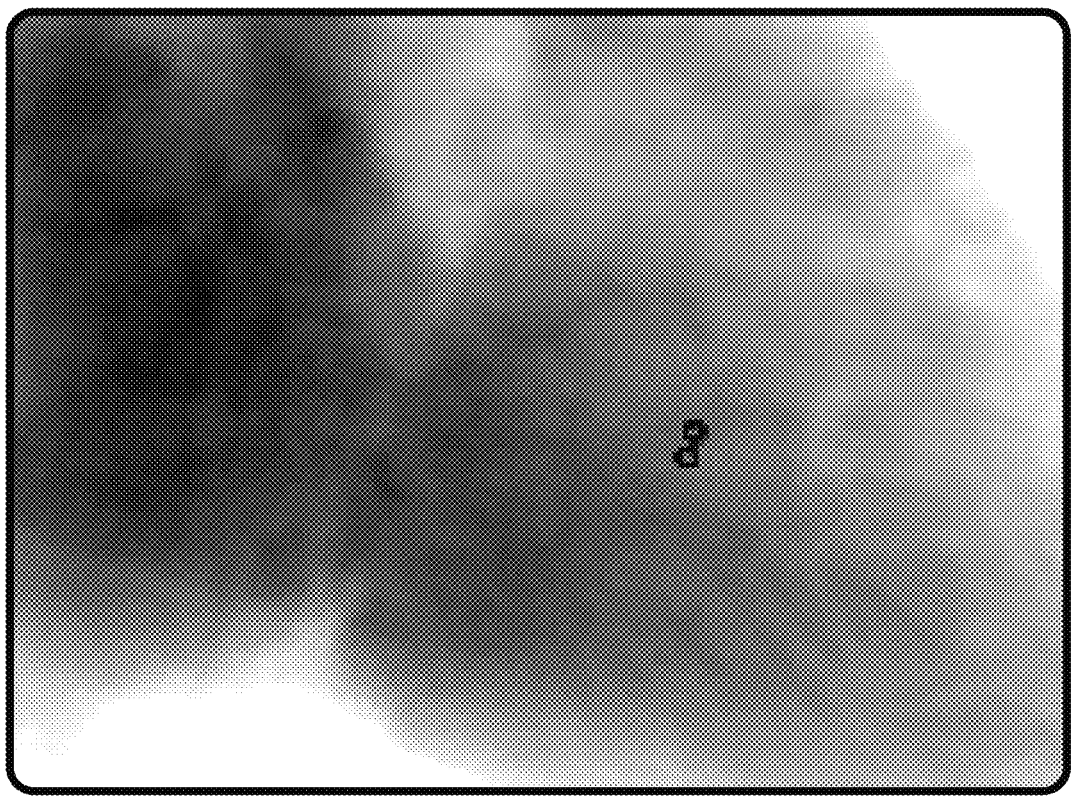
FIG. 23B is simulated RAO fluoroscopic image taken 20 degrees off perpendicular to the septum depicting the lead of FIG. 21A including two alignable marker elements where the lead is not in intended alignment similar to as shown in FIGS. 22A-22B.

A simulated right anterior oblique (RAO) fluoroscopic image taken 20 degrees off perpendicular to the septum depicting the distal lead region 1204 as aligned in FIG. 21A is shown in FIG. 23A. As can been seen in the image of FIG. 23A, a fiducial shape of a single circle is present indicating alignment. Conversely, a simulated RAO fluoroscopic image taken 20 degrees off perpendicular to the septum depicting the distal lead region 1204 as unaligned in FIG. 22A is shown in FIG. 23B. As can been seen in the image of FIG. 23B, no fiducial shape of a single circle is present, and instead, two separate circles are present indicating non-acceptable alignment.

Another illustrative lead 1200 is depicted in FIGS. 24-26 that includes two alignable marker elements 1210 that each have complementary shapes that are opposing semicircles (e.g., half circles facing with the open sides facing each other). More specifically, diagrammatic side views of the distal lead region 1204 with respect to a target site and illustrative images taken perpendicular to the target site are shown with the distal lead region 1204 in alignment in FIGS. 24A and 24B and out of alignment in FIGS. 25A and 25B. More specifically, as shown in FIG. 24A, the distal end region axis 1205 of the distal end region 1204 is substantially perpendicular to the target site 1250, e.g., the intraventricular septum, and thus, the image taken perpendicular to the target site depicted in FIG. 24B depicts the fiducial shape of a single circle. Further, as shown in FIG. 24B, the distal end region axis 1205 of the distal end region 1204 is substantially not perpendicular to the target site 1250, e.g., the intraventricular septum, (e.g., instead, the distal end region axis 1205 about 30 degrees away from perpendicular), and thus, the image taken perpendicular to the target site depicted in FIG. 25B does not depict the fiducial shape of a single circle, and instead, depicts two separate semicircles spaced apart from one another.

Figure 26A:
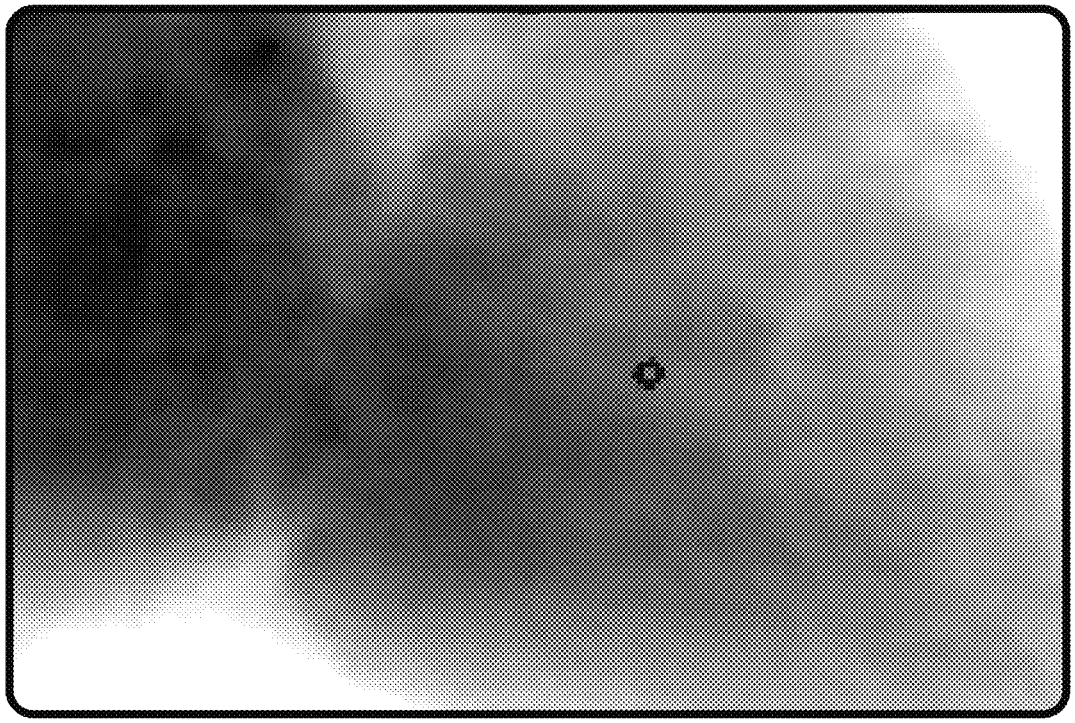
FIG. 26A is a simulated RAO fluoroscopic image taken 20 degrees off perpendicular to the septum depicting the lead of FIG. 24A including two alignable marker elements where the lead is in intended alignment similar to as shown in FIGS. 24A-24B.
Figure 26B:
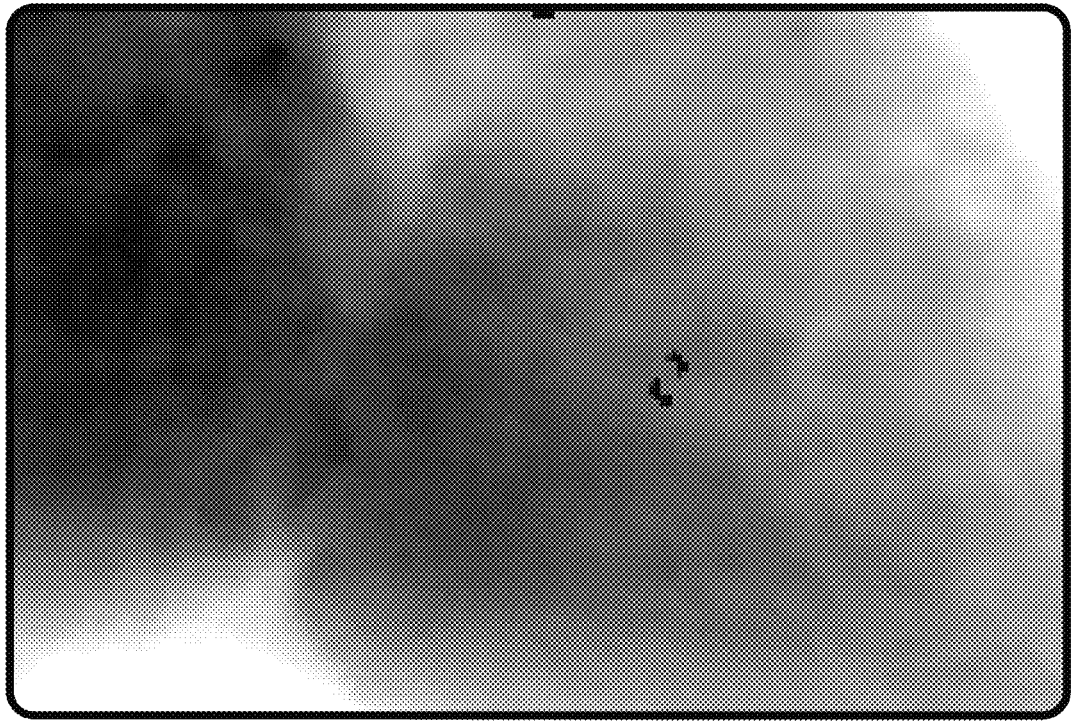
FIG. 26B is a simulated RAO fluoroscopic image taken 20 degrees off perpendicular to the septum depicting the lead of FIG. 24A including two alignable marker elements where the lead is not in intended alignment similar to as shown in FIGS. 25A-25B.

A simulated right anterior oblique (RAO) fluoroscopic image taken 20 degrees off perpendicular to the septum depicting the distal lead region 1204 as aligned in FIG. 24A is shown in FIG. 26A. As can been seen in the image of FIG. 26A, a fiducial shape of a single circle is present indicating alignment. Conversely, a simulated RAO fluoroscopic image taken 20 degrees off perpendicular to the septum depicting the distal lead region 1204 as unaligned in FIG. 25A is shown in FIG. 26B. As can been seen in the image of FIG. 26B, no fiducial shape of a single circle is present, and instead, two separate semicircles spaced apart from one another are present indicating non-acceptable alignment.

Figure 28D:
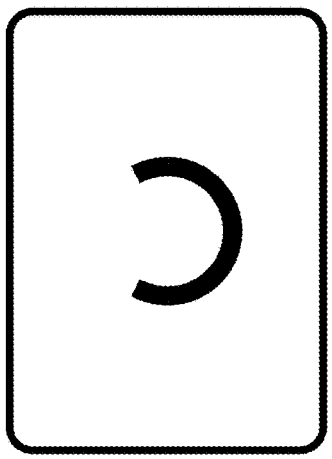
FIG. 28D depicts an illustrative image, taken perpendicular to the target site of FIG. 28A, where the lead is positioned and oriented as shown in FIG. 28A.
Figure 28E:
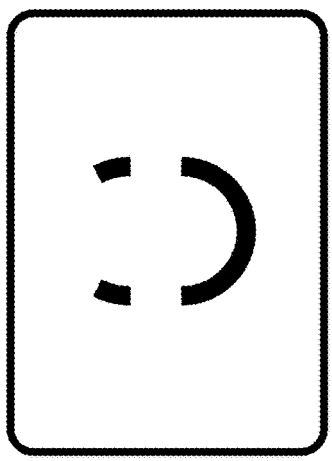
FIGS. 28E and 28F depicts illustrative images, taken perpendicular to the target site of FIG. 28A, where the lead is not positioned and oriented as intended.
Figure 28F:
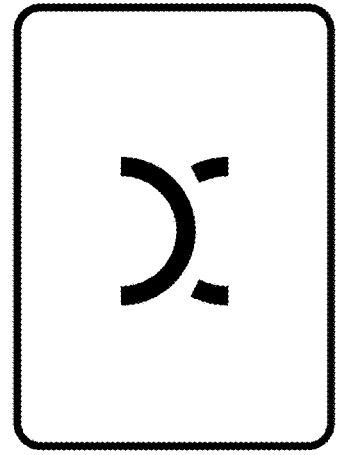
Figure 28A:
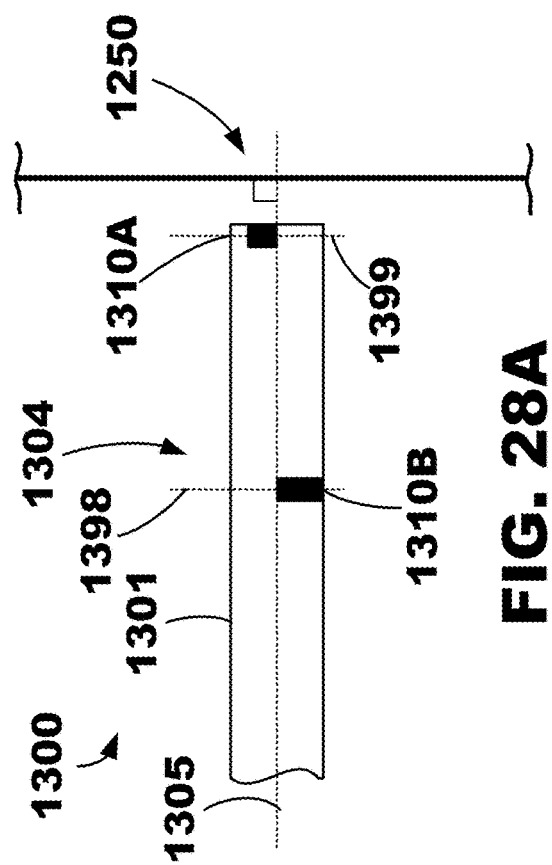
FIG. 28A depicts a side view of an aligned illustrative lead including two alignable marker elements being positioned proximate a target site.
Figures 28B, 28C:
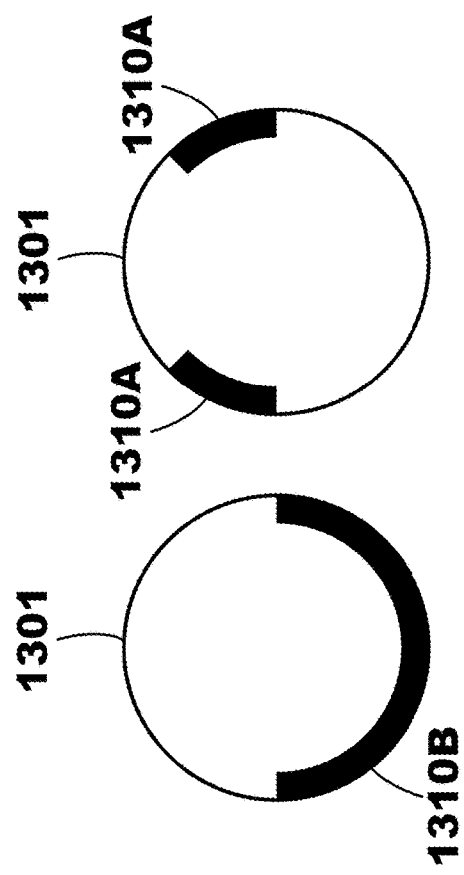
FIGS. 28B and 28C depict cross-sectional views of the lead of FIG. 28A.

Another illustrative lead 1300 aligned with respect to the target site 1250 and including two alignable marker elements 1310 that each have complementary shapes is depicted in FIGS. 28A-28C. The first alignable marker element 1310A includes two arcuate portions of a circle and the second alignable marker element 1310B includes a single arcuate portion of a circle or a semicircle. A cross sectional view of the lead body 1301 including the first alignable marker element 1310A taken across line 1399 is shown in FIG. 28C, and a cross sectional view of the lead body 1301 including the second alignable marker element 1310B taken across line 1398 is shown in FIG. 28B. As shown in FIG. 28A, the distal end region axis 1305 of the distal end region 1304 is substantially perpendicular to the target site 1250, e.g., the intraventricular septum, and thus, an image taken perpendicular to the target site depicted in FIG. 28D shows the fiducial shape of a single U-shape. Images taken perpendicular to the target site where the distal end region axis 1305 of the distal end region 1304 is not substantially perpendicular to the target site 1250 are shown in FIGS. 28E and 28F, where the first and second alignable marker elements 1310A, 1310B do not form the fiducial (such as the shape of a single U), thereby indicating misalignment.

Another illustrative lead 1400 aligned with respect to the target site 1250 and including two alignable marker elements 1410 that each have complementary shapes is depicted in FIGS. 29A-29C. The first alignable marker element 1410A includes a single arcuate portion of a circle (in particular, a semicircle extending approximately 90 degrees) and the second alignable marker element 1410B also includes a single arcuate portion of a circle (in particular, a semicircle extending 180 degrees). A cross sectional view of the lead body 1401 including the first alignable marker element 1410A taken across line 1499 is shown in FIG. 29C, and a cross sectional view of the lead body 1401 including the second alignable marker element 1410B taken across line 1498 is shown in FIG. 29B. As shown in FIG. 29A, the distal end region axis 1405 of the distal end region 1404 is substantially perpendicular to the target site 1250, e.g., the intraventricular septum, and thus, an image taken perpendicular to the target site depicted in FIG. 29D shows the fiducial shape of a single U-shape opened to the upper left. Images taken perpendicular to the target site where the distal end region axis 1405 of the distal end region 1404 is not substantially perpendicular to the target site 1250 are shown in FIGS. 29E and 29F, where the first and second alignable marker elements 1410A, 1410B do not form the fiducial shape (such as the shape of a single U), thereby indicating misalignment.

Figure 30B:
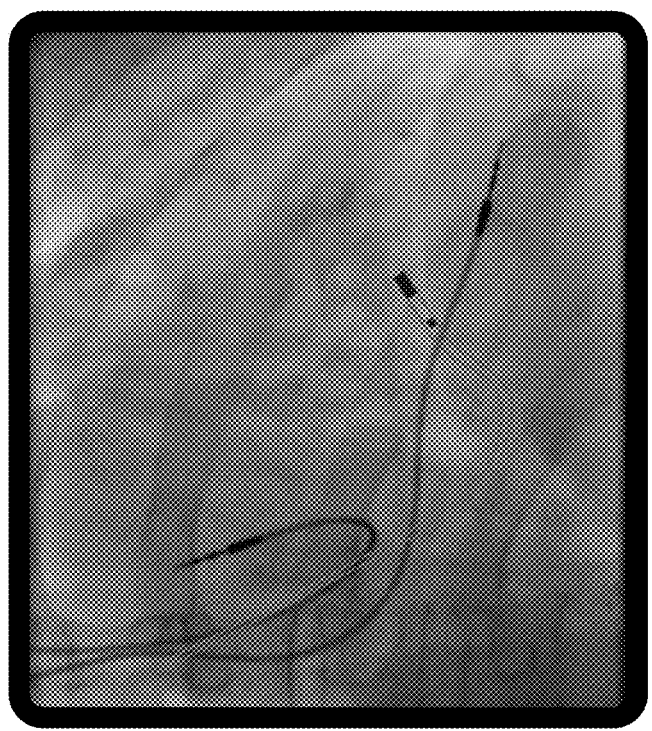
FIG. 30B is a simulated left anterior oblique (LAO) fluoroscopic image taken 20 degrees off perpendicular to the septum depicting the lead of FIG. 30A including two alignable marker elements.
Figure 30A:
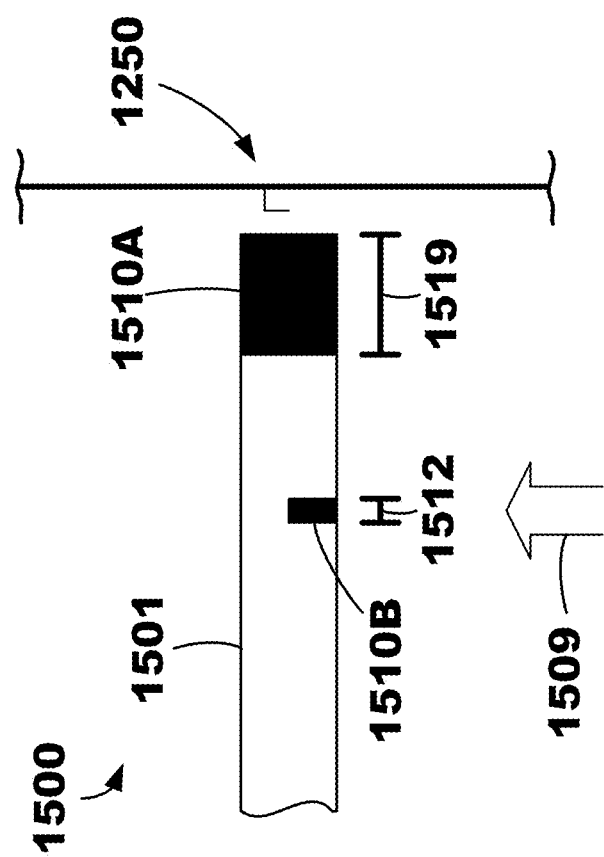
FIG. 30A depicts a side view of an aligned illustrative lead including two alignable marker elements being positioned proximate a target site.

Another illustrative lead 1500 aligned with respect to the target site 1250 and including two alignable marker elements 1510 that each have complementary shapes is depicted in FIGS. 30A-30B. The first alignable marker element 1510A may be a circular, or ring shaped, element and the second alignable marker element 1510B may be a portion of a circle (e.g., semicircle). In this embodiment, the first alignable marker element 1510A and the second alignable mark element 1510B define, or are, different sizes. In particular, the first alignable marker element 1510A defines a first length 1519 and the second marker element 1510B defines a second length 1512 that is shorter, or less, than the first length 1519. In one embodiment, the first length 1519 may be about 3 mm and the second length 1512 may be about 1 mm. It is be understood that, in other embodiments, the first marker element 1510A may have, or define, a length 1519 that is smaller, or less, than a length 1512 of the second marker element 1510B. The alignable marker elements having different lengths may help physicians to identify at-tip or behind-tip during advancing or rotating of the lead body 1501. Further, physicians may use a left anterior oblique (LAO) image or view, as shown in FIG. 30B, to check direction of catheter tip against septum, and depth pacing lead penetration. An LAO image may be taken from direction 1509 as shown in FIG. 30A.

Figure 31:
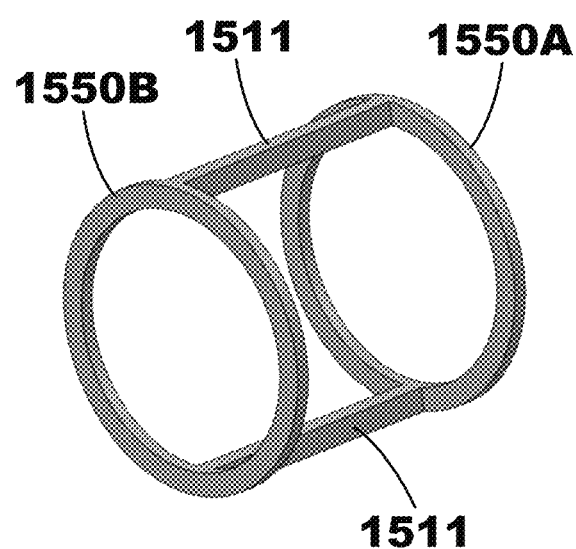
FIG. 31 is a perspective view of an illustrative embodiment of two alignable marker elements coupled using two extension elements.

A perspective view of two alignable marker elements 1550A, 1550B coupled using two extension elements 1511 is shown in FIG. 31. Although two extension elements 1511 are depicted herein, it is to be understood that one extension element or more than two extensions elements may be utilized. The extensions elements 1511 may provide fixed spacing between two alignable marker elements 1550A, 1550B such that, e.g., a physician may be able to use the distance between the two alignable marker elements 1550A, 1550B to determine penetration depth into the target region such as e.g., the ventricular septum. The extensions elements 1511 may comprise, or be formed of, the same material as the alignable marker elements 1550A, 1550B. In at least one embodiment, the two alignable marker elements 1550A, 1550B and two extension elements 1511 may be machined from tubing, which would aid in manufacturing and provide a given distance between the alignable marker elements 1550A, 1550B. The fixed spacing, or given distance, may allow a physician to make a small calculation to determine the angle of approach to the septal wall. Additionally, the extensions elements 1511 may assist in stiffening a distal end region of a lead (in other words, the distal end of the region may be more resilient as a result of the extension elements 1511 coupling the alignable marker elements 1550A, 1550B), which can negate effects of bending that may lead to misalignment during implantation. In at least one embodiment, the two alignable marker elements 1550A, 1550B and extension elements 1511 may be provided to the additive manufacturing systems described herein with respect to FIGS. 1-6.

Another illustrative lead 1600 aligned with respect to the target site 1250 and including two alignable marker elements 1610 that each have complementary shapes is depicted in FIGS. 32A-32C. The first alignable marker element 1610A includes four arcuate portions of a circle and the second alignable marker element 1610B includes three arcuate portions of a circle. Thus, the alignable marker elements 1610 of the lead 1600 are asymmetric, which may be used by a physician to determine where the distal end 1603 of the lead 1600 is located when viewed on imaging. Additionally, a physician may utilize the asymmetric alignable marker elements 1610 to count turns of the distal end region 1604 of the lead body 1601 about the axis 1605, for example, when implanting a fixation element such as a helix in the target site 1250. A cross sectional view of the lead body 1601 including the first alignable marker element 1610A taken across line 1699 is shown in FIG. 32C, and a cross sectional view of the lead body 1601 including the second alignable marker element 1610B taken across line 1698 is shown in FIG. 32B. As shown in FIG. 32A, the distal end region axis 1605 of the distal end region 1604 is substantially perpendicular to the target site 1250, e.g., the intraventricular septum, and thus, an image taken perpendicular to the target site depicted in FIG. 32D depicts the fiducial shape of nearly complete circle defining a gap 1615. In one or more embodiments, the alignable marker elements 1610 may be configured such that the gap 1615 indicates the direction of deflection 1650, e.g., via a pull-wire or the like, of the lead body 1601. Thus, it may be described that, when the alignable marker elements 1610 were aligned, the deflection direction 1650 may be shown in the imaging to aid a physician in alignment of the distal end region 1604 with the target site 1250.

Another illustrative lead 1700 aligned with respect to the target site 1250 and including two alignable marker elements 1710 that each have complementary shapes is depicted in FIGS. 33A-33C. Each of the first alignable marker element 1710A and the second alignable marker element 1710B are circles or rings, each having a different diameter. In this example, the first alignable marker element 1710A defines a smaller diameter than, the second alignable marker element 1710B. Thus, the alignable marker elements 1710 of the lead 1700 are asymmetric, which may be used by a physician to determine the distal end 1703 of the lead 1700 when viewed on imaging. A cross sectional view of the lead body 1701 including the first alignable marker element 1710A taken across line 1799 is shown in FIG. 33C, and a cross sectional view of the lead body 1701 including the second alignable marker element 1710B taken across line 1798 is line shown in FIG. 33B. As shown in FIG. 33A, the distal end region axis 1705 of the distal end region 1604 is substantially perpendicular to the target site 1250, e.g., the intraventricular septum, and thus, a RAO image taken perpendicular to the target site 1250 depicted in FIG. 33E depicts the fiducial shape of two concentric circles. A RAO image taken perpendicular to the target site where the distal end region axis 1705 of the distal end region 1704 is not substantially perpendicular to the target site 1250 is shown in FIG. 33D, where the first and second alignable marker elements 1710A, 1710B do not form the fiducial shape and instead form a single circle thereby indicating misalignment. In other words, the alignable marker elements 1710A, 1710B may be used to align and also to differentiate which direction the distal end region 1704 is pointing. If the smaller diameter, first alignable marker element 1710A is closer to the viewer (e.g., from where the imaging is being captured or taken), then the alignable marker elements 1710A, 1710A appear concentric. Conversely, if the larger diameter, second alignable marker element 1710B is closer to the viewer (e.g., from where the imaging is being captured or taken), then the alignable marker elements 1710A, 1710A will overlap and appear as a single circle.

Figure 34A:
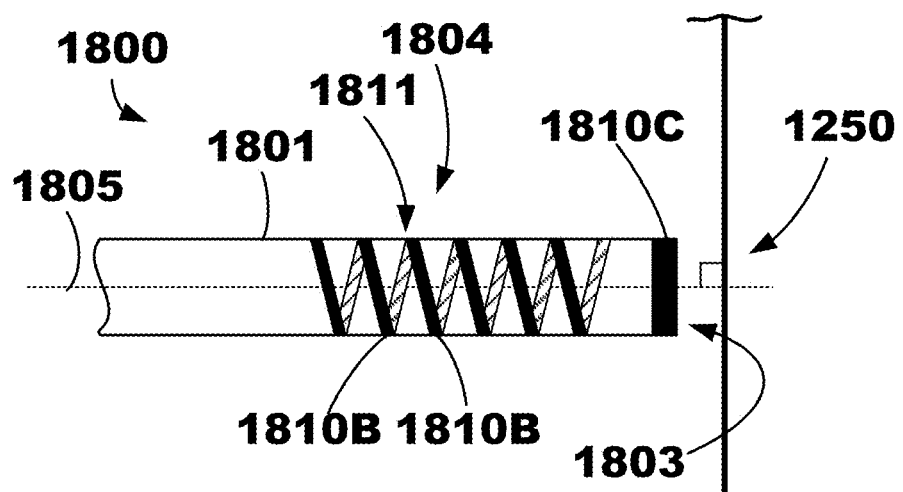
FIG. 34A depicts a side view of an aligned illustrative lead including a plurality of alignable marker elements in a coil being positioned proximate a target site.

Illustrative alignable marker elements 1810 may be included as part of a coil or helix as shown in the illustrative lead 1800 aligned with respect to the target site 1250 in FIG. 34A. In this embodiment, the lead 1800 includes an imageable coil 1811, e.g., comprising imageable material, positioned in a distal end region 1804 that may be described as including a plurality of alignable marker elements, each alignable marker element being a single 360 turn of the coil 1811. Two alignable marker elements are labeled in the embodiment of FIG. 34: a first alignable marker element 1810A; and a second alignable marker element 1810B. Perpendicular and parallel views of this embodiment may be used to determine alignment of distal end region 1804 of the lead body 1801 with the target site 1250 as shown in with respect to FIGS. 34B-34G.

Figure 34B:
FIG. 34B depicts an illustrative image, taken parallel to the target site of FIG. 34A, indicating that the lead is oriented towards the target site.
Figure 34C:
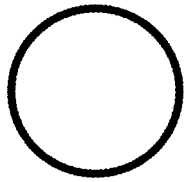
FIG. 34C depicts an illustrative image, taken perpendicular to the target site of FIG. 34A, indicating that the lead is oriented towards the target site.
Figure 34D:
FIG. 34D depicts an illustrative image, taken parallel to the target site of FIG. 34A, indicating that the lead is not oriented towards the target site.
Figure 34E:
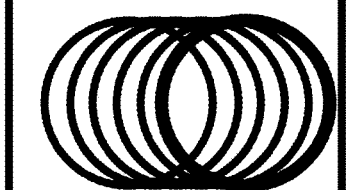
FIG. 34E depicts an illustrative image, taken perpendicular to the target site of FIG. 34A, indicating that the lead is not oriented towards the target site.
Figure 34F:
FIG. 34F depicts an illustrative image, taken parallel to the target site of FIG. 34A, indicating that the lead is not oriented towards the target site.
Figure 34G:
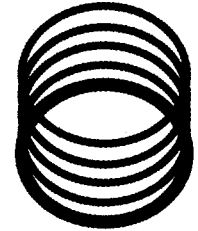
FIG. 34G depicts an illustrative image, taken perpendicular to the target site of FIG. 34A, indicating that the lead is not oriented towards the target site.

For instance, the lead 1800 is aligned in FIGS. 34B and 34C, which are illustrative images, the former taken parallel to the target site 1250 (e.g., radially to the axis 1805) and the later taken perpendicular to the target site 1250 (e.g., axially to the axis 1805). The coil 1811 includes uniform spacing between coils in FIG. 34B and forms a fiducial shape of a circle in FIG. 34C thereby indicating that the lead 1800 is oriented towards the target site. Further, the lead 1800 is not aligned to the target site 1250 in FIGS. 34D-34G, which are also illustrative images where FIGS. 34D and 34F are taken parallel to the target site 1250 and FIGS. 34E and 34G are taken perpendicular (e.g., RAO) to the target site 1250. The coil 1811 does not have uniform spacing or uniform shape between coils in FIG. 34D and does not form a fiducial shape of a circle in FIG. 34E (e.g., horizontally overlapping circles are shown) thereby indicating that the lead 1800 is misaligned with respect to the target site 1250. Likewise, the coil 1811 appears tilted or angled in FIG. 34F and does not form a fiducial shape of a circle in FIG. 34G (e.g., vertically overlapping circles are shown) thereby indicating that the lead 1800 is misaligned with respect to the target site 1250. In one or more embodiments, a decoder (e.g., a set of examples of the shape of the coil 1811 when in parallel to the target site 1250 at various angles) may be used to determine the offset angle or angle not perpendicular to the target site 1250. Further, in at least one embodiment, the coil 1811 could be variable pitch to aid in diagnosis of offset.

Optionally, this embodiment also includes a tip alignable marker element 1810C, which is not part of the coil 1811. The orientation of a distal end 1803 of the distal end region 1804 would be able to be determined using the tip alignable marker element 1810C with respect to the coil 1811. Additionally, the tip alignable marker element 1810C would "stack" with the coil 1811 creating a fiducial shape of a concentric bright ring when viewed axially along the axis 1805 as shown in FIG. 34C.

As described herein, the illustrative implantable medical devices, e.g., leads, catheters, etc. may include more than two alignable marker elements. An illustrative lead 1900 positioned in an unintended and less desirable alignment with respect to the target site 1250 is depicted in FIG. 35A. The lead 1900 includes four alignable marker elements 1910A, 1910B, 1910C, 1910D. Alignable marker elements 1910A, 1910C are circular and alignable marker elements 1910B, 1910D are semicircular such that when the distal end region 1904 is of the lead 1900 is misaligned, an image, taken perpendicular to the target site of FIG. 35A will show two circles, one of which is darker or thicker than the other, as shown in FIG. 35B. The darker circle being above the lighter circle, in this example, shows that the distal end or tip 1903 is pointing up. In other words, the distal region 1904 of the lead 1900 is misaligned vertically in the upward direction.

One or more alignable marker elements may define a directionally indicative shape that, when viewed using imaging, may indicate the direction of the distal end region with respect to the target site. An aligned illustrative lead 2000 including a directionally indicative alignable marker element 2010 being positioned proximate a target site 1250 is depicted in FIG. 36A. As shown, the distal end region 2004 is positioned substantially perpendicular to the target site 1250 (e.g., the distal axis 2005 extending along the distal end region 2004 is perpendicular to a plane of the target site 1250). In this embodiment, the directionally indicative alignable marker element 2010 includes, or defines, an arrow shape that points towards the distal end, or tip, 2003 of the lead body 2001. An illustrative image, taken perpendicular to the target site 1250, where the lead is positioned and oriented as shown in FIG. 36A, is shown in FIG. 36B. As shown in FIG. 36B, the arrow is not visible since the distal end region 2004 is substantially aligned with (e.g., perpendicular to) the target site 1250. Illustrative images, taken perpendicular to the target site of FIG. 36A, where the lead is not positioned and oriented as intended are shown in FIGS. 36C and 36D. As shown in FIG. 36C, the "arrow" image appears to point upward, which may indicate that the distal end region 2004 is vertically misaligned upwardly. As shown in FIG. 36C, the "arrow" image appears to point down and to the left, which may indicate that the distal end region 2004 is vertically misaligned downwardly and horizontally misaligned to the left.

Figure 37:
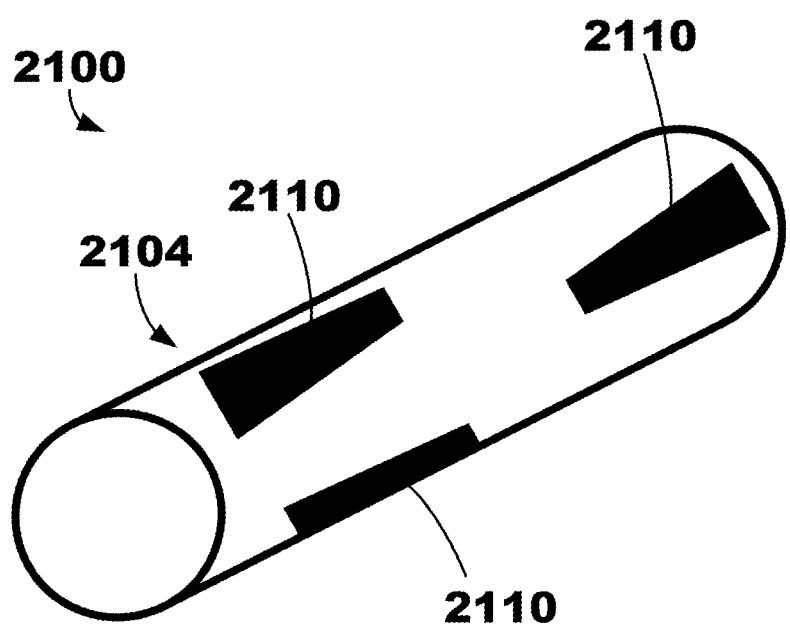
FIG. 37 is a perspective view of an illustrative lead including a plurality of alignable marker elements.

As described herein, multiple alignable marker elements may be utilized that define different shapes and sizes. A perspective view of an illustrative lead 2100 including a plurality of alignable marker elements 2110 having trapezoidal shapes in depicted in FIG. 37. In other words, the "wedge"-shaped alignable marker elements 2110 may define, or form, the fiducial shape of an annular ring when aligned. When the distal end region 2104 is not aligned, the long trapezoid shape of the alignable marker elements 2110 may create, or generate, a shadow type projection indicating that the distal end region 2104 is offset. Additionally, in other views, orientation can be determined based on non-uniform geometry of the alignable marker elements 2110.

A few more embodiments including a plurality of alignable marker elements are depicted in FIGS. 38-39. An aligned illustrative lead 2200 including a plurality of alignable marker elements 2210A, 2210B being positioned proximate a target site 1250 is depicted in FIG. 38A. In this embodiment, each of the first alignable marker element 2210A and the second alignable marker element 2210B include, or comprise, a plurality of marker portions arranged in a circular fashion and spaced about circumferentially and axially. An additional side view of the distal region 2204 of the lead 2200 rotated about the axis 2205 90 degrees from the view of FIG. 38A is depicted in FIG. 38B. As shown in FIG. 38A, the distal end region axis 2205 of the distal end region 2204 is substantially perpendicular to the target site 1250, e.g., the intraventricular septum, and thus, an image taken perpendicular to the target site 1250 depicted in FIG. 38C shows the fiducial shape of a broken circle. Additionally, it may be described that "clear" slots indicate perfect alignment. Another image taken perpendicular to the target site where the distal end region axis 2205 of the distal end region 2204 is not substantially perpendicular to the target site 1250 is shown in FIG. 38D, where the first and second alignable marker elements 2210A, 2210B do not form the fiducial shape and instead overlap thereby indicating misalignment. Additionally, the longer span, or distance, between the first alignable marker element 2210A and the second alignable marker element 2210B may allow better resolution in axial view alignment.

Figure 39B:
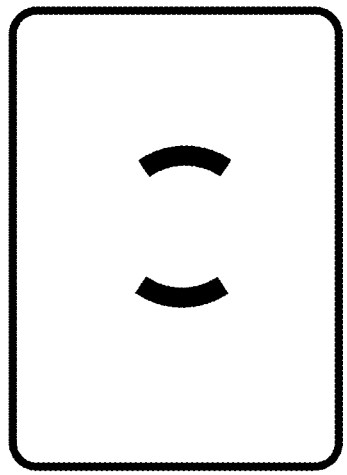
FIG. 39B depicts an illustrative image, taken perpendicular to the target site of FIG. 39A, where the lead is positioned and oriented as shown in FIG. 39A.
Figure 39C:
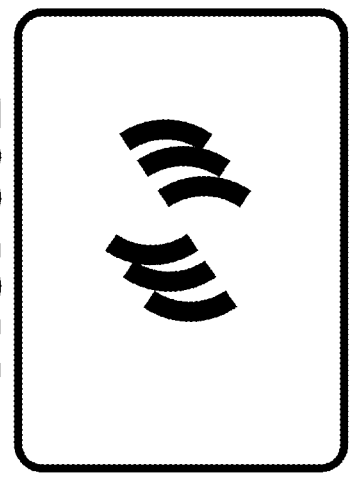
FIG. 39C depicts an illustrative image, taken perpendicular to the target site of FIG. 39A, where the lead is not positioned and oriented as intended.
Figure 39A:
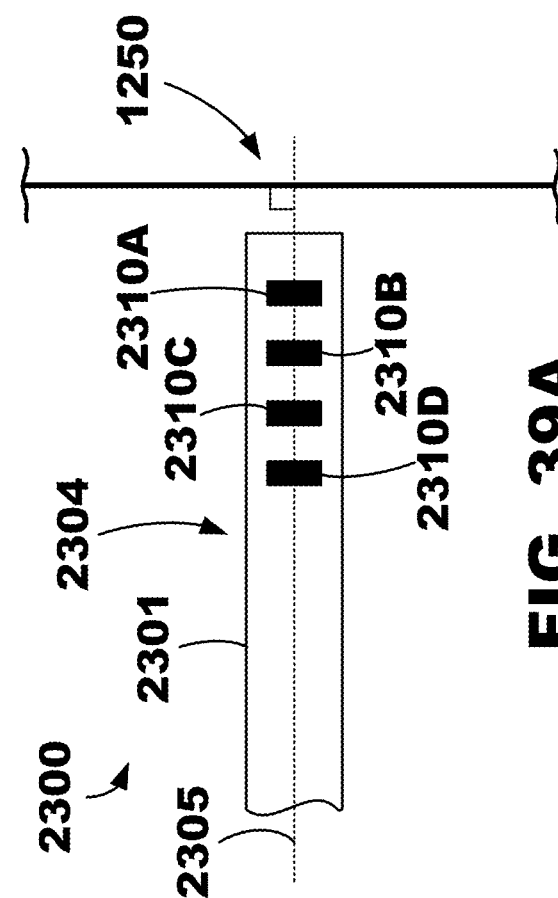
FIG. 39A depicts a side view of an aligned illustrative lead including a plurality of alignable marker elements being positioned proximate a target site.

An aligned illustrative lead 2300 including a plurality of alignable marker elements 2310A, 2310B, 2310C, 2310D being positioned proximate a target site 1250 is depicted in FIG. 39A. In this embodiment, each of the alignable marker elements 2310A, 2310B, 2310C, 2310D include, or comprise, two semi circles or arcs opposite each other about the leady body 2301. Further, the alignable marker elements 2310A, 2310B, 2310C, 2310D are uniformly spaced from each other along the distal end axis 2305. As shown in FIG. 39A, the distal end region axis 2305 of the distal end region 2304 is substantially perpendicular to the target site 1250, e.g., the intraventricular septum, and thus, an image taken perpendicular to the target site 1250 depicted in FIG. 39B shows the fiducial shape of a two partial circles or arcs opposite each other. An image taken perpendicular to the target site where the distal end region axis 2305 of the distal end region 2304 is not substantially perpendicular to the target site 1250 is shown in FIG. 39C, where the plurality of alignable marker elements 2310A, 2310B, 2310C, 2310D do not form the fiducial shape and instead overlap thereby indicating misalignment. Additionally, a blurry or out of focus image may also indicate unintended alignment. When imaged or view laterally (e.g., from the side), clear slots between alignable marker elements 2310A, 2310B, 2310C, 2310D indicate between acceptable alignment. In one or more embodiments, one or more of the alignable marker elements 2310A, 2310B, 2310C, 2310D may only include a single arc, which may be used to indicate a deflection plane. Additionally, a longer span, or distance, between the alignable marker elements 2310A, 2310B, 2310C, 2310D may provide, or allow, better resolution in axial view alignment. When imaged or view laterally (e.g., from the side), too many bars or stripes may indicate misalignment because both of the two arcs of each of the alignable marker elements 2310A, 2310B, 2310C, 2310D may be visible as opposed to overlapping.

It is to be understood that the alignable marker element concepts described herein may be utilized with any implantable medical device such as, e.g., leads, catheters, leadless devices, etc. Further, in one or more embodiments, one alignable marker element may be located on a delivery catheter and another alignable element may be located on the device being delivered by the delivery catheter (such as, e.g., a lead).

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

ILLUSTRATIVE EXAMPLES

Example 1: An implantable apparatus comprising:
a body defining a distal end region extending along a distal end region axis; and
two alignable marker elements coupled to the body within the distal end region, wherein each of two alignable marker elements defines a complementary shape that complements the other alignable marker element such that, when the distal end region is viewed axially, the two alignable marker elements form a fiducial shape indicative of acceptable alignment of the distal end region for positioning at a target site.

Example 2: The apparatus of example 1, wherein the two alignable marker elements are radiopaque and viewable when located within a patient's heart using fluoroscopy.

Example 3: The apparatus of example 1, wherein the two alignable marker elements are echogenic and viewable when located within a patient's heart using ultrasound.

Example 4: The apparatus as in any one of examples 1-3, wherein the complementary shape of each of the two alignable marker elements is a circle and the fiducial shape is a single circle.

Example 5: The apparatus as in any one of examples 1-3, wherein the complementary shape of each of the two alignable marker elements is a semicircle and the fiducial shape is a single circle.

Example 6: The apparatus as in any one of examples 1-3, wherein the complementary shape of each of the two alignable marker elements is at least a portion of a circle and the fiducial shape is at least a portion of a single circle.

Example 7: The apparatus as in any of examples 1-6, wherein each of the two alignable marker elements defines a different size than each other.

Example 8: The apparatus as in example 7, wherein a first alignable marker element of the two alignable marker elements defines a first length along the distal end region axis and a second alignable marker element of the two alignable marker elements defines a second length along the distal end region axis, wherein the first length is greater than the second length.

Example 9: The apparatus as any one of examples 7-8, wherein each of the two alignable marker elements defines a different diameter than each other.

Example 10: The apparatus as in any one of examples 1-3, wherein the complementary shape of each of the two alignable marker elements comprises a plurality of portions of circle and the fiducial shape is a near-complete portion of a single circle defining a gap, wherein the gap is indicative of deflection direction of the body.

Example 11: The apparatus as in example 10, wherein a first alignable marker element of the two alignable marker elements comprises a first number of portions of the circle and a second alignable marker elements of the two alignable marker elements a second number of portions of the circle, wherein the first number is greater than the second number.

Example 12: The apparatus as in any one of examples 1-11, further comprising at least one additional alignable marker element that defines another complementary shape that complements the two alignable marker elements such that, when the distal end region is viewed axially, the two alignable marker elements and the at least one additional alignable marker element form the fiducial shape indicative of acceptable alignment of the distal end region for positioning at the target site.

Example 13: The apparatus as in example 12, wherein the at least one additional alignable marker element defines a different size than at least one of the two alignable marker elements, wherein, when the distal end region is viewed axially, the two alignable marker elements and the at least one additional alignable marker element form a non-alignment fiducial shape indicative of unacceptable alignment of the distal end region.

Example 14: The apparatus as in any one of examples 1-13, wherein the two alignable marker elements define a coil extending along the distal axis, wherein, when the distal end region is viewed radially, a minimum length between the two alignable marker elements is indicative of acceptable alignment of the distal end region for positioning at the target site.

Example 15: The apparatus as in any one of examples 1-13, further comprising at least one extension member coupled to and extending between the two alignable marker elements.

Example 16: The apparatus as in any of examples 1-15, wherein the body is a delivery catheter or a lead.

Example 17: The apparatus as in any of examples 1-15, wherein the body comprises:
a delivery catheter defining a lumen, wherein a first alignable marker element of the two alignable marker elements is coupled to the delivery catheter; and
a lead located within the delivery catheter, wherein a second alignable marker element of the two alignable marker elements is coupled to the lead.

Example 18: The apparatus as in any of examples 1-17, further comprising a fixation element coupled to the distal end region of the body to couple the body to the target site.

Example 19: An implantable apparatus comprising:
a body defining a distal end region extending along a distal end region axis; and
an alignable marker element coupled to the body within the distal end region defining a directionally indicative shape that, when the distal end region is viewed axially, is indicative of the direction of the distal end region away a target site.

Example 20: An additive manufacturing system comprising:
- one or more heating cartridges, each extending from a proximal side to a distal side and comprising a substrate inlet port at the proximal side and a substrate outlet port at the distal side, each heating cartridge defining an interior volume and a substrate channel extending through the interior volume from the proximal side to the distal side, each heating cartridge defining a first filament port in fluid communication with the interior volume to receive a first filament;
- a heating element thermally coupled to each heating cartridge of the one or more heating cartridges to heat the interior volume;
- a filament handling system comprising one or more motors to feed at least the first filament through the first filament port into the interior volume;
- a substrate handling system comprising:
- a head stock comprising a distal clamp to secure a distal portion of an elongate substrate, wherein the substrate is positioned to pass through the substrate channel when secured by the head stock; and
- one or more motors to translate or rotate one or both of the substrate when secured by the head stock and the heating cartridge relative to one another;
- an intermediate component system positioned proximate the heating cartridge to position two alignable marker elements, wherein each of two alignable marker elements defines a complementary shape that complements the other alignable marker element; and
- a controller operably coupled to the heating element, one or more motors of the filament handling system, and one or more motors of the substrate handling system, the controller configured to:
  - control the one or more motors of the filament handling system to selectively control the feeding of the first filament into the interior volume;
  - activate the heating element to melt any portion of the first filament in the interior volume;
  - control one or more motors of the substrate handling system to move one or both of the substrate and the one or more heating cartridges relative to one another in at least a longitudinal direction to form a first elongate catheter jacket around the substrate; and
  - control the intermediate component system to deposit the two alignable marker elements on the first elongate catheter jacket within a distal end region element extending along a distal end region axis such that, when the distal end region is viewed axially, the two alignable marker elements form a fiducial shape indicative of acceptable alignment of the distal end region for positioning at a target site.

Example 21: The system as in example 20, wherein the controller is further configured to:
- control the one or more motors of the filament handling system to selectively control the feeding of a second filament into the interior volume;
- activate the heating element to melt any portion of the second filament in the interior volume; and
- control one or more motors of the substrate handling system to move one or both of the substrate and the one or more heating cartridges relative to one another in at least a longitudinal direction to form a second elongate catheter jacket around the first elongate catheter jacket and the two alignable marker elements.

Example 22: The system as in any one of examples 20-21, wherein the two alignable marker elements are radiopaque and viewable when located within a patient's heart using fluoroscopy.

Example 23: The system as in any one of examples 20-21, wherein the two alignable marker elements are echogenic and viewable when located within a patient's heart using ultrasound.

Example 24: The system as in any one of examples 20-23, wherein the complementary shape of each of the two alignable marker elements is at least one portion of a circle and the fiducial shape is a single circle.

Example 25: A method for navigating an implantable apparatus in a patient's heart comprising:
- providing an implantable apparatus comprising:
  - a body defining a distal end region extending along a distal end region axis; and
  - two alignable marker elements coupled to the body within the distal end region, wherein each of two alignable marker elements defines a complementary shape that complements the other alignable marker element such that, when the distal end region is viewed axially, the two alignable marker elements form a fiducial shape;
- navigating the distal end region proximate a target site;
- generating an image taken perpendicular to the target site of the alignable marker elements; and
- determining that the alignable marker elements form the fiducial shape in the generated image indicating acceptable alignment of the distal end region.

Example 26: The method as in example 25, further comprising:
- adjusting one or both of orientation and location of the distal end region proximate the target site if the alignable marker elements do not form the fiducial shape in the generated image;
- generating another image taken perpendicular to the target site of the alignable marker elements; and
- determining that the alignable marker elements form the fiducial shape in the generated another image indicating acceptable alignment of the distal end region.

Example 27: The method as in any one of examples 25-26, wherein the image taken perpendicular to the target site of the alignable marker elements is a left anterior oblique image of the patient's heart.

Example 28: The method as in any one of examples 25-27, wherein the two alignable marker elements are radiopaque and viewable when located within a patient's heart using fluoroscopy, wherein the image taken perpendicular to the target site of the alignable marker elements is a fluoroscopic image.

Example 29: The method as in any one of examples 25-27, wherein the two alignable marker elements are echogenic and viewable when located within a patient's heart using ultrasound, wherein the image taken perpendicular to the target site of the alignable marker elements is an ultrasound image.

Example 30: The method as in any one of examples 25-29, wherein the complementary shape of each of the two alignable marker elements is at least one portion of a circle and the fiducial shape is a single circle.

Example 31: The method as in any one of examples 25-30, wherein the target site is the intraventricular septum, wherein navigating the distal end region proximate the target site comprising navigating the distal end region into the right ventricular proximate the intraventricular septum.

Example 32: A method of forming a lead comprising:
providing a lead body extending from a proximal end region to a distal end region defining a lumen, wherein a conductor is positioned within the lumen;
defining an opening through the lead body;
extending the conductor outside of the lead body through the lumen;
positioning a C-shaped electrode proximate the conductor outside of the lead body;
electrically coupling C-shaped electrode to the conductor; and
mechanically coupling the C-shaped electrode onto the lead body.

Example 33: The method as in example 32, wherein the lead body comprises an extension region and an electrode coupling region, wherein the electrode coupling region is where the C-shaped electrode is coupled to the lead body, wherein the extension region defines a first outer diameter and the electrode coupling region defines a second outer diameter that is less than the first outer diameter.

Example 34: The method as in example 33, wherein the C-shaped electrode defines an inner surface, an outer surface, and a thickness between the inner surface and the outer surface, wherein the thickness of the C-shaped electrode is less than or equal to a difference between the first outer diameter and the second outer diameter.

Example 35: The method as in any of examples 32-34, wherein providing the lead body comprises utilizing additive manufacturing to form the lead body about the conductor.

Example 36: The method as in any of examples 32-35, wherein electrically coupling C-shaped electrode to the conductor comprises laser welding the C-shaped electrode to the conductor.

Example 37: The method as in example 36, wherein the C-shaped electrode defines an inner surface and an outer surface, wherein the laser welding is applied to the outer surface of the C-shaped electrode to electrically couple the inner surface to the conductor.

Example 38: The method as in any of examples 32-37, wherein the C-shaped electrode extends along a circumference from a first end to a second end and defines a gap between the first end and the second end, wherein mechanically coupling the C-shaped electrode onto the lead body comprises deforming the C-shaped electrode to the conductor to close the gap such that the first end contacts the second end.

Example 39: The method as in any of examples 32-38, wherein the method further comprises closing the opening in the lead body after extending the conductor outside of the lead body through the lumen.

Example 40: The method of example 39, wherein closing the opening in the lead body comprises thermo-bonding the lead body.

Example 41: The method as in any of examples 32-40, wherein the lead body is less than or equal to 3 Fr.

Example 42: The method as in any of examples 32-41, wherein the lead body is less than or equal to 4 Fr.

Example 43: A lead comprising:
a lead body extending from a proximal end to a distal end and defining an S-shape region proximate the distal end, a first apex area within the S-shaped region and a second apex area within the S-shaped region;
a first electrode positioned at the first apex area; and
a second electrode positioned at the second apex area.

Example 44: The lead of example 43, wherein each of the first and second electrodes is a coil electrode.

Example 45: The lead as in any of examples 43-44, wherein the lead body is less than or equal to 3 Fr.

Example 46: The lead as in any of examples 43-44, wherein the lead body is less than or equal to 4 Fr.

Example 47: The lead as in any of examples 43-46, wherein the lead body further defines a straight portion positioned proximal to the S-shaped region, wherein the straight portion extends along and defines an axis when undeflected, wherein at least one of the first and second apex areas, when undeflected, are located away from the axis at a perpendicular radial distance that is greater than the remainder of the lead body.

Example 48: The lead as in example 47, wherein both of the first and second apex areas, when undeflected, are located away from the axis at a radial distance that is greater than the remainder of the lead body.

Example 49: The lead as in any of examples 43-48, wherein the first apex area is located on the opposite side of the axis than the second apex area.

Example 50: The lead as in any of examples 43-49, wherein the S-shaped region defines a first curve portion and a second curve portion distal from the first curve portion, wherein the first curve portion defines a first radius and the second curve portion defines a second radius, wherein, when the lead is undeflected, the second radius is less than the first radius.

Example 51: The lead as in example 50, wherein the lead body defines an end curve portion distal to the S-shaped region.

Example 52: The lead as in example 51, wherein the end curve portion defines a third radius that, when the lead is undeflected, is less than the second radius.

Thus, various embodiments described herein are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of" "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

What is claimed:

1. An implantable apparatus comprising:
   a body defining a distal end region extending along a distal end region axis; and
   two alignable marker elements coupled to the body within the distal end region, wherein each of the two alignable marker elements defines a complementary shape that complements the other alignable marker element such that, when the distal end region is viewed axially, the two alignable marker elements form a fiducial shape indicative of acceptable alignment of the distal end region for positioning at a target site.

2. The apparatus of claim 1, wherein the two alignable marker elements are at least one of radiopaque and viewable when located within a patient's heart using fluoroscopy and echogenic and viewable when located within a patient's heart using ultrasound.

3. The apparatus of claim 1, wherein the complementary shape of each of the two alignable marker elements is at least a portion of a circle and the fiducial shape is at least a portion of a single circle.

4. The apparatus of claim 3, wherein the complementary shape of each of the two alignable marker elements is a circle or a semicircle and the fiducial shape is a single circle.

5. The apparatus of claim 1, wherein each of the two alignable marker elements defines a different size than each other.

6. The apparatus of claim 5, wherein a first alignable marker element of the two alignable marker elements defines a first length along the distal end region axis and a second alignable marker element of the two alignable marker elements defines a second length along the distal end region axis, wherein the first length is greater than the second length.

7. The apparatus of claim 5, wherein each of the two alignable marker elements defines a different diameter than each other.

8. The apparatus of claim 7, wherein the complementary shape of each of the two alignable marker elements comprises a plurality of portions of circle and the fiducial shape is a near-complete portion of a single circle defining a gap, wherein the gap is indicative of deflection direction of the body.

9. The apparatus of claim 8, wherein a first alignable marker element of the two alignable marker elements comprises a first number of portions of the circle and a second alignable marker element of the two alignable marker elements a second number of portions of the circle, wherein the first number is greater than the second number.

10. The apparatus of claim 1, further comprising at least one additional alignable marker element that defines another complementary shape that complements the two alignable marker elements such that, when the distal end region is viewed axially, the two alignable marker elements and the at least one additional alignable marker element form the fiducial shape indicative of acceptable alignment of the distal end region for positioning at the target site.

11. The apparatus of claim 10, wherein the at least one additional alignable marker element defines a different size than at least one of the two alignable marker elements, wherein, when the distal end region is viewed axially, the two alignable marker elements and the at least one additional alignable marker element form a non-alignment fiducial shape indicative of unacceptable alignment of the distal end region.

12. The apparatus of claim 1, wherein the two alignable marker elements define a coil extending along the distal axis, wherein, when the distal end region is viewed radially, a minimum length between the two alignable marker elements is indicative of acceptable alignment of the distal end region for positioning at the target site.

13. The apparatus of claim 1, further comprising at least one extension member coupled to and extending between the two alignable marker elements.

14. The apparatus of claim 1, wherein the body is a delivery catheter or a lead.

15. The apparatus of claim 1, further comprising a fixation element coupled to the distal end region of the body to couple the body to the target site.

16. An implantable apparatus comprising:
   a body defining a distal end region extending along a distal end region axis; and
   an alignable marker element coupled to the body within the distal end region defining a directionally indicative shape that, when the distal end region is viewed axially, is indicative of the direction of the distal end region away from a target site.

* * * * *